United States Patent [19]
deFougerolles et al.

[11] Patent Number: 5,891,841
[45] Date of Patent: Apr. 6, 1999

[54] METHODS OF USING INTERCELLULAR ADHESION MOLECULE-3 (ICAM-3), ANTIBODIES THERETO, AND SOLUBLE FRAGMENTS THEREOF

[75] Inventors: Antonin R. deFougerolles, Cambridge, United Kingdom; Timothy A. Springer, Chestnut Hill, Mass.

[73] Assignee: The Center for Blood Research, Inc., Boston, Mass.

[21] Appl. No.: 474,087

[22] Filed: Jun. 7, 1995

Related U.S. Application Data

[60] Division of Ser. No. 38,990, filed as PCT/US92/04896 Nov. 6, 1992, abandoned, which is a continuation-in-part of Ser. No. 712,879, Jun. 11, 1991, abandoned.

[51] Int. Cl.$^6$ .................................................. A61K 38/17
[52] U.S. Cl. ............................... 514/2; 514/12; 514/885; 514/886; 514/826; 424/130.1; 424/139.1
[58] Field of Search .................................. 514/2, 12, 885, 514/886, 826; 424/130.1, 139.1

[56] References Cited

U.S. PATENT DOCUMENTS

| | | | |
|---|---|---|---|
| 5,081,034 | 1/1992 | Bevilacqua et al. | 435/252.33 |
| 5,272,263 | 12/1993 | Hession et al. | 536/23.5 |
| 5,525,487 | 6/1996 | Gallatin et al. | 435/69.1 |
| 5,532,127 | 7/1996 | Gallatin et al. | 435/6 |
| 5,663,293 | 9/1997 | Gallatin et al. | 530/324 |
| 5,730,983 | 3/1998 | Wegner et al. | 424/185.1 |

FOREIGN PATENT DOCUMENTS

| | | |
|---|---|---|
| 0 289 949 | 11/1988 | European Pat. Off. . |
| 0 314 317 | 5/1989 | European Pat. Off. . |
| 0 314 863 | 5/1989 | European Pat. Off. . |
| 0 362 531 | 4/1990 | European Pat. Off. . |
| 0 386 906 | 9/1990 | European Pat. Off. . |
| 0 387 668 | 9/1990 | European Pat. Off. . |
| 0 408 859 | 1/1991 | European Pat. Off. . |
| 0 468 257 | 1/1992 | European Pat. Off. . |
| WO 89/02922 | 4/1989 | WIPO . |
| WO 90/05539 | 5/1990 | WIPO . |
| WO 90/05786 | 5/1990 | WIPO . |
| WO 90/06953 | 6/1990 | WIPO . |
| WO 90/13300 | 11/1990 | WIPO . |
| WO 91/10683 | 7/1991 | WIPO . |
| WO 91/16928 | 11/1991 | WIPO . |
| WO 91/18010 | 11/1991 | WIPO . |
| WO 91/18011 | 11/1991 | WIPO . |
| WO 92/00751 | 1/1992 | WIPO . |
| WO 92/04034 | 3/1992 | WIPO . |
| WO 92/06119 | 4/1992 | WIPO . |
| WO 92/22323 | 12/1992 | WIPO . |
| WO 93/14776 | 8/1993 | WIPO . |
| WO 94/17100 | 8/1994 | WIPO . |

OTHER PUBLICATIONS

Staunton et al., Cell 61, 243–254, 1990.
Laskey, Science 250, 964–969, 1992.
Ashkenazi, A. et al., "Protection against endotoxic shock by a tumor necrosis factor receptor immunoadhesin," *Proc. Natl. Acad. Sci. USA* 88:10535–10539 (Dec. 1991).
Capon, D. J. et al., "Designing CD4 immunoadhesins for AIDS therapy," *Nature* 337:525–531 (1989).
Chen, C. and H. Okayama, "High–Efficiency Transformation of Mammalian Cells by Plasmid DNA," *Mol. Cell. Biol.* 7(8):2745–2752 (1987).
Corpet, F., "Multiple sequence alignment with hierarchical clustering," *Nucl. Acids Res.* 16(22):10881–10890 (1988).
de Fougerolles, A. R. et al., "Cloning and Expression of Intercellular Adhesion Molecule 3 Reveals Strong Homology to Other Immunoglobulin Family Counter–receptors for Lymphocyte Function–associated Antigen 1," *J. Exp. Med.* 177(4):1187–1192 (Apr. 1993).
Hadam, M. R., "N11 Cluster report: CDw50," in: *Leukocyte Typing IV*, Knapp et al., eds., Oxford: Oxford University Press pp. 667–670 (1989).
Hunkapiller, T. and L. Hood, "The growing immunoglobulin gene superfamily," *Nature* 323:15–16 (1986).
Knapp, W. et al., "CD Antigens 1989," *Blood* 4:1448–1450 (1989).
Lozano, F. et al., "Effect of protein kinase C activators on the phosphorylation and the surface expression of the CDw50 Leukocyte antigen," *Eur. J. Biochem.* 203:321–326 (Jan. 1992).
Lozano, F. et al., "Isolation and Characterisation of CDw50 Negative Jurkat T–Cell Line Variant (PPL.1)," *Leukemia Res.* 17(1):9–16 (Jan. 1993).
Newman, P. J. et al., "PECAM–1 (CD31) Cloning and Relation to Adhesion Molecules of the Immunoglobulin Gene Superfamily," *Science* 247:1219–1222 (Mar. 1990).
Springer, T. A., "Adhesion receptors of the immune system," *Nature* 346:425–434 (Aug. 1990).
Staunton, D. E. et al., "Functional cloning of ICAM–2, a cell adhesion ligand for LFA–1 homologous to ICAM–1," *Nature* 339:61–64 (1989).
Stockinger, H. et al., "Molecular Characterization and Functional Analysis of the Leukocyte Surface Protein CD31," *J. Immunol.* 145:3889–3897 (Dec. 1990).
Williams, A. F. and A. N. Barclay, "The Immunoglobulin Superfamily—Domains for Cell Surface Recognition," *Ann. Rev. Immunol.* 6:381–405 (1988).
Anderson, D.C., et al., "Leukocyte LFA–1, OKM1, p150,95 Deficiency Syndrome: Functional and Biosynthetic Studies of Three Kindreds," *Fed. Proceedings* 44(10):2671–2677 (Jul. 1985).

*Primary Examiner*—Prema Mertz
*Attorney, Agent, or Firm*—Sterne, Kessler, Goldstein & Fox P.L.L.C.

[57] ABSTRACT

The present invention relates to intercellular adhesion molecules (ICAM-3) which is involved in the process through which lymphocytes recognize and migrate to sites of inflammation as well as attach to cellular substrates during inflammation. The invention is directed toward such molecules, screening assays for identifying such molecules and antibodies capable of binding such molecules. The invention also includes therapeutic and diagnostic uses for adhesion molecules and for the antibodies that are capable of binding them.

28 Claims, 26 Drawing Sheets

OTHER PUBLICATIONS

Anderson, D.C., et al., "The Severe and Moderate Phenotypes of Heritable Mac–1, LFA–1 Deficiency: Their Quantitative Definition and Relation to Leukocyte Dysfunction and Clinical Features," *J. Infect. Dis.* 152(4):668–689 (Oct. 1985).

Bagnasco, M., et al., "Functional Involvement of the LFA–1/ICAM–1 Adhesion System in the Autologous Mixed Lymphocyte Reaction," *Cell. Immunol.* 128(2):362–369 (Jul. 1990).

Barnes, P.J., et al., "The Effect of Airway Epithelium on Smooth Muscle Contractility in Bovine Trachea," *Brit. J. Pharmacol.* 86:685–691 (1985).

Campanero, M.R., et al., "ICAM–3 Interacts with LFA–1 and Regulates the LFA–1/ICAM–1 Cell Adhesion Pathway," *J. Cell Biol.* 123(4):1007–1016 (Nov. 1993).

Christiansen, S.C., et al., "Detection of Tissue Kallikrein in the Bronchoalveolar Lavage Fluid of Asthmatic Subjects," *J. Clin. Invest.* 79:188–197 (Jan. 1987).

Cosimi, A.B., et al., "In Vivo Effects of Monoclonal Antibody To ICAM–1 (CD54) In Nonhuman Primates With Renal Allografts," *J. Immunol.* 144(12):4604–4612 (Jun. 15, 1990).

Davignon, D., et al., "Lymphocyte function–associated antigen 1 (LFA–1): A surface antigen distinct from Lyt–2,3 that participates in T lymphocyte–mediated killing," *Proc. Natl. Acad. Sci. USA* 78:4535–4539 (Jul. 1981).

de Fougerolles, A.R., et al., "Characterization of ICAM–2 and Evidence for a Third Counter–Receptor for LFA–1," *J. Exp. Med.* 174:253–267 (Jul. 1991).

de Fougerolles, A.R., et al., "Intercellular Adhesion Molecule 3, a Third Adhesion Counter–Receptor for Lymphocyte Function–Associated Molecule 1 on Resting Lymphocytes," *J. Exp. Med.* 175:185–190 (Jan. 1992).

Dransfield, I., et al., "Early Events of the Immune Response Mediated by Leukocyte Integrins," *Immunol. Rev.* 114:29–44 (Apr. 1990).

Dustin, M.L., et al., "Induction by IL 1 and Interferon–γ: Tissue Distribution, Biochemistry, and Function of a Natural Adherence Molecule (ICAM–1)," *J. Immunol.* 137(1):245–254 (1986).

Dustin, M.L., and Springer, T.A., "Lymphocyte Function–associated Antigen–1 (LFA–1) Interaction with Intercellular Adhesion Molecule–1 (ICAM–1) is One of At Least Three Mechanisms for Lymphocyte Adhesion to Cultured Endothelial Cells," *J. Cell Biol.* 107:321–331 (1988).

Dustin, M.L., et al., "Adhesion of T–Lymphoblasts to Epidermal Keratinocytes is Regulated by Interferon γ and is Mediated by Intercellular Adhesion Molecule 1 (ICAM–1)," *J. Exp. Med.* 167:1323–1340 (1988).

Dustin, M.L., et al., "Supergene Families Meet in the Immune System," *Immunol. Today* 9(7&8):213–215 (1988).

Dustin, M.L., et al., "Structure and Regulation of the Leukocyte Adhesion Receptor LFA–1 and Its Counterreceptors, ICAM–1 and ICAM–2," *Cold Spring Harbor Symp. Quant. Biol.* 54(2):753–765 (1989).

Dustin, M.L., et al., "T–cell Receptor Cross–linking Transiently Stimulates Adhesiveness Through LFA–1," *Nature* 341:619–624 (Oct. 19, 1989).

Eisen, H.W., "The Origins of Immunology", in: *Microbiology*, 3rd ed., Philadelphia: Harper & Row, pp. 290–295 (1980).

Eisen, H.W., "The Cellular Basis for Immune Responses," in: *Microbiology*, 3rd ed., Philadelphia: Harper & Row, pp. 381–418 (1980).

Fawcett, J., et al., "Molecular Cloning of ICAM–3, a Third Ligand for LFA–1, Constitutively Expressed on Resting Leukocytes," *Nature* 360:481–484 (Dec. 3, 1992).

Fischer, A., et al., "Role of the LFA–1 Molecule in Cellular Interactions Required for Antibody Production in Humans," *J. Immunol.* 136(9):3198–3203 (1986).

Flavahan, N.A., et al., "Respiratory Epithelium Inhibits Bronchial Smooth Muscle Tone," *J. Appl. Physiol.* 58:834–838 (1985).

Flavin, T., et al., "Monoclonal Antibodies Against Intercellular Adhesion Molecule 1 Prolong Cardiac Allograft Survival in Cynomolgus Monkeys," *Transplant. Proc.* 23(1):533–534 (Feb. 1991).

Frigas, E., et al., "The Eosinophil and the Pathophysiology of Asthma," *J. Allergy Clin. Immunol.* 77(4):527–537 (Apr. 1986).

Gartner, S., et al., "The Role of Mononuclear Phagocytes in HTLV–III/LAV Infection," *Science* 233:215–219 (Jul. 11, 1986).

Goddard, P., et al., "Functional Assessment of Alveolar Macrophages: Comparison of Cells From Asthmatics and Normal Subjects," *J. Allergy Clin. Immunol.* 70(2):88–93 (Aug. 1982).

Hamann, A., et al., "Evidence for an Accessory Role of LFA–1 in Lymphocyte–High Endothelium Interaction During Homing," *J. Immunol.* 140(3):693–699 (1988).

Hildreth, J.E.K., et al., "Involvement of a Leukocyte Adhesion Receptor (LFA–1) in HIV–Induced Syncytium Formation," *Science* 244:1075–1078 (Jun. 2, 1989).

Johnson, R.T., et al., "The Neurobiology of Human Immunodeficiency Virus Infections," *FASEB J.* 2:2970–2981 (Nov. 1988).

Juan, M., et al., "CDw50 and ICAM–3: Two Names for the Same Molecule," *Eur. J. Immunol.* 23:1508–1512 (1993).

Keizer, G.D., et al., "Biochemical and Functional Characteristics of the Human Leukocyte Membrane Antigen Family LFA–1, Mo–1 and p150,95," *Eur. J. Immunol.* 15:1142–1147 (1985).

Kishimoto, T.K., et al., "Leukocyte Adhesion Deficiency. Aberrant Splicing of a Conserved Integrin Sequence Causes a Moderate Deficiency Phenotype," *J. Biol. Chem.* 264(6):3588–3595 (1989).

Kishimoto, T.K., et al., "The Leukocyte Integrins," *Adv. Immunol.* 46:149–182 (1989).

Knapp, et al., *Fourth International Workshop & Conference on Hist. DIA*.

Kohl, S., et al., "Defective Natural Killer Cytotoxicity and Polymorphonuclear Leukocyte Antibody–Dependent Cellular Cytotoxicity in Patients with LFA–1/OKM–1 Deficiency," *J. Immunol.* 133(6):2972–2978 (1984).

Krensky, A.M., et al., "LFA–1, LFA–2, and LFA–3 Antigens are Involved in CTL–Target Conjugation," *J. Immunol.* 132(5):2180–2182 (1984).

Makgoba, M.W., et al., "Functional Evidence That Intercellular Adhesion Molecule–1 (ICAM–1) is a Ligand for LFA–1–dependent Adhesion in T Cell–mediated Cytotoxicity," *Eur. J. Immunol.* 18:637–640 (1988).

Makgoba, M.W., et al., "ICAM–1, a Ligand for LFA–1–Dependent Adhesion of B, T and Myeloid Cells," *Nature* 331:86–88 (1988).

Makgoba, M.W., et al., "The CD2–LFA–3 and LFA–1–ICAM Pathways: Relevance to T–cell Recognition," *Immunol. Today* 10:417–422 (1989).

Marlin, S.D., et al., "Purified Intercellular Adhesion Molecule–1 (ICAM–1) Is a Ligand for Lymphocyte Function–Associated Antigen 1 (LFA–1)," *Cell* 51:813–819 (Dec. 4, 1987).

Pals, S.T., et al., "Evidence that Leukocyte Function–Associated Antigen–1 is Involved in Recirculation and Homing of Human Lymphocytes via High Endothelial Venules," *J. Immunol.* 140(6):1851–1853 (1988).

Patarroyo, M., et al., "Identification of a Cell–Surface Glycoprotein Mediating Adhesion in Human Granulocytes," *Scand. J. Immunol.* 22:619–631 (1985).

Rice, G.E., et al., "Inducible Cell Adhesion Molecule 110 (INCAM–110) is an Endothelial Receptor for Lymphocytes. A CD11/CD18–independent Adhesion Mechanism," *J. Exp. Med.* 171(4):1369–1374 (Apr. 1, 1990).

Rossen, R.D., et al., "HIV–1–Stimulated Expression of CD11/CD18 Integrins and ICAM–1: A Possible Mechanism for Extravascular Dissemination of HIV–1–Infected Cells," *Trans. Assoc. Amer. Physicians* 102:117–130 (1989).

Rothlein, R., and Springer, T.A., "The Requirement for Lymphocyte Function–Associated Antigen 1 in Homotypic Leukocyte Adhesion Stimulated by Phorbol Ester," *J. Exp. Med.* 163:1132–1149 (1986).

Rothlein, R., et al., "A Human Intercellular Adhesion Molecule (ICAM–1) Distinct from LFA–1," *J. Immunol.* 137(4):1270–1274 (1986).

Sanchez–Madrid, F., et al., "A Human Leukocyte Differentiation Antigen Family with Distinct α–Subunits and a Common β–Subunit," *J. Exp. Med.* 158:1785–1803 (Dec. 1983).

Sanchez–Madrid, F., et al., "Three Distinct Antigens Associated with Human T–Lymphocyte–mediated Cytolysis: LFA–1, LFA–2, and LFA–3," *Proc. Natl. Acad. Sci. USA* 79:7489–7493 (1982).

Schnittman, S.M., et al., "Characterization of gp120 Binding to CD4 and an Assay that Measures Ability of Sera to Inhibit This Binding," *J. Immunol.* 141(12):4181–4186 (Dec. 15, 1988).

Seed, B., et al., "Molecular Cloning of the CD2 Antigen, the T–Cell Erythrocyte Receptor, by a Rapid Immunoselection Procedure," *Proc. Natl. Acad. Sci. USA* 84:3365–3369 (May 1987).

Simmons, D., et al., "ICAM, an Adhesion Ligand of LFA–1, is Homologous to the Neural Cell Adhesion Molecule NCAM," *Nature* 331:624–627 (1988).

Smith, C.W., et al., "Recognition of an Endothelial Determinant for CD18–dependent Human Neutrophil Adherence and Transendothelial Migration," *J. Clin. Invest.* 82:1746–1756 (1988).

Springer T., et al., "Mac–1: a Macrophage Differentiation Antigen Identified by Monoclonal Antibody," *Eur. J. Immunol.* 9:301–306 (1979).

Springer, T.A., et al., "LFA–1 and Lyt–2,3, Molecules Associated with T Lymphocyte–Mediated Killing; and Mac–1, an LFA–1 Homologue Associated with Complement Receptor Function," *Immunol. Rev.* 68:171–195 (1982).

Springer, T.A., "The LFA–1, Mac–1 Glycoprotein Family and its Deficiency in an Inherited Disease," *Fed. Proc.* 44(10):2660–2663 (Jul. 1985).

Springer, T.A., et al., "The Lymphocyte Function–Associated LFA–1, CD2, and LFA–3 Molecules: Cell Adhesion Receptors of the Immune System," *Ann. Rev. Immunol.* 5:223–252 (1987).

Staunton, D.E., et al., "Primary Structure of ICAM–1 Demonstrates Interaction between Members of the Immunoglobulin and Integrin Supergene Families," *Cell* 52:925–933 (1988).

Stoler, M.H., et al., "Human T–Cell Lymphotropic Virus Type III Infection of the Central Nervous System," *J. Am. Med. Assoc.* 256(17):2360–2364 (Nov. 7, 1986).

Strassman, G., et al., "Mechanisms of Tumor Cell Capture by Activated Macrophages: Evidence for Involvement of Lymphocyte Function–Associated (LFA)–1 Antigen" *J. Immunol.* 136(11):4328–4333 (1986).

Valentin, A., et al., "The Leukocyte Adhesion Glycoprotein CD18 Participates in HIV–1–Induced Syncytia Formation in Monocytoid and T Cells," *J. Immunol.* 144(3):934–937 (Feb. 1, 1990).

Vazeux, R., et al., "Cloning and Characterization of a New Intercellular Adhesion Molecule, ICAM–R," *Nature* 360:485–488 (Dec. 3, 1992).

Vilella, R., et al., "Involvement of the CDw50 Molecule in Allorecognition," *Tissue Antigens* 36(5):203–210 (Nov. 1990).

Wawryk, S.O., et al., "The Role of the LFA–1/ICAM–1 Interaction in Human Leukocyte Homing and Adhesion," *Immunol. Rev.* 108:135–161 (1989).

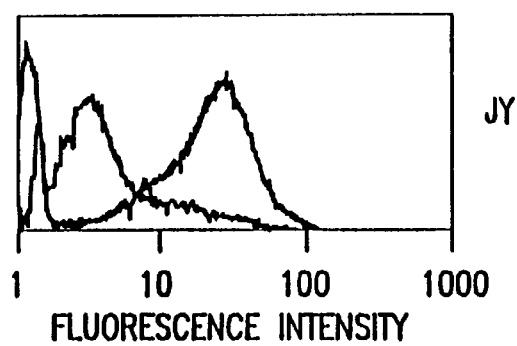
FIG.2A(1)
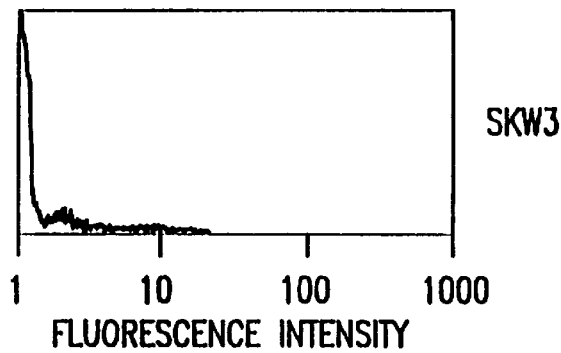
FIG.2A(2)
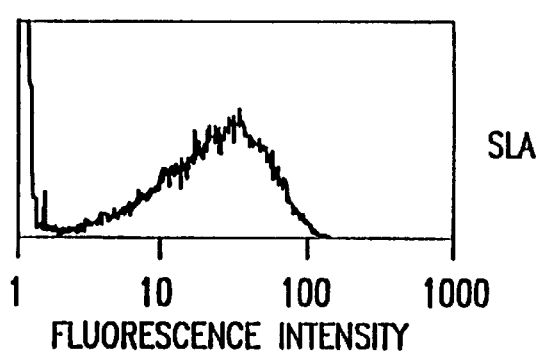
FIG.2A(3)
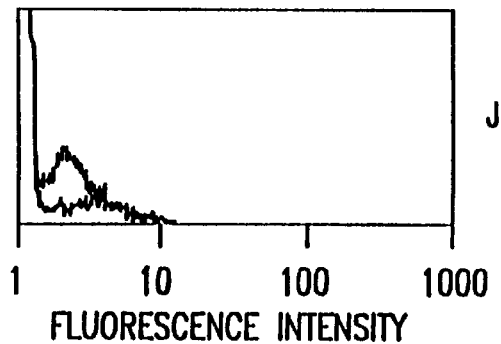
FIG.2A(4)

FIG.2A(5) ICAM-2 JY
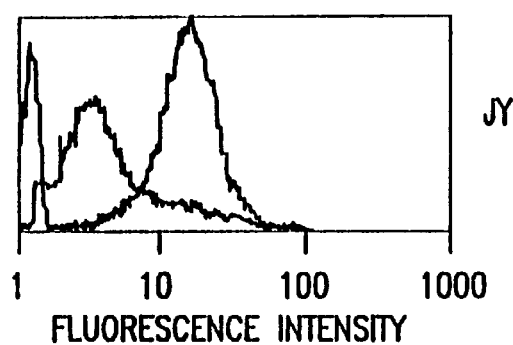
FIG.2A(6) SKW3
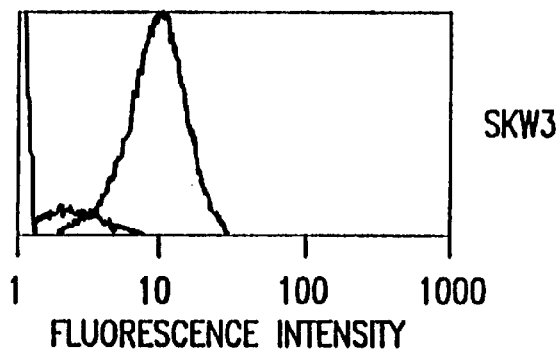
FIG.2A(7) SLA
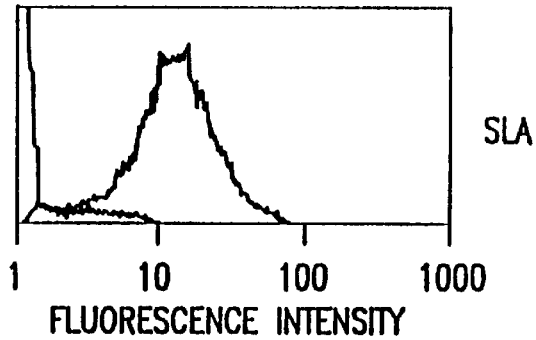
FIG.2A(8) JURKAT
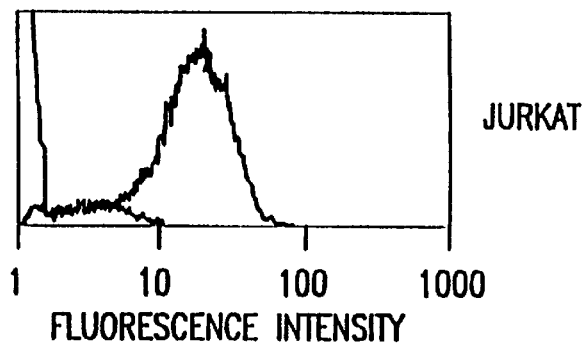

FIG.2A(9) ICAM-3
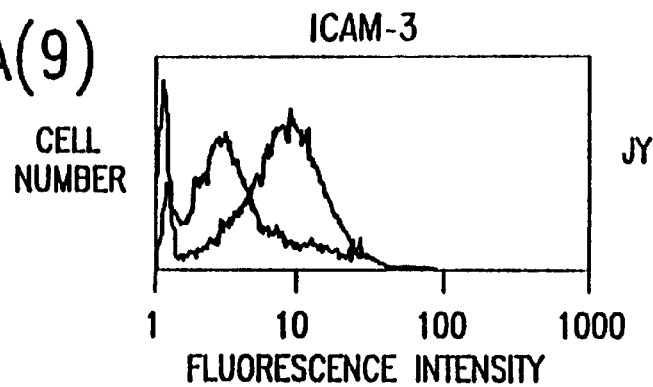
FIG.2A(10)
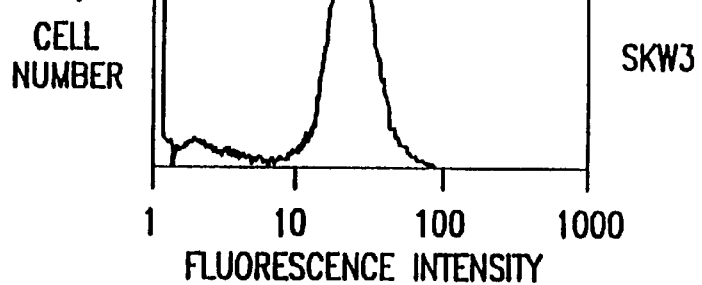
FIG.2A(11)
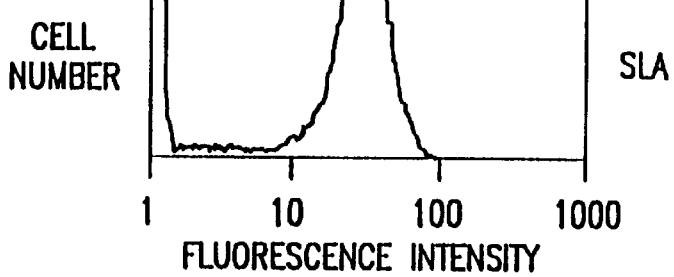
FIG.2A(12)
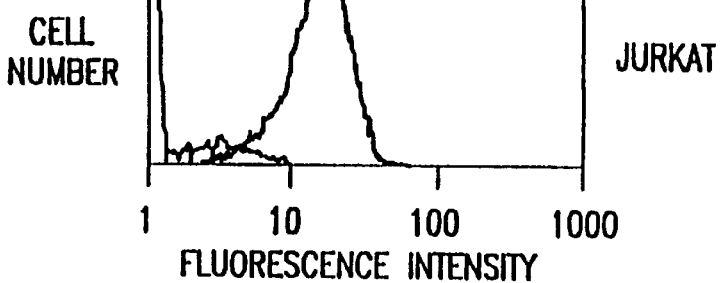

FIG.2B(1) 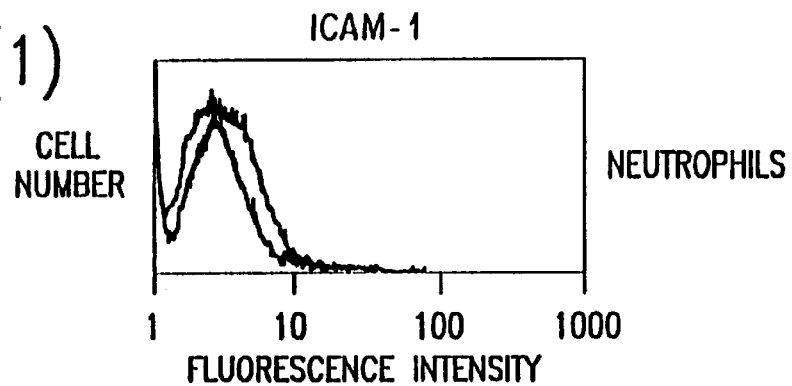
FIG.2B(2) 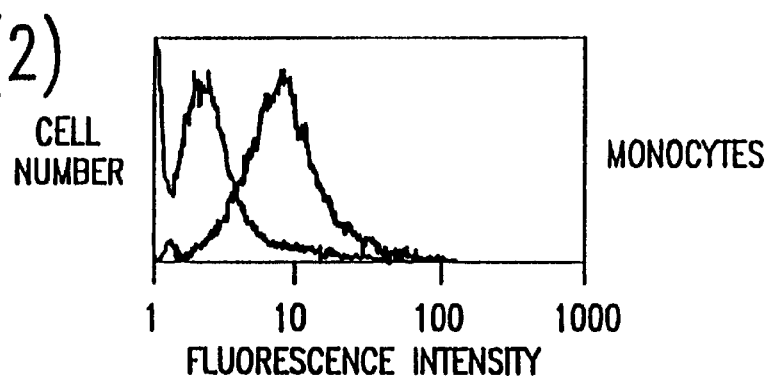
FIG.2B(3) 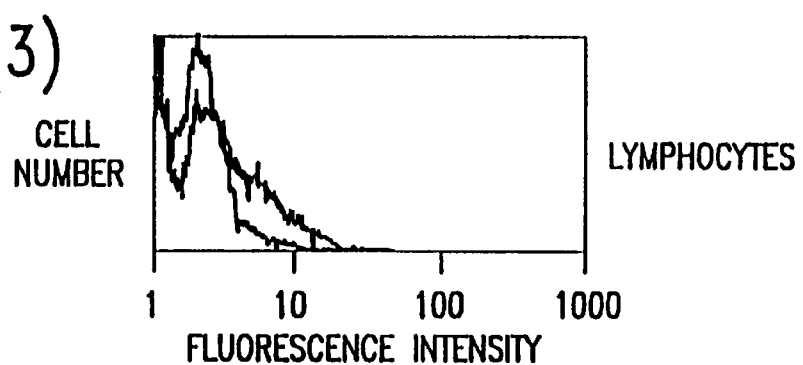
FIG.2B(4) 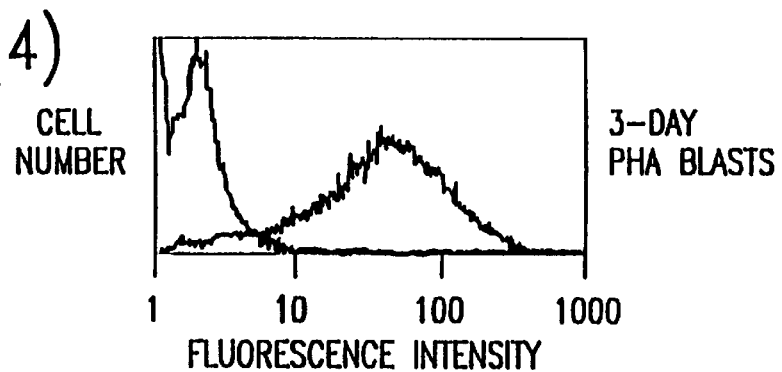

FIG.2B(5)
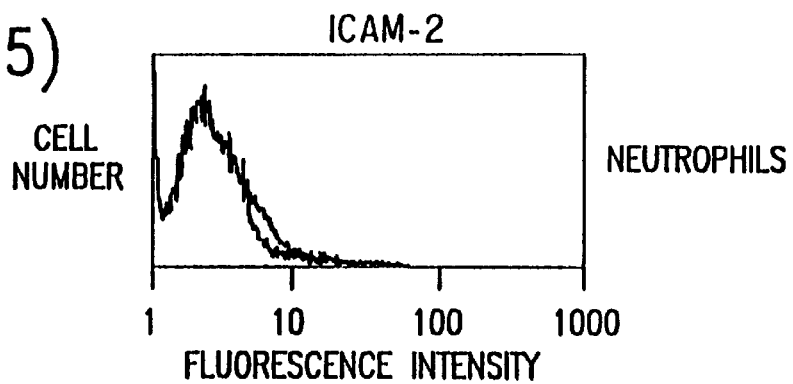
FIG.2B(6)
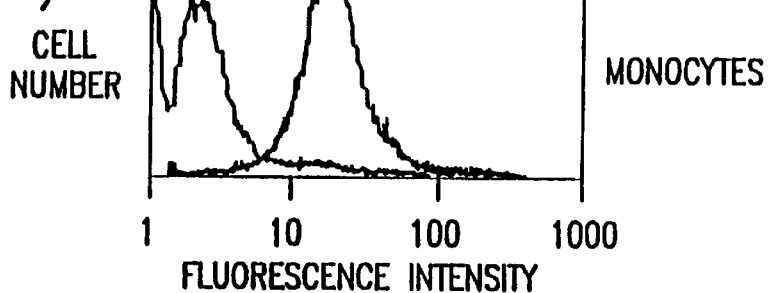
FIG.2B(7)
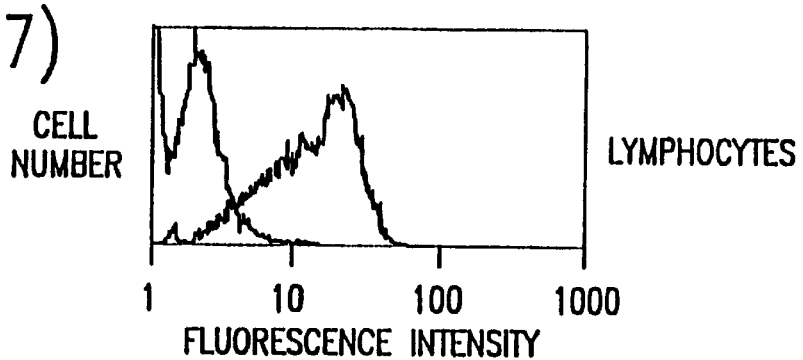
FIG.2B(8)
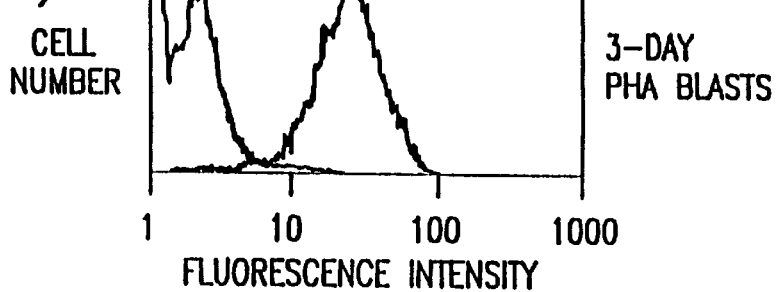

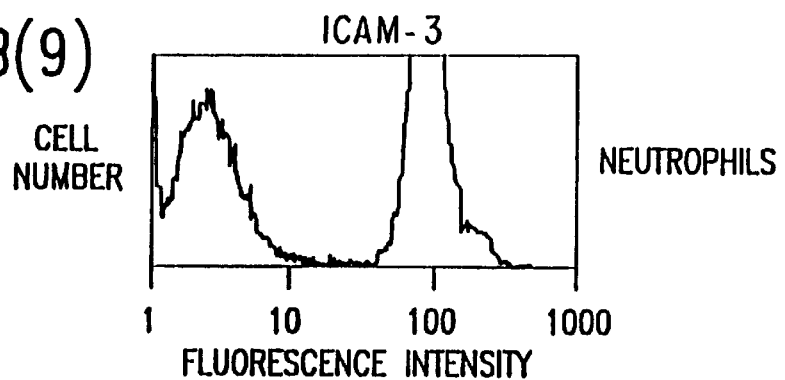
FIG.2B(9) — ICAM-3 — NEUTROPHILS
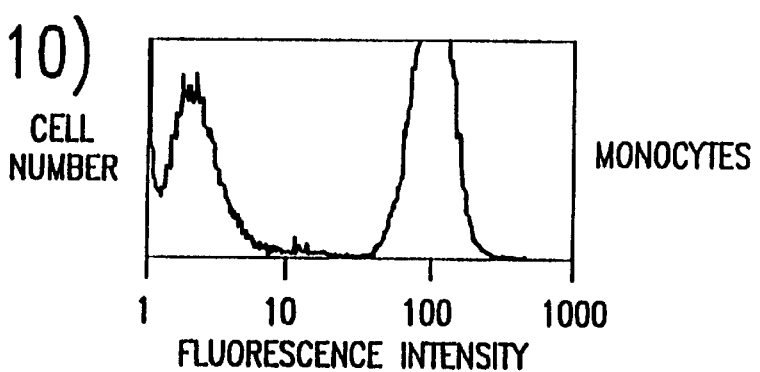
FIG.2B(10) — MONOCYTES
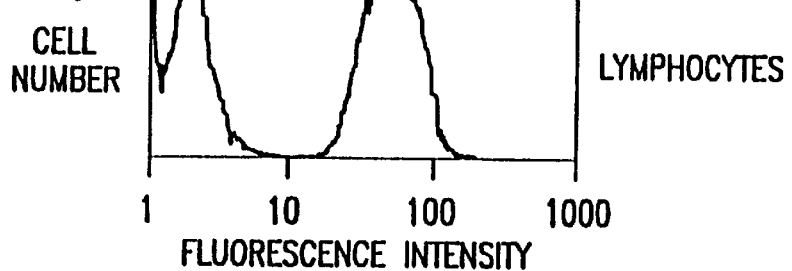
FIG.2B(11) — LYMPHOCYTES
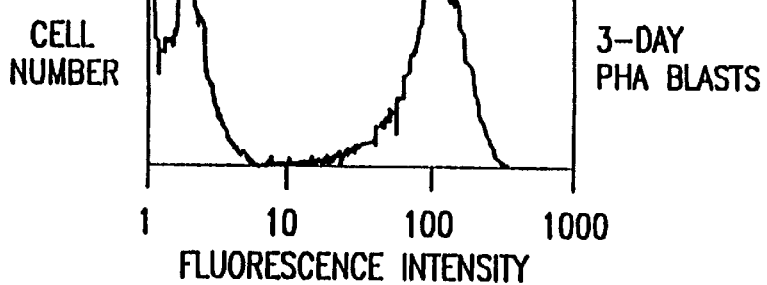
FIG.2B(12) — 3-DAY PHA BLASTS

```
301 TLQTVTIYSEPAPNVILTKPEVSEGTEVTVKCEAHPRAKVTLNGVPAQPL 350
        .  |..|||.| | :|..|||:||||.:
  1 ................PLRGSTVTVSCMAGARVQVTLDGVPAAAP 29

351 GPRAQLLLKATPEDNGRSFSCSATLEVAGQLIHKNQTRELRVLYGPRLDE 400
    |..||| |.||..|:|||| |||||||  ||::: 
 30 GQPAQLQLNATESDDGRSFFCSATLEVHGQFLQ................. 62
```

FIG.13

```
  1 ................................TRQ 3
                                     ||:
401 RDCPGNWTWPENSQQTPMCQAWGNPLPELKCLKDGTFPLPIGESVTVTRD 450

4 I........HPGRGDGHLRLGAPTLSPVFVAVLLTLGVVTIVLAL....M 41
       :     .  |: :  ...|||  : |::|......... ...
451 LEGTYLCRARSTQGEVTREVTVNVLSPRYEIVIITVVAAAVIMGTAGLST 500

42 YVFREHQRSGSYHVR................. 56
    |::  :   |::
501 YLYNRQRKIKKYRLQQAQKGTPMKPNTQATPP 532
```

FIG.14

```
  1 .................TRQIHPGRGDGHLRLG.......... 16
                     | . ::|:|||  ::
151 RGNETLHYETFGKAAPAPQEATATFNSTADREDGHRNFSCLAVLDLMSRG 200

17 ........APTLSPVF.............VAVLLTLGVVTIVLALMYVF 44
            ||.: ..:              |.|||.| |...::|.::::
201 GNIFHKHSAPKMLEIYEPVSDSQMVIIVTVVSVLLSLFVTSVLLCFIFGQ 250

45 R.EHQRSGSYHVR........... 56
    :  :|| |.| ||.
251 HLRQQRMGTYGVRAAWRRLPQAFRP 275
```

FIG.15

```
  1 ..........EFLL...........RVEPQNPVLSAGGSLFVNCST 27
              ..|.              .|.| ...:|. |||::|.|||
  1 MAPSSPRPALPALLVLLGALFPGPGNAQTSVSPSKVILPRGGSVLVTCST 50

28 DCPSSEKIALETSLSK.ELVASGMGW.................. 52
    .|. ...:::||.|.| ||: .| .:
 51 SCDQPKLLGIETPLPKKELLLPGNNRKVYELSNVQEDSQPMCYSNCPDGQ 100
```

FIG.16

```
  1 .....................EFLLRVEPQNPVLSAGGSLFVNCST 27
                         . | ::| |.. ..:  ||| |||||
  1 MSSFGYRTLTVALFTLICCPGSDEKVFEVHVRPKKLAVEPKGSLEVNCST 50

28 DCPSSEKIALETSLSKELVASGMGW............. 52
    .| .| :|||||.| |:... .|
 51 TCNQPEVGGLETSLNKILLDEQAQWKHYLVSNISHDTVLQCHFTCSGKQE 100
```

FIG.17

```
     GGAGTTCCTTTTGCGGGTGGAGCCCCAGAACCCTGTGCTCTCTGCTGGAGGGTCCCTGTT
 8   --+---------+---------+---------+---------+---------+-------  67
     CCTCAAGGAAAACGCCCACCTCGGGGTCTTGGGACACGAGAGACGACCTCCCAGGGACAA

E  F  L  R  V  E  P  Q  N  P  V  L  S  A  G  G  S  L  F   -

TGTGAACTGCAGTACTGATTGTCCCAGCTCTGAGAAAATCGCCTTGGAGACGTCCCTATC
 68  --+---------+---------+---------+---------+---------+-------  127
     ACACTTGACGTCATGACTAACAGGGTCGAGACTCTTTTAGCGGAACCTCTGCAGGGATAG

V  N  C  S  T  D  C  P  S  S  E  K  I  A  L  E  T  S  L  S  -

AAAGGAGCTGGTGGCCAGTGGCATGGGCTGGG
128  --+---------+---------+---------  159
     TTTCCTCGACCACCGGTCACCGTACCCGACCC

```
     CCCATTGAGGGGTTCCACAGTGACCGTGAGTTGCATGGCTGGGGCTCGAGTCCAGGTCAC
 1   ------+---------+---------+---------+---------+---------+   60
     GGGTAACTCCCCAAGGTGTCACTGGCACTCAACGTACCGACCCCGAGCTCAGGTCCAGTG

P  L  R  G  S  T  V  T  V  S  C  M  A  G  A  R  V  Q  V  T  -

GCTGGACGGAGTTCCGGCCGCGGCCCCGGGGCAGCCAGCTCAACTTCAGCTAAATGCTAC
 61  ------+---------+---------+---------+---------+---------+   120
     CGACCTGCCTCAAGGCCGGCGCCGGGGCCCCGTCGGTCGAGTTGAAGTCGATTTACGATG

L  D  G  V  P  A  A  A  P  G  Q  P  A  Q  L  Q  L  N  A  T  -

CGAGAGTGACGACGGACGCAGCTTCTTCTGCAGTGCCACTCTCGAGGTGCACGGCCAGTT
 21  ------+---------+---------+---------+---------+---------+   180
     GCTCTCACTGCTGCCTGCGTCGAAGAAGACGTCACGGTGAGAGCTCCACGTGCCGGTCAA

E  S  D  D  G  R  S  F  F  C  S  A  T  L  E  V  H  G  Q  F  -

CTTGCAGAG
181  ---------  189
     GAACGTCTC

```
     ACTTTGTCCCCGGTCTTCGTGGCGGTGTTACTGACCCTGGGCGTGGTGACTATCGTACTG
 54  ------+---------+---------+---------+---------+---------+---  113
     TGAAACAGGGGCCAGAAGCACCGCCACAATGACTGGGACCCGCACCACTGATAGCATGAC

T  L  S  P  V  F  V  A  V  L  L  T  L  G  V  V  T  I  V  L  -

GCCTTAATGTACGTCTTCAGGGAGCACCAACGGAGCGGCAGTTACCATGTTAG
114  ------+---------+---------+---------+---------+------  166
     CGGAATTACATGCAGAAGTCCCTCGTGGTTGCCTCGCCGTCAATGGTACAATC

```
1000 CAGTGACCGTGAGTGCATGGCTGGGCCTCCAGTGACGGACTCCAAGGTCCGGCTGACGGAGTTCCGGCCCCGGGGCAGCCAGCTCAACTTCAGCTAAATGCTACCGAGAGTG  1110
303   V  T  V  S  C  M  A  G  A  R  V  Q  V  T  L  D  G  V  P  A  A  A  P  G  Q  P  A  Q  L  N  [N  A  T]  E  S  D   339

1111 ACGAGGACGCAGCTTCTCTGCAGTGCCACTCTCGAGGTGGACGGCGAGTTCTTGCACGAGAACAGTAGGCGTCCAGCGGAACACTCTGCCAGTTCTTGCACAGAAGCGTCCAGTCCTGTATGGTCCAAAATTGACCGAC  1221
340   D  G  R  S  F  F  C  S  A  T  L  E  V  D  G  E  F  L  H  R  [N  S  S]  V  Q  L  R  V  L  Y  G  P  K  I  D  R  A   376

1222 CCACATGCCCCACCACTTGAAATGGAAAGATAAAACGAGACACTCTCGAGTGCAAGCTCCAAGCCAGGGCAACCCTACCCCGAGCTGGGGTGTTTGAAGGAAGGCTCCAGCC  1332
377   T  C  P  Q  H  L  K  W  K  D  K  T  R  H  V  L  Q  C  Q  A  R  G  N  P  Y  P  E  L  R  C  L  K  E  G  S  S  R   413

1333 GGGAGGTGCCGTGGGAGTCCCGGATCCCGTTCTTCGTCAACGCTAACACATAATGTACTTATCAGTGCCAAGCTCCAGTCAGGAGGCAAATACACCCTGGTCGTGGTGATGGACA  1443
414   E  V  P  V  G  I  P  F  F  V  [N  V  T]  H  N  G  T  Y  Q  C  Q  A  S  S  S  R  G  K  Y  T  L  V  V  V  M  D  I   450

1444 TTGAGGCTGGGAGCTCCCACTTTGTCCCCGTCTTCGTGGCGGTGTTACTGGCCCTGGGGTGTATAGTCCTTAATGTACGTCTTCAGGAGCACCAACCGATCTCTTCAGGACCGA  1554
451   E  A  G  S  S  H  F  V  P  V  F  V  A  V  L  L  T  L  G  V  V  T  I  V  L  A  L  M  Y  V  F  R  E  H  Q  R  S   487

1555 GCCGGCAGTTACCATGTTAGGGAGGAGAGCACCTATCTGCCCCTCACGTCTATGCAGCCGACAGAAGCAATGGGGGAAGAACCGTCCAGAGCTGAGTGACCGCTGGGATCCGG  1665
488   G  S  Y  H  V  R  E  E  S  T  Y  L  P  L  T  S  M  Q  P  T  E  A  M  G  E  E  P  S  R  A  E  *   518

1666 GATCAAAGTTGGCGGGGGCTTGGCTGTGCCTCAGATTCCGCACCAATAAAGCCTTCAAACTCCCT(A)86   1817
```

FIG. 19B

METHODS OF USING INTERCELLULAR ADHESION MOLECULE-3 (ICAM-3), ANTIBODIES THERETO, AND SOLUBLE FRAGMENTS THEREOF

This Application is a divisional application of application Ser. No. 08/038,990 filed on Dec. 23, 1992 now abandoned, which is a continuation-in-part of PCT Application No. US92/04896 filed Jun. 11, 1992, which is a continuation-in-part of U.S. patent application Ser. No. 07/712,879 (filed Jun. 11, 1991) now abandoned and is related to U.S. patent application Ser. Nos. 07/045,963 (filed on May 4, 1987) now abandoned, 07/115,798 (filed on Nov. 2, 1987) now abandoned, 07/155,943 (filed on Feb. 16, 1988) now abandoned, 07/189,815 (filed on May 3, 1988) now abandoned, and 07/250,446 (filed on Sep. 28, 1988) now abandoned, 07/454,294 (filed on Dec. 22, 1989) now abandoned, and PCT Application Nos. PCT/US91/102942 and PCT/US91/02946 (filed at the U.S. Receiving Office on Apr. 27, 1991), which applications are incorporated herein by reference.

BACKGROUND OF THE INVENTION

CROSS-REFERENCE TO RELATED APPLICATIONS

1. Field of the Invention

The present invention relates to the discovery of a new intercellular adhesion molecule, designated ICAM-3 which is involved in the process through which populations of leukocytes recognize and adhere to cellular substrates. ICAM-3 mediates cellular interactions with other lymphocytes, macrophages and neutrophils at the sites of inflammation and sites of immune responses.

The present invention further relates to the use of ICAM-3, alone or in combination with ICAM-1 and/or ICAM-2, to inhibit intercellular adhesion of cells of granulocyte, lymphocyte, or macrophage lineage. The use of such molecules provides a method for the treatment of specific and non-specific inflammation.

The invention also relates to therapeutic and prophylactic methods for suppressing the infection of leukocytes with HIV, and particularly with HIV-1, in an individual who is exposed to HIV or infected by HIV through the administration of ICAM-3, alone or in combination with ICAM-1 and/or ICAM-2. It therefore provides a therapy for diseases, such as AIDS (Acquired Immunodeficiency Syndrome) which are caused by the HIV virus.

The invention also relates to a therapeutic method for suppressing the migration of HIV-1 infected cells from the circulatory system using ICAM-3, alone or in combination with ICAM-1 and/or ICAM-2. It therefore provides a therapy for diseases, such as AIDS (Acquired Immunodeficiency Syndrome) which are caused by the HIV-1 virus.

The invention also relates to a therapeutic method for suppressing T-cell death and "syncytia" formation in an individual infected with HIV using ICAM-3, alone or in combination with ICAM-1 and/or ICAM-2. It therefore provides a therapy for diseases, such as AIDS (Acquired Immunodeficiency Syndrome) which are caused by the HIV-1 virus.

The present invention relates to the use of ICAM-3, alone or in combination with ICAM-1 and/or ICAM-2, in the treatment of asthma.

The present invention additionally relates to molecules capable of binding to ICAM-3 (hereinafter anti-ICAM-3). The binding of an anti-ICAM-3 molecule to ICAM-3 is intended to modulate the biological functions associated with ICAM-3. The binding molecules of the present invention can be an antibody, a peptide, or a carbohydrate which is capable of binding to ICAM-3. Such binding molecules are useful in modulating the biological functions of ICAM-3.

The present invention also relates to the use of a anti-ICAM-3, alone or in combination with anti-ICAM-1 and/or anti-ICAM-2, to inhibit intercellular adhesion of cells of granulocyte, lymphocyte, or macrophage lineage. The use of such molecules provides a method for the treatment of specific and non-specific inflammation.

The invention also relates to therapeutic and prophylactic methods for suppressing the infection of leukocytes with HIV, and particularly with HIV-1, in an individual who is exposed to HIV or infected with HIV through the administration of a anti-ICAM-3, alone or in combination with anti-ICAM-1 and/or anti-ICAM-2. It therefore provides a therapy for diseases, such as AIDS (Acquired Immunodeficiency Syndrome) which are caused by the HIV virus.

The invention also relates to a therapeutic method for suppressing the migration of HIV-1 infected cells from the circulatory system using an anti-ICAM-3 agent, alone or in combination with anti-ICAM-1 and/or anti-ICAM-2 agent. It therefore provides a therapy for diseases, such as AIDS (Acquired Immunodeficiency Syndrome) which are caused by the HIV-1 virus.

The present invention further relates to the use of an anti-ICAM-3 agent, alone or in combination with anti-ICAM-1 and/or anti-ICAM-2, in the treatment of asthma.

2. Description of the Related Art

A. Leukocyte Attachment and Functions

Leukocytes must be able to attach to cellular substrates in order to properly defend the host against foreign invaders such as bacteria or viruses, see Eisen, H. W., (In: *Microbiology*, 3rd Ed., Harper & Row, Philadelphia, Pa. (1980), pp. 290–295 and 381–418) for a review of these functions. Leukocytes must be able to attach to endothelial cells so that they can migrate from the circulatory system to sites of inflammation. Furthermore, they must attach to antigen-presenting cells so that a normal specific immune response can occur, and finally, they must attach to appropriate target cells so that lysis of virally-infected or tumor cells can occur.

Recently, leukocyte surface molecules involved in mediating the above attachment mediated functions were identified using hybridoma technology. Briefly, monoclonal antibodies directed against human T-cells (Davignon, D. et al., *Proc. Natl. Acad. Sci. USA* 78:4535–4539 (1981)) and mouse spleen cells (Springer, T. et al. *Eur. J. Immunol.* 9:301–306 (1979)) were identified which bound to leukocyte surfaces and inhibited the attachment related functions described above (Springer, T. et al., *Fed. Proc.* 44:2660–2663 (1985)). The molecules identified by those antibodies were called Mac-1 and Lymphocyte Function-associated Antigen-1 (LFA-1). Mac-1 is a heterodimer found on macrophages, granulocytes and large granular lymphocytes. LFA-1 is a heterodimer found on most lymphocytes (Springer, T. A. et al. *Immunol. Rev.* 68:111–135 (1982)). These two molecules, plus a third molecule, p150,95 (which has a tissue distribution similar to Mac-1) play a role in cellular adhesion (Keizer, G. et al., *Eur. J. Immunol.* 15:1142–1147 (1985)).

The above-described leukocyte molecules were found to be members of a related family of glycoproteins (Sanchez- Madrid, F. et al., *J. Exper. Med.* 158:1785–1803 (1983); Keizer, G. D. et al., *Eur. J. Immunol.* 15:1142–1147 (1985)), termed the "CD-18 family" of glycoproteins. This glycoprotein family is composed of heterodimers having one alpha chain and one beta chain. Although the alpha chain of each of the antigens differed from one another, the beta chain was found to be highly conserved (Sanchez-Madrid, F. et al., *J. Exper. Med.* 158:1785–1803 (1983)). The beta chain of the glycoprotein family (sometimes referred to as "CD18") was found to have a molecular weight of 95 kd whereas the alpha chains were found to vary from 150 kd to 180 kd (Springer, T., *Fed. Proc.* 44:2660–2663 (1985)). Although the alpha subunits of the membrane proteins do not share the extensive homology shared by the beta subunits, close analysis of the alpha subunits of the glycoproteins has revealed that there are substantial similarities between them. Reviews of the similarities between the alpha and beta subunits of the LFA-1 related glycoproteins are provided by Sanchez-Madrid, F. et al., (*J. Exper. Med.* 158:586–602 (1983); *J. Exper. Med.* 158:1785–1803 (1983)).

A group of individuals has been identified who are unable to express normal amounts of any member of this adhesion protein family on their leukocyte cell surface (Anderson, D. C. et al., *Fed. Proc.* 44:2671–2677 (1985); Anderson, D. C. et al., *J. Infect. Dis.* 152:668–689 (1985)). Such individuals are said to suffer from "leukocyte adherence deficiency disease" ("LAD") (Anderson, D. C., et al., *Fed. Proc.* 44:2671–2677 (1985); Anderson, D. C., et al., *J. Infect. Dis.* 152:668–689 (1985)). Characteristic features of LAD patients include necrotic soft tissue lesions, impaired pus formation and wound healing, as well as abnormalities of adhesion-dependent leukocyte functions in vitro, and susceptibility to chronic and recurring bacterial infections. Granulocytes from these LAD patients behave in the same defective manner in vitro as do their normal counterparts in the presence of anti-CD18 monoclonal antibody. That is, they are unable to perform adhesion related functions such as aggregation or attachment to endothelial cells. More importantly, however, is the observation that these patients are unable to mount a normal inflammatory response because of the inability of their granulocytes to attach to cellular substrates. Most remarkable is the observation that granulocytes from these LAD patients are unable to get to sites of inflammation such as skin infections due to their inability to attach to the endothelial cells in the blood vessels near the inflammation lesions. Such attachment is a necessary step for extravasation.

Lymphocytes from these patients displayed in vitro defects similar to normal counterparts whose CD-18 family of molecules had been antagonized by antibodies. Furthermore, these individuals were unable to mount a normal immune response due to an inability of their cells to adhere to cellular substrates (Anderson, D. C. et al., *Fed. Proc.* 44:2671–2677 (1985); Anderson, D. C. et al.,*J. Infect. Dis.* 152:668–689 (1985)). These data show that immune reactions are mitigated when lymphocytes are unable to adhere in a normal fashion due to the lack of functional adhesion molecules of the CD-18 family.

Thus, in summary, the ability of leukocytes to maintain the health and viability of an animal requires that they be capable of adhering to other cells (such as endothelial cells). This adherence has been found to require cell-cell contact which involves specific receptor molecules present on the cell surface of the leukocytes. These receptors enable a leukocyte to adhere to other leukocytes, to endothelial cells, and other non-vascular cells. The cell surface receptor molecules, LFA-1, Mac-1 and p150,95, have been found to be highly related to one another. Humans whose leukocytes lack these cell surface receptor molecules exhibit chronic and recurring infections, as well as other clinical symptoms including defective antibody responses.

Additionally, since leukocyte adhesion is involved in the process through which foreign tissue is identified and rejected, an understanding of this process is of significant value in the fields of solid organ transplantation such as kidney, non-solid organ transplantation such as bone marrow, tissue grafting, allergy and oncology.

B. Infection with HIV

HIV infection is the cause of AIDS. Many variants of HIV have been described: the major two are HIV-1 and HIV-2. HIV-1 is prevalent in North America and Europe and HIV-2 is prevalent only in Africa. The viruses have similar structures and encode proteins having similar function. HIV infection is believed to occur via the binding of a viral protein (termed "gp120") to a receptor molecule (termed "CD4") present on the surface of T4 ("T helper") lymphocytes (Schnittman, S. M. et al., *J. Immunol.* 141:4181–4186 (1988), which reference is incorporated herein by reference). After binding this receptor, the virus enters the cell and replicates, and in the process, kills the T cell. The destruction of an individual's T4 population is thus a direct result of HIV infection.

The destruction of the T cells results in an impairment in the ability of the infected patient to combat opportunistic infections. Although individuals afflicted with AIDS often develop cancers, the relationship between these cancers and HIV infection is, in most cases, uncertain.

Although the mere replication of the HIV virus is lethal to infected cells, such replication is typically detected in only a small fraction of the T4 cells of an infected individual. Recent results suggest more viremia occurs than had been previously estimated, and the T-cell infection frequency can be as high as 1%.

Several lines of research have elucidated other mechanisms through which the HIV virus mediates the destruction of the T4 population.

Apart from HIV replication, HIV infected cells can be destroyed through the action of cytotoxic, killer cells. Killer cells are normally present in humans, and serve to monitor the host and destroy any foreign cells (such as in mismatched blood transfusions or organ transplants, etc.) which may be encountered. Upon infection with HIV, T4 cells display the gp120 molecule on their cell surfaces. Killer cells recognize such T4 cells as foreign (rather than native cells), and accordingly, mediate their destruction.

HIV infection can also lead to the destruction of non-infected healthy cells. Infected cells can secrete the gp120 protein into the blood system. The free gp120 molecules can then bind to the CD4 receptors of healthy, uninfected cells. Such binding causes the cells to take on the appearance of HIV infected cells. Cytotoxic, killer cells recognize the gp120 bound to the uninfected T4 cells, conclude that the cell is foreign, and mediate the destruction of the cell.

An additional mechanism, and one of special interest to the present invention, with which HIV can cause T4 cell death is through the formation of "syncytia." A "syncytium" is a multinucleated giant cell, formed from the fusion of as many as several hundred T4 cells. Infection with HIV causes the infected cell to gain the ability to fuse with other T4 cells, either HIV infected, or uninfected healthy cells. The syncytium cannot function and soon dies. Its death accomplishes the destruction of both HIV infected and HIV uninfected T4 cells. This process is of special interest to the present invention since it entails the direct cell-cell contact of T4 cells. The ability of HIV-infected cells to form syncytia indicates that such cells acquire a means for fusing with healthy cells.

HIV infection, and especially HIV-1 infection, appears to influence cell surface expression of the leukocyte integrins and cellular adherence reactions mediated by these heterodimers (Petit, A. J., et al., *J. Clin. Invest.* 79:188 (1987); Hildreth, J. E. K., et al., *Science* 244:1075 (1989); Valentin, A., et al., *J. Immunology* 144:934–937 (1990); Rossen, R. D., et al., *Trans. Assoc. American Physicians* 102:117–130 (1989), all of which references are incorporated herein by reference). Following infection with HIV-1, homotypic aggregation of U937 cells is increased, as is cell surface expression of CD18 and CD11b (Petit, A. J., et al., *J. Clin. Invest.* 79:188 (1987)). HIV-1 infected U937 cells adhere to IL-1 stimulated endothelium in greater frequency than uninfected U937 cells; this behavior can be suppressed by treating the infected cells with anti-CD18 or anti-CD11a monoclonal antibodies or by treating endothelial substrates with anti-ICAM-1 antibodies (Rossen, R. D., et al., *Trans. Assoc. American Physicians* 102:117–130 (1989)). Monoclonal antibodies to CD18 or CD11a have also been found to be able to inhibit formation of syncytia involving phytohemagglutinin (PHA)-stimulated lymphoblastoid cells and constitutively infected, CD4-negative T cells (Hildreth, J. E. K., et al., *Science* 244:1075 (1989)). Treatment of only the virus infected cells with anti-CD18, or anti-CD11a monoclonal antibodies was found to have little effect on syncytium formation, suggesting that these antibodies principally protect uninfected target cells from infection (Hildreth, J. E. K., et al., *Science* 244:1075 (1989); Valentin, A., et al., *J. Immunology* 144:934–937 (1990)). Valentin et al. (Valentin, A., et al., *J. Immunology* 144:934–937 (1990)) have recently confirmed these observations by demonstrating that monoclonal antibodies specific for CD18 inhibit syncytia formed when continuous T cell lines are co-cultured with HIV-1 infected U937 cells.

Although the mechanism through which monoclonal antibodies specific for CD18 or CD11a protect susceptible cells from fusing with HIV infected cells remains unknown, and is not necessary to an appreciation of the present invention, studies with radiolabeled gp120 suggest that heterodimers containing CD18 do not provide a binding site for the virus (Valentin, A., et al., *J. Immunology* 144:934–937 (1990)). Thus, HIV infection involves cell-cell interactions, and/or viral-cell interactions which mimic such cell-cell interactions. The cell-cell interactions may result in the transport of cell-free virus or the transport of virus infected cells across endothelial barriers. Viral-cell interactions which mimic the cell-cell interactions may facilitate or enable free virus to attach to and/or infect healthy cells.

The present invention thus derives, in part, from the observation that HIV infection, and particularly HIV-1 infection, results in increased expression of the CD11a/ CD18 heterodimer and its binding ligand. This increased expression is significant in that it enhances the ability of HIV-infected T cells to adhere or aggregate with one another (i.e. to undergo "homotypic aggregation"). Since such homotypic aggregation is not observed to occur among quiescent normal leukocytes, this discovery indicates that the expression of the CD11/CD18 receptors and/or ligands, such as ICAM-1, is required for such aggregation. LFA-1 must bind to ICAM-1 in order for homotypic aggregation to occur. As disclosed herein, ICAM-3 is the only member of the ICAM family of molecules which is expressed at a high level on resting T-cells. Only anti-ICAM-3 antibodies are capable of blocking the adhesion of T-cells to LFA-1 unless the T-cells are "activated". Therefore anti-ICAM-3 antibodies can be used to suppress aggregation of T-cells.

Additionally, anti-ICAM-3 antibodies may be used to block the adhesion processes of infected T-cells which permits HIV-1 to be transmitted from an infected cell to a healthy cell of an individual, and also permits or facilitates infection of healthy cells with free virus.

C. Migration of HIV Infected Cells

The migration and dissemination of leukocytes is important in protecting an individual from the consequences of infection. These processes, however, are also responsible for the migration and dissemination of viral-infected leukocytes. Of particular concern is the migration and dissemination of leukocytes infected with HIV. The migration of such cells results in the formation of extravascular foci, and may cause tumors and other abnormalities.

Histologic examination of affected organs reveals focal extravascular mononuclear cell infiltrates. Attempts to identify virus-infected cells in such infiltrates in the central nervous system have revealed the presence of HIV-1 infected cells. These studies have shown that the HIV-1 virus resides primarily in monocytes and macrophages, and other cells of this lineage (R. T. Johnson, et al. *FASEB J.* 2:2970 (1988); M. H. Stoler et al., *J. Amer. Med. Assn.* 256:2360 (1986); S. Gartner et al. *Science* 233:215 (1986)).

The mechanisms which stimulate formation of extravascular infiltrates of HIV-1-infected monocytoid cells have not previously been well defined. The mechanisms may involve either the transport of cell-free virus or the transport of virus across endothelial barriers within the cytoplasm of infected mononuclear cells.

Since infection with HIV-1 stimulates cell surface expression of molecules which facilitate adherence of leukocytes to vascular endothelial cells and the translocation of leukocytes from the blood to extravascular tissue sites (C. W. Smith et al., *J. Clin. Invest.* 82:1746 (1988), herein incorporated by reference) it has been proposed to use antibodies which inhibit cellular migration to prevent the dissemination of HIV infected cells (WO 90/13316).

D. Asthma: Clinical Characteristics

Asthma is a heterogeneous family of diseases. It is characterized by a hyper-responsiveness of the tracheobronchi to stimuli (Kay, A. B., *Allergy and Inflammation*, Academic Press, NY (1987); which reference is incorporated herein by reference). Clinically, asthma is manifested by the extensive narrowing of the tracheobronchi, by thick tenacious secretions, by paroxysms of dyspnea, coughing, and wheezing. Although the relative contribution of each of these conditions is unknown, the net result is an increase in airway resistance, hyperinflation of the lungs and thorax and abnormal distribution of ventilation and pulmonary blood flow. The disease is manifested in episodic periods of acute symptoms interspersed between symptom-free periods. The acute episodes result in hypoxia, and can be fatal. Approximately 3% of the general world population suffers from asthma.

Two types of asthma have been described: allergic asthma and idiosyncratic asthma. Allergic asthma is usually associated with a heritable allergic disease, such as rhinitis, urticaria, eczema, etc. The condition is characterized by positive wheal-and-flare reactions to intradermal injections of airborne antigens (such as pollen, environmental or occupational pollutants, etc.), and increased serum levels of IgE. The development of allergic asthma appears to be causally related to the presence of IgE antibodies in many patients. Asthma patients who do not exhibit the above-described characteristics are considered to have idiosyncratic asthma.

Allergic asthma is believed to be dependent upon an IgE response controlled by T and B lymphocytes and activated by the interaction of airborne antigen with mast cell-bound pre-formed IgE molecules. The antigenic encounter must occur at concentrations sufficient to lead to IgE production for a prolonged period of time in order to sensitize an individual. Once sensitized, an asthma patient may exhibit symptoms in response to extremely low levels of antigen.

Asthma symptoms may be exacerbated by the presence and amount of the triggering antigen, environmental factors, occupational factors, physical exertion, and emotional stress.

Asthma may be treated with methylxanthines (such as theophylline), beta-adrenergic agonists (such as catecholamines, resorcinols, saligenins, and ephedrine), glucocorticoids (such as hydrocortisone), inhibitors of mast cell degranulation (i.e. chromones such as cromolyn sodium) and anticholinergics (such as atropine).

Asthma is believed to involve an influx of eosinophils ("eosinophilia") into the tissues of the lung (Frigas, E. et al., *J. Allergy Clin. Immunol.* 77:527–537 (1986), which reference is incorporated herein by reference).

Insight into the immunological basis of asthma has been gained from bronchoalveolar lavage studies (Godard, P. et al., *J. Allergy Clin. Immunol.* 70:88 (1982)), and studies of respiratory smooth muscle tissue denuded of epithelium (Flavahan, N. A. et al., *J. Appl. Physiol.* 58:834 (1985); Barnes, P. J. et al., Br. *J. Pharmacol.* 86:685 (1985)). Although these studies have not led to the elucidation of the mechanism underlying the immunology of asthma, they have led to the development of a generally accepted hypothesis concerning the immunological etiology of the disease (see, Frigas, E. et al., *J. Allergy Clin. Immunol.* 77:527–537 (1986)).

The hallmarks of the pathology of asthma are a massive infiltration of the lung parenchyma by eosinophils and the destruction of mucociliary capacity. The "eosinophil hypothesis" suggests that eosinophils are attracted to the bronchus in order to neutralize harmful mediators released by the mast cells of the lung. According to the hypothesis eosinophils are attracted to the bronchi where they degranulate to release cytotoxic molecules. Upon degranulation, eosinophils release enzymes such as histaminase, arylsulfatase and phospholipase D which enzymatically neutralize the harmful mediators of the mast cell. However, these molecules also promote the destruction of the mucociliary apparatus, thus preventing the clearing of the bronchial secretions, and contributing to the lung damage characteristic of asthma.

Since asthma involves the migration of cells, it has been proposed to use antibodies which inhibit this migration to mitigate the effects of allergens in a subject (WO 90/10453).

SUMMARY OF THE INVENTION

The present invention is based on the discovery of a new cellular adhesion molecule, denoted Intercellular Adhesion Molecule-3 (ICAM-3). The invention additionally pertains to functional derivatives of ICAM-3, anti-ICAM-3 antibodies, fragments of said antibodies humanized anti-ICAM-3 antibodies, and other molecules capable of binding to and inhibiting the biological function of ICAM-3.

The invention additionally includes diagnostic and therapeutic uses for all of the above-described molecules.

In detail, the invention includes ICAM-3, or a functional derivative thereof, substantially free of natural contaminants.

The invention provides a method of obtaining a recombinant or synthetic DNA molecule capable of encoding, or expressing ICAM-3, or a functional derivative thereof.

The invention additionally provides an antibody, and especially a monoclonal antibody, capable of binding to a molecule selected from the group consisting of ICAM-3, and a functional derivative of ICAM-3.

The invention also provides a hybridoma cell capable of producing the above-described monoclonal antibody.

The invention includes a method for producing a desired hybridoma cell that produces an antibody which is capable of binding to ICAM-3, or a functional derivative thereof, which comprises the steps:

(a) immunizing an animal with an immunogen selected from the group consisting of: substantially pure ICAM-3, a cell expressing ICAM-3, a membrane of a cell expressing ICAM-3, ICAM-3 bound to a carrier, a peptide fragment of ICAM-3, or a peptide fragment of ICAM-3 bound to a carrier, (b) fusing the spleen cells, isolated from said immunized animal, with a myeloma cell line, (c) permitting the fused spleen and myeloma cells to form antibody secreting hybridoma cells, and (d) screening the hybridoma cells for a hybridoma cell capable of producing an anti-ICAM-3 antibody.

The invention also provides a method for modulating the ICAM-3 mediated biological functions of a cell wherein said method comprises providing to a subject in need of such a treatment an effective amount of an ICAM-3 modulating agent, wherein said ICAM-3 modulating agent is selected from the group consisting of: an antibody capable of binding to ICAM-3; a fragment of said antibody, said fragment being capable of binding to ICAM-3; ICAM-3; a functional derivative of ICAM-3; and a non-immunoglobulin antagonist of ICAM-3 other than ICAM-1, ICAM-2, or a member of the CD-18 family of molecules.

The invention also provides a method of treating specific inflammation in humans, and other mammals, wherein said method comprises providing to a subject in need of such treatment an amount of an anti-inflammatory agent sufficient to suppress the inflammation; wherein the anti-inflammatory agent is selected from the group consisting of: an antibody capable of binding to ICAM-3; a fragment of said antibody; said fragment being capable of binding to ICAM-3; substantially pure ICAM-3; a functional derivative of ICAM-3; or a non-immunoglobulin antagonist of ICAM-3, wherein said inflammation is a result of solid organ transplantation (e.g. kidney), non-solid organ transplantation (e.g. bone marrow) or tissue grafting.

The invention also provides a method for treating non-specific inflammation in humans, and other mammals, wherein said method comprises providing to a subject in need of such treatment an amount of an anti-inflammatory agent sufficient to suppress the inflammation; wherein the anti-inflammatory agent is selected from the group consisting of: an antibody capable of binding to ICAM-3; a fragment of said antibody; said fragment being capable of binding to ICAM-3; substantially pure ICAM-3; a functional derivative of ICAM-3; or a non-immunoglobulin antagonist of ICAM-3.

The invention further includes the above-described method for treating inflammation wherein the inflammation is associated with a condition selected from the group consisting of: adult respiratory distress syndrome; multiple organ injury syndrome secondary to septicemia; multiple organ injury syndrome secondary to septicemia, hemorrhage, or trauma; reperfusion injury of myocardial or other tissues; acute glomerulonephritis; reactive arthritis; dermatosis with acute inflammatory components; acute purulent meningitis or other central nervous system inflammatory disorders, e.g. stroke; thermal injury; hemodialysis; leukapheresis; ulcerative colitis; Crohn's disease; necrotizing enterocolitis; granulocyte transfusion associated syndrome; and cytokine-induced toxicity.

The invention also includes a method of suppressing the metastasis of a hematopoietic tumor cell, the cell utilizing a member of the CD-18 (especially LFA-1) for migration, wherein said method comprises providing to a patient in need of such treatment an amount of an agent sufficient to suppress the metastasis; wherein said agent is selected from the group consisting of: an antibody capable of binding to ICAM-3; a toxin-derivatization of said antibody; a fragment of said antibody, said fragment being capable of binding to ICAM-3; a toxin-derivatization of said fragment; substantially pure ICAM-3; a toxin-derivatized ICAM-3; a functional derivative of ICAM-3; a toxin-derivatization of said functional derivative of ICAM-3; or a non-immunoglobulin antagonist of ICAM-3 other than a member of the CD-18 family of molecules.

The invention also includes a method of suppressing the growth of an ICAM-3-expressing tumor cell wherein said method comprises providing to a patient in need of such treatment an amount of an agent sufficient to suppress the growth, wherein said agent is selected from the group consisting of: an antibody capable of binding to ICAM-3; a toxin-derivatization of said antibody; a fragment of said antibody, said fragment being capable of binding to ICAM-3; a toxin-derivatization of said fragment; a toxin-derivatized member of the CD-18 family of molecules; or a toxin-derivatized functional derivative of a member of the CD-18 family of molecules.

The invention also provides a method for detecting the presence of a cell expressing ICAM-3 wherein said method comprises:

(a) incubating a cell or an extract of a cell in the presence of a nucleic acid molecule, the nucleic acid molecule being capable of hybridizing to ICAM-3 MRNA; and (b) determining whether the nucleic acid molecule has become hybridized to a complementary nucleic acid molecule present in said cell or in said extract of said cell.

The invention also provides a method for detecting the presence of ICAM-3 in a biological fluid sample wherein said method comprises:

(a) incubating said sample with an antibody or fragment thereof which is capable of binding to ICAM-3; and (b) detecting whether said antibody bound said sample.

The invention also provides a pharmaceutical composition comprising:

(a) an agent selected from the group consisting of: an antibody capable of binding to ICAM-3; a fragment of said antibody, said fragment being capable of binding to ICAM-3; substantially pure ICAM-3; a functional derivative of ICAM-3; or a non-immunoglobulin antagonist of ICAM-3 other than a member of the CD-18 family of molecules an immunosuppressive agent.

Figure 1A:
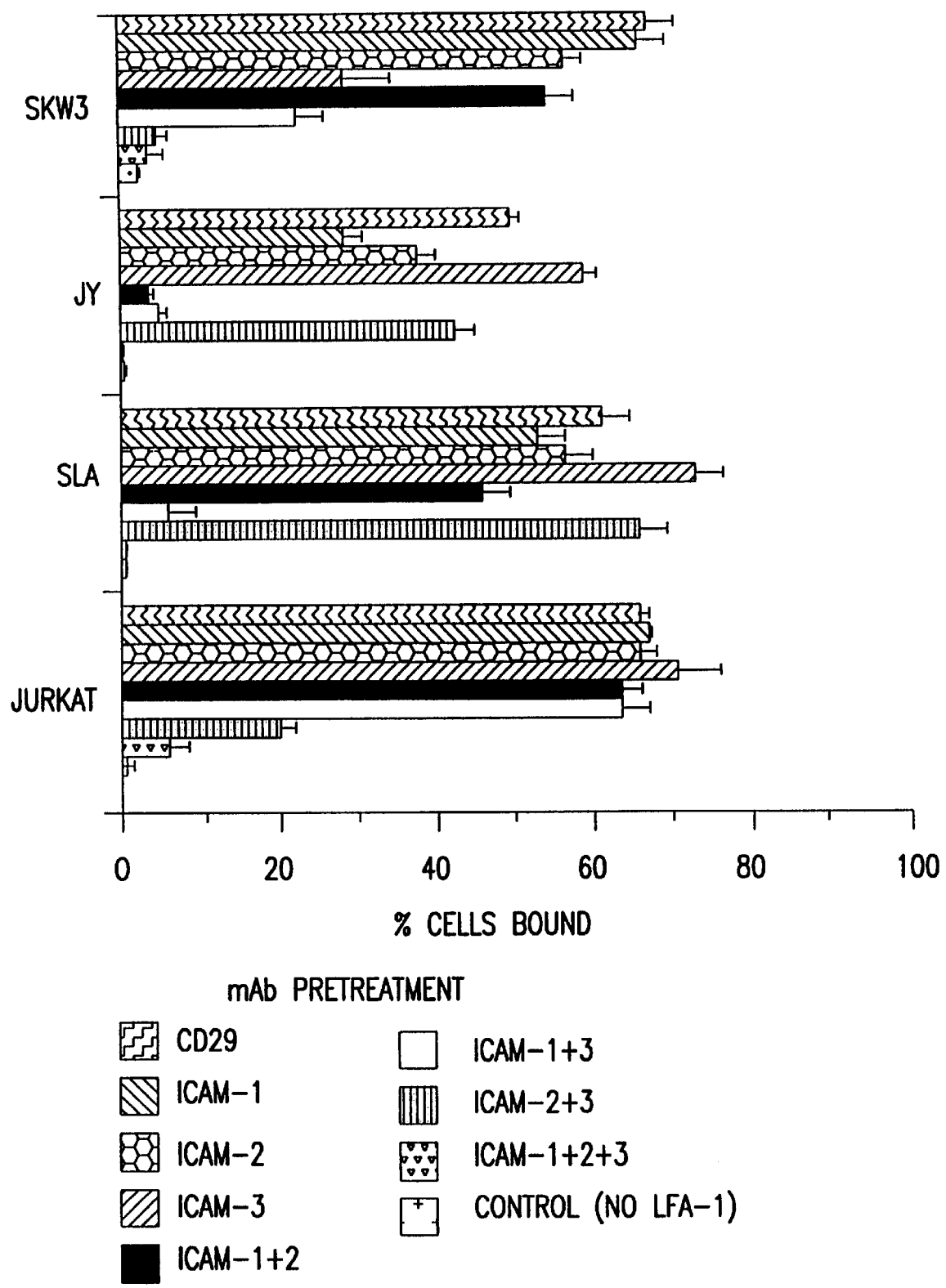
FIGS. 1A and B Adhesion of cell lines to purified LFA-1.

Adhesion of cell lines (FIG. 1A) and lymphocytes (FIG. 1B) to purified LFA-1 is accounted for by ICAM-1, ICAM-2, and ICAM-3. Binding of BCECF-labeled cells on LFA-1-coated microtitre wells in the presence of blocking MAb specific for LFA-1, ICAM-1, ICAM-2, and ICAM-3. Control wells were coated without LFA-1.

FIGS. 2A(1-12) and B(1-12) Flow cytometric analysis of cellular ICAM-1e ICAM-2 and ICAM-3 expression.

(FIG. 2A(1-12)) Lymphoblastoid cell lines were labeled with saturating amounts of either MAb RR1/1 (anti-ICAM-1, MAb CB-IC2/1 (anti-ICAM-2), MAb CBR-IC3/1 (anti-ICAM-3) or non-binding control MAb X63 (thin lines), and then followed by FITC-anti-mouse immunoglobulin. (FIG. 2B(1-12)) Resting human leukocytes and 3 day PHA-activated lymphocytes were analyzed for ICAM expression as above.

Figure 3A:
Figure 3B:
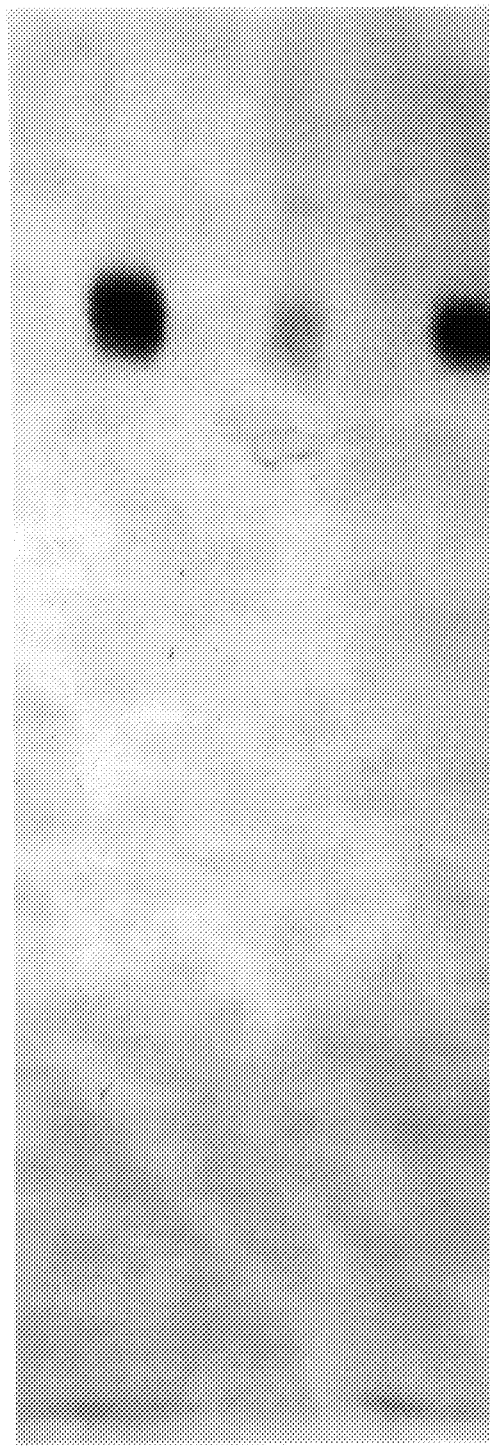
Figure 3C:
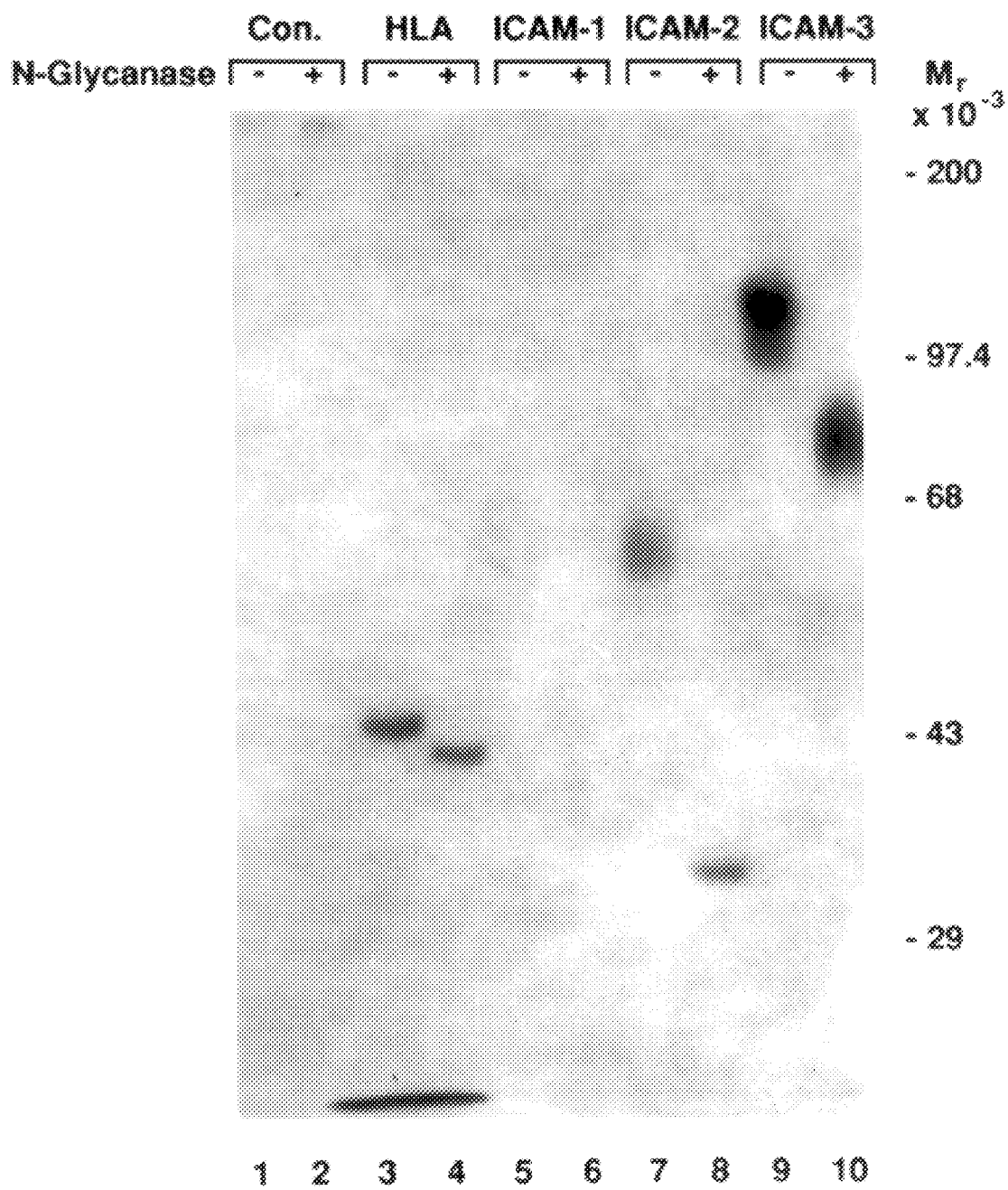

FIGS. 3A, 3B and 3C Immunoprecipitation of ICAM-3.

(FIGS. 3A) and (B) $^{125}$I-labeled cell lysates immunoprecipitated with either non-binding control X63 or MAb CB-IC3/1 (anti-ICAM-3) under reducing and non-reducing condition. FIG. 3(c) $^{125}$I-labeled SKW3 cell lysates treated with (+) or without (-) N-glycanase, and immunoprecipitated with either non-binding control MAb X63, MAb W6/32 (anti-HLA-A, B, C), MAb RR1/1 (anti-ICAM-1), MAb CBR-IC2/1 (anti-ICAM-2), or MAb CB-IC3/1 (anti-ICAM-3).

Figure 4:
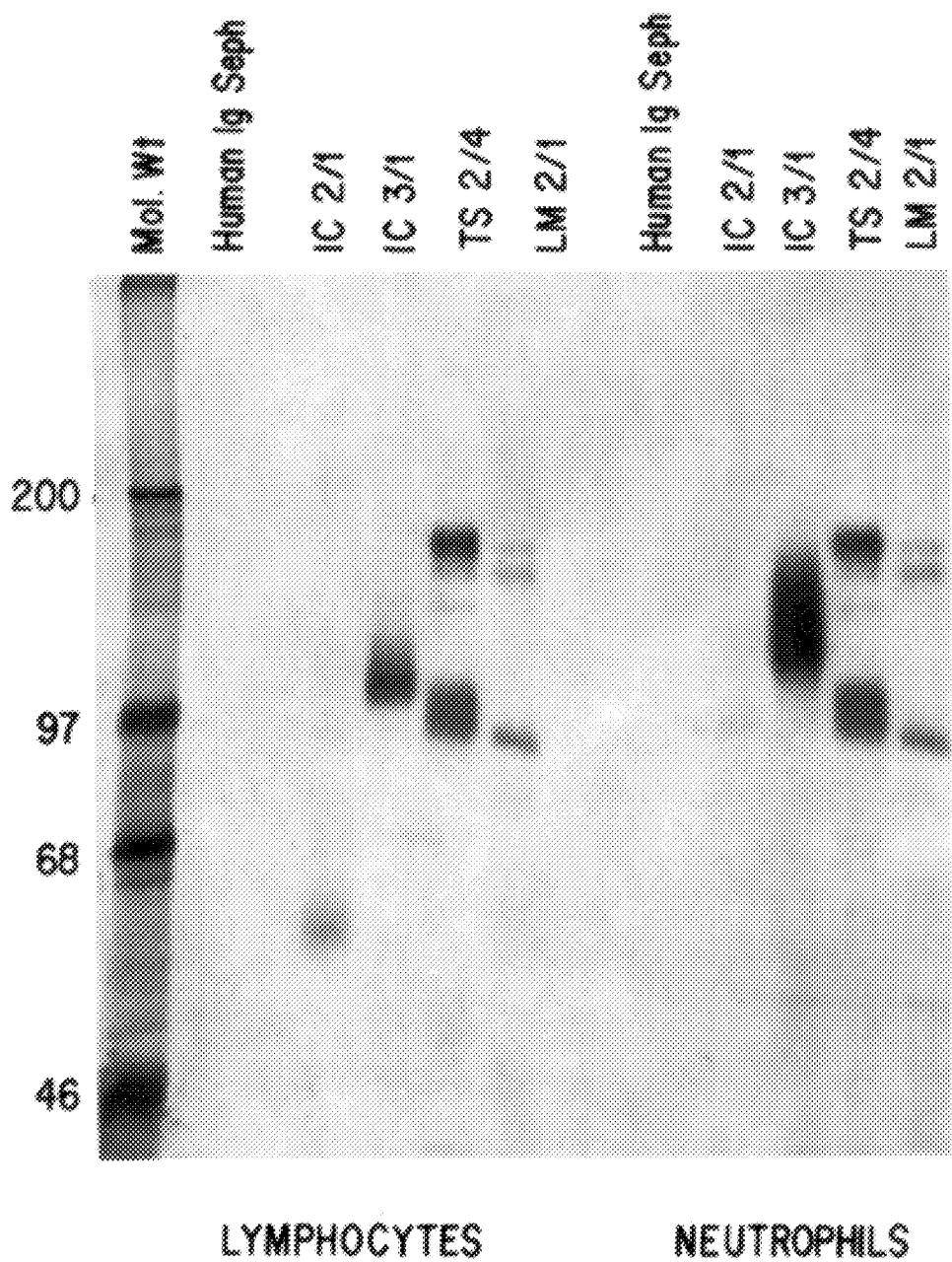

FIG. 4. Immunopecipitation of ICAM-3 from different sources.

ICAM-3 was immunoprecipitated from $I^{125}$ labeled lymphocyte and neutrophil lysates using mAb-coupled Sepharose. The immunoprecipatated ICAM-3 was resolved using polyacrylamide gel electrophoresis. Other mAb were used to immunoprecipitate other cell surface molecules. Human Ig Sepharose (control lane), CBR-IC2/1 (ICAM-2), CBR-IC3/1 (ICAM-3), TS2/4 (LFA-1), LM2/1 (MAC-1).

Figure 5:
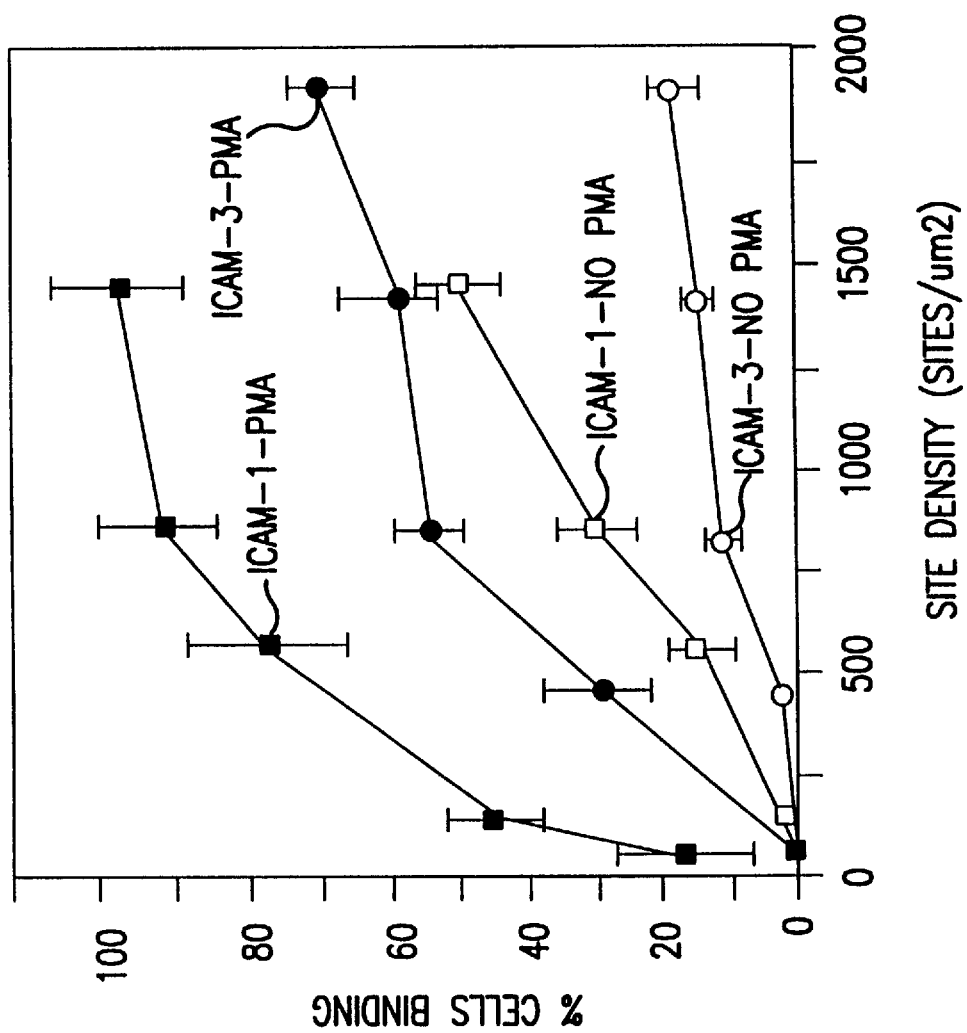

FIG. 5. Effect of PMA on SKW3 binding to ICAM-1 and ICAM-3.

The ability of SKW3 cells to bind to purified ICAM-1 and ICAM-3, and the effects of PMA stimulation of this binding was tested as previously described (Dustin et al., Nature 341:619 (1989); Marlin et al., Cell 51:813–819 (1987)). One representative experiment is shown and error bars indicate one standard deviation (SD).

Figure 6:
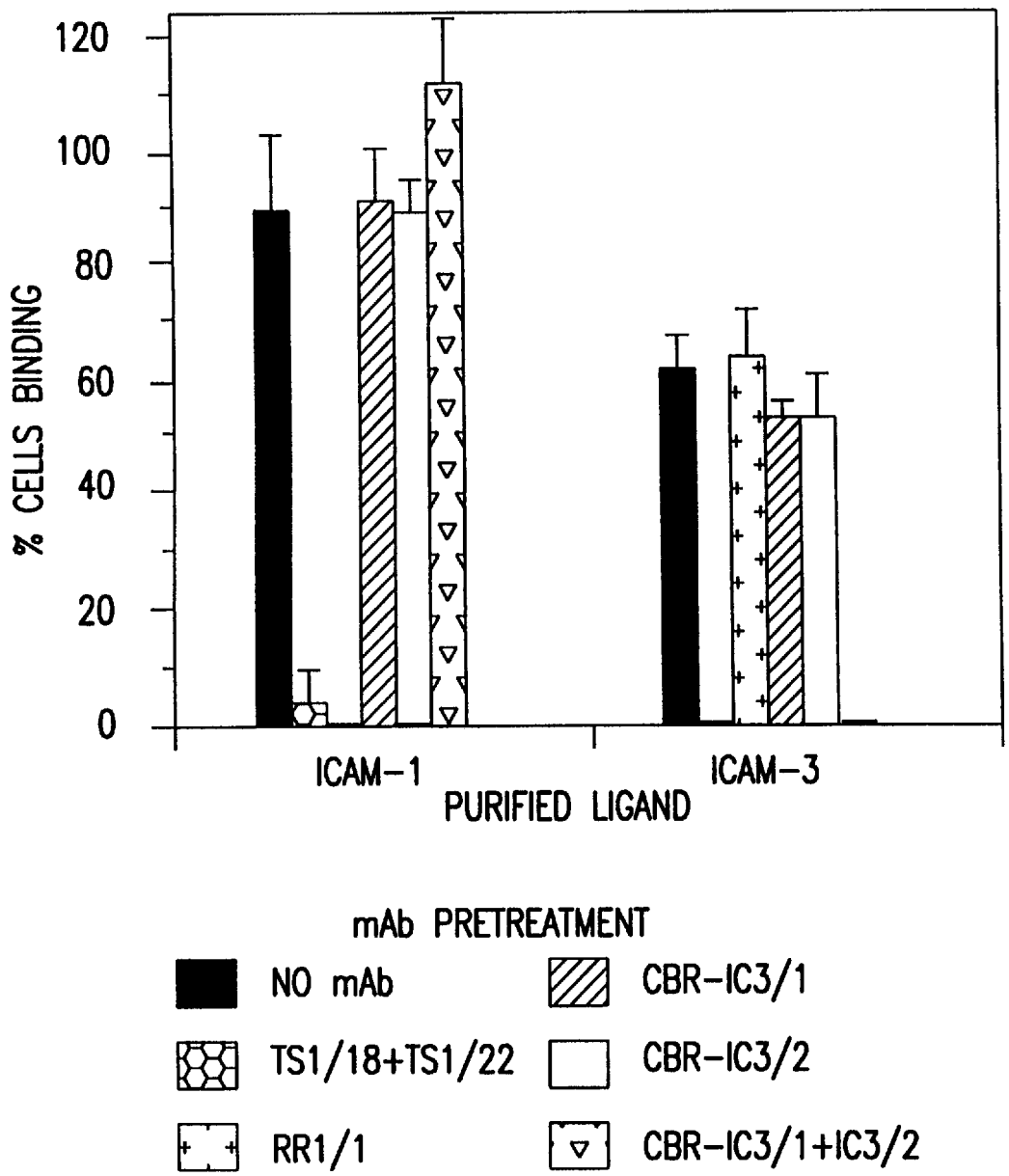

FIG. 6. Antibody blocking of PMA stimulated SKW3 cell adhesion.

Various antibodies were tested for their ability to block PMA stimulated SKW3 cells from binding to purified ICAM-1 or ICAM-3 as previously described. (Dustin et al., Nature 341:619 (1989); Marlin et al., Cell 51:813–819 (1987)). One representative experiment is shown and error bars indicate one SD.

Figure 7:
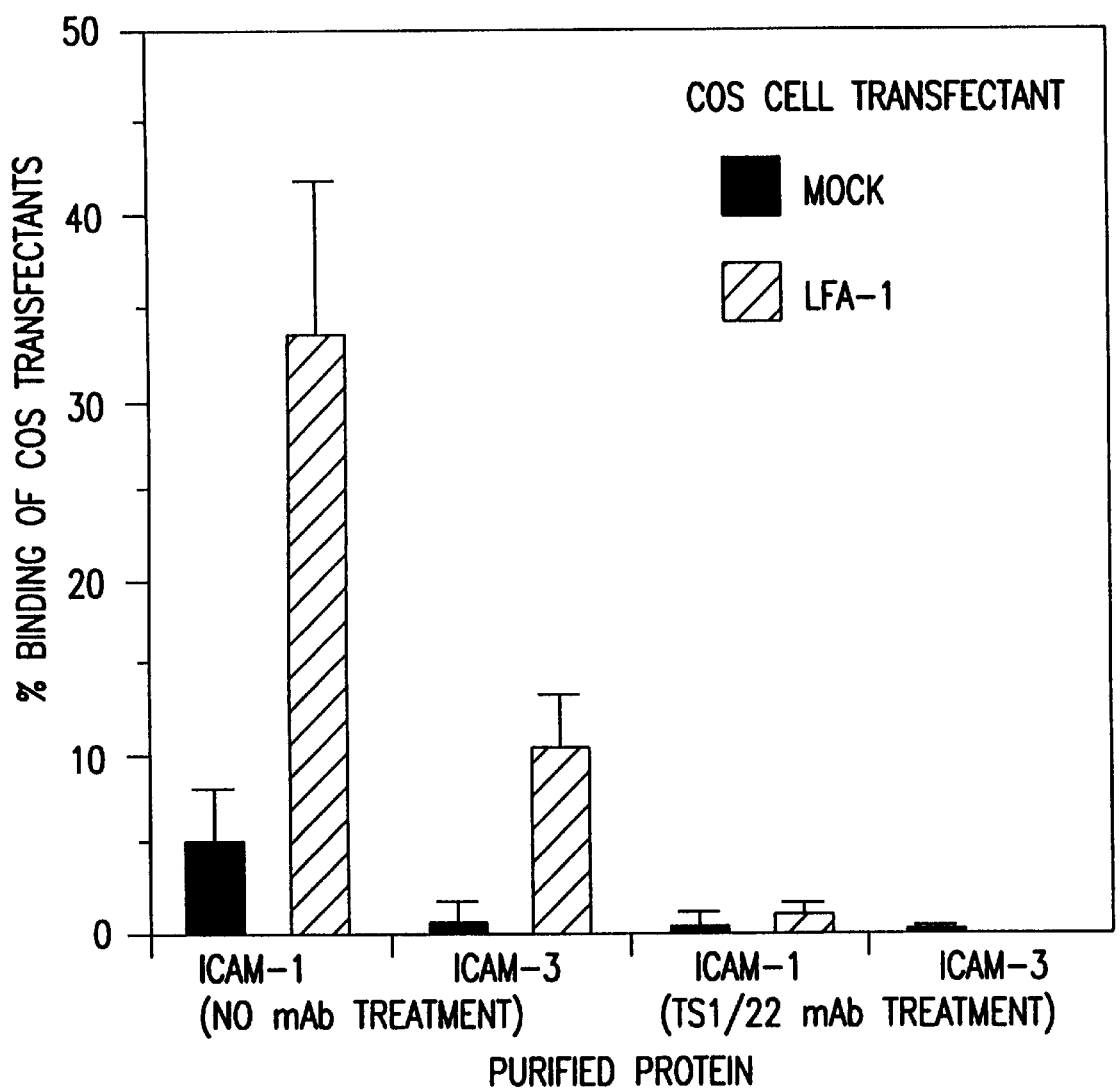

FIG. 7. Binding of COS cell transfectants to purified ICAM's.

COS cells were transfected with an LFA-1 expression vector as previously described (deFougerolles et al., J. Exp. Med. 175:185–190 (1992)). The transfected cells were tested for their ability to bind to immobilized ICAM-1 and ICAM-3 in the presence and absence of an anti-LFA-1 antibody (TS1/22). One representative experiment is shown and error bars indicate one SD.

Figure 8:
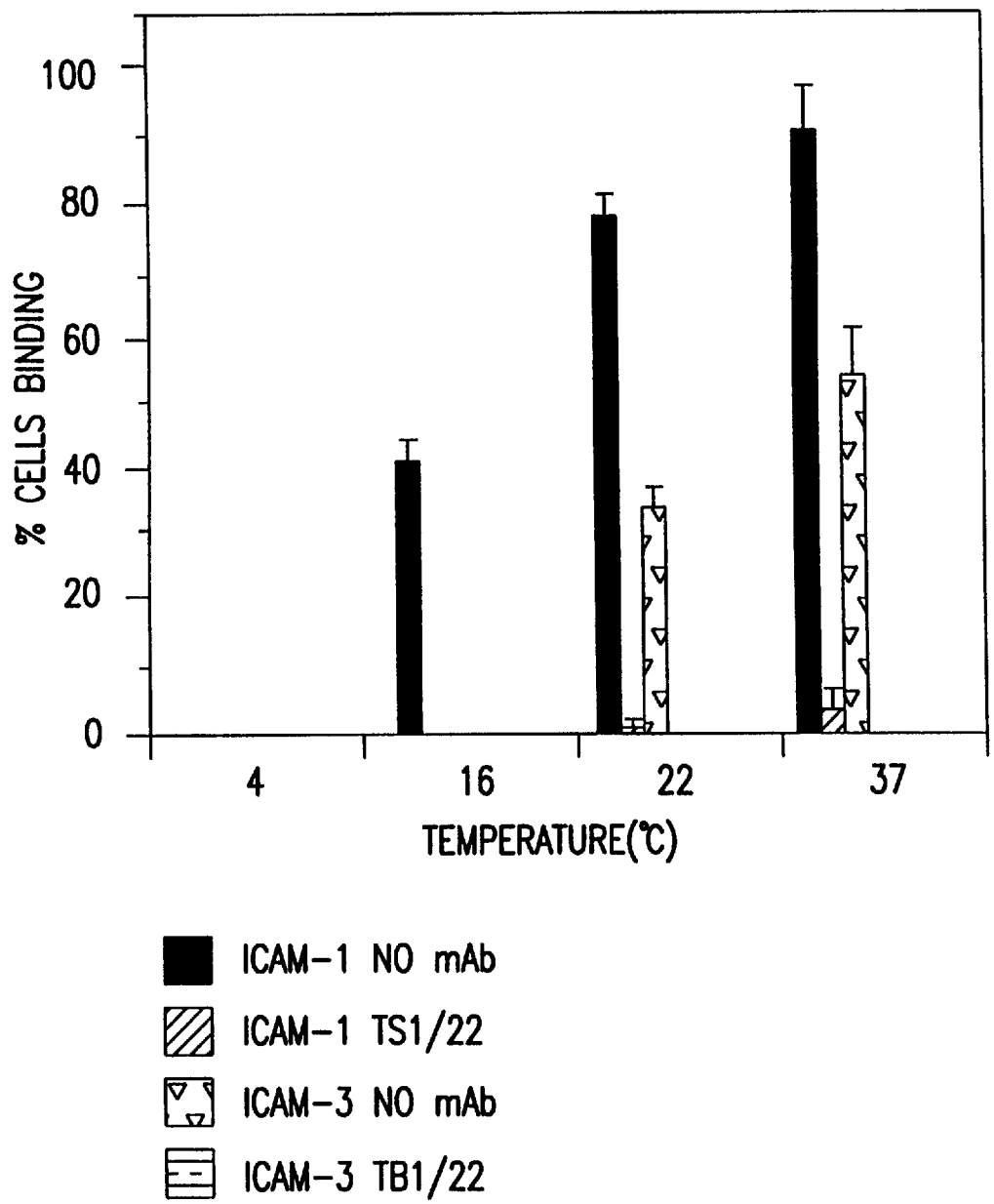

FIG. 8. Temperature dependency of PMA stimulated SKW3 binding to ICAM.

PMA stimulated SKW3 cells ability to bind to purified ICAM-1 and ICAM-3 was tested at 4°, 16°, 22° and 37° C. as previously described. (Marlin et al., *Cell* 51:813–819 (1987)). Assay done in presence or absence of an LFA-1 mAb (TS1/22). One representative experiment is shown and error bars indicate one SD.

Figure 9:
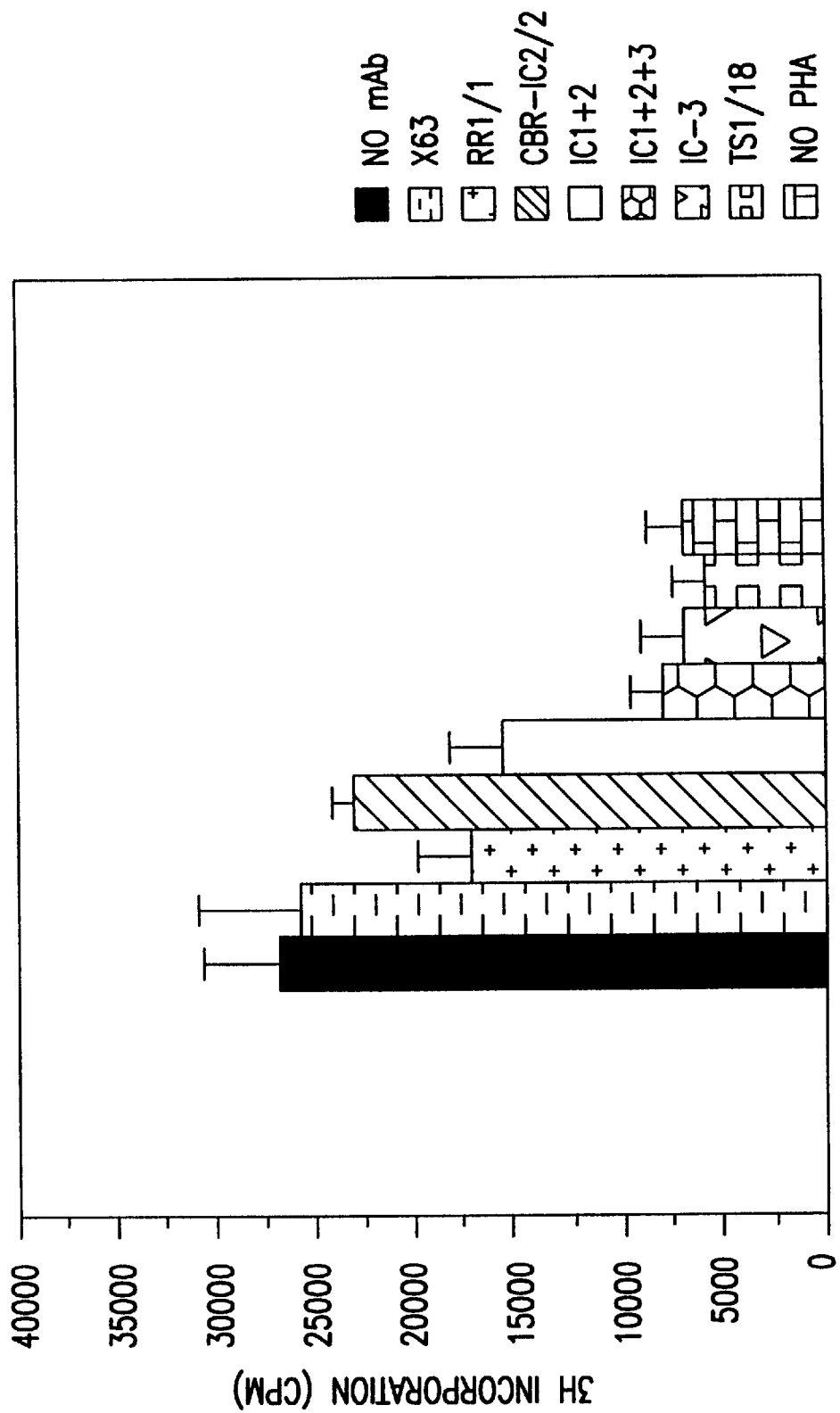

FIG. 9. Antibody blocking of PHA stimulated T cell division.

Various antibodies were tested for their ability to block PHA stimulated T cell division as previously described (Krensky et al., *J. Immunol.* 131:611–616 (1983)).

Figure 10:
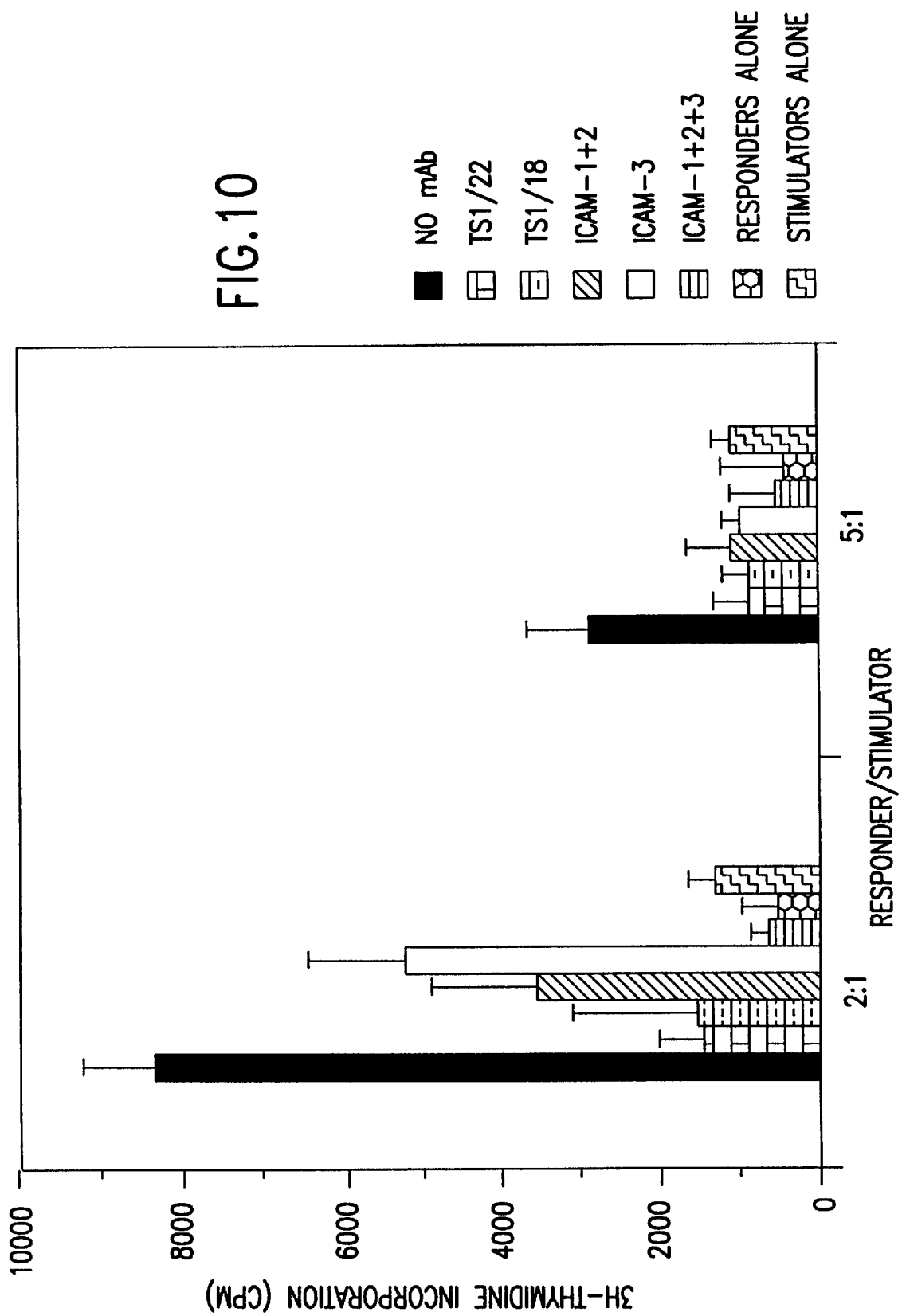

FIG. 10. Effects of anti-ICAM antibodies on the mixed lymphocyte reaction.

Various antibodies were tested for their ability to block mixed lymphocyte reaction as previously described. (Krensky et al., *J. Immunol.* 131:611–616 (1983)).

Figure 11:
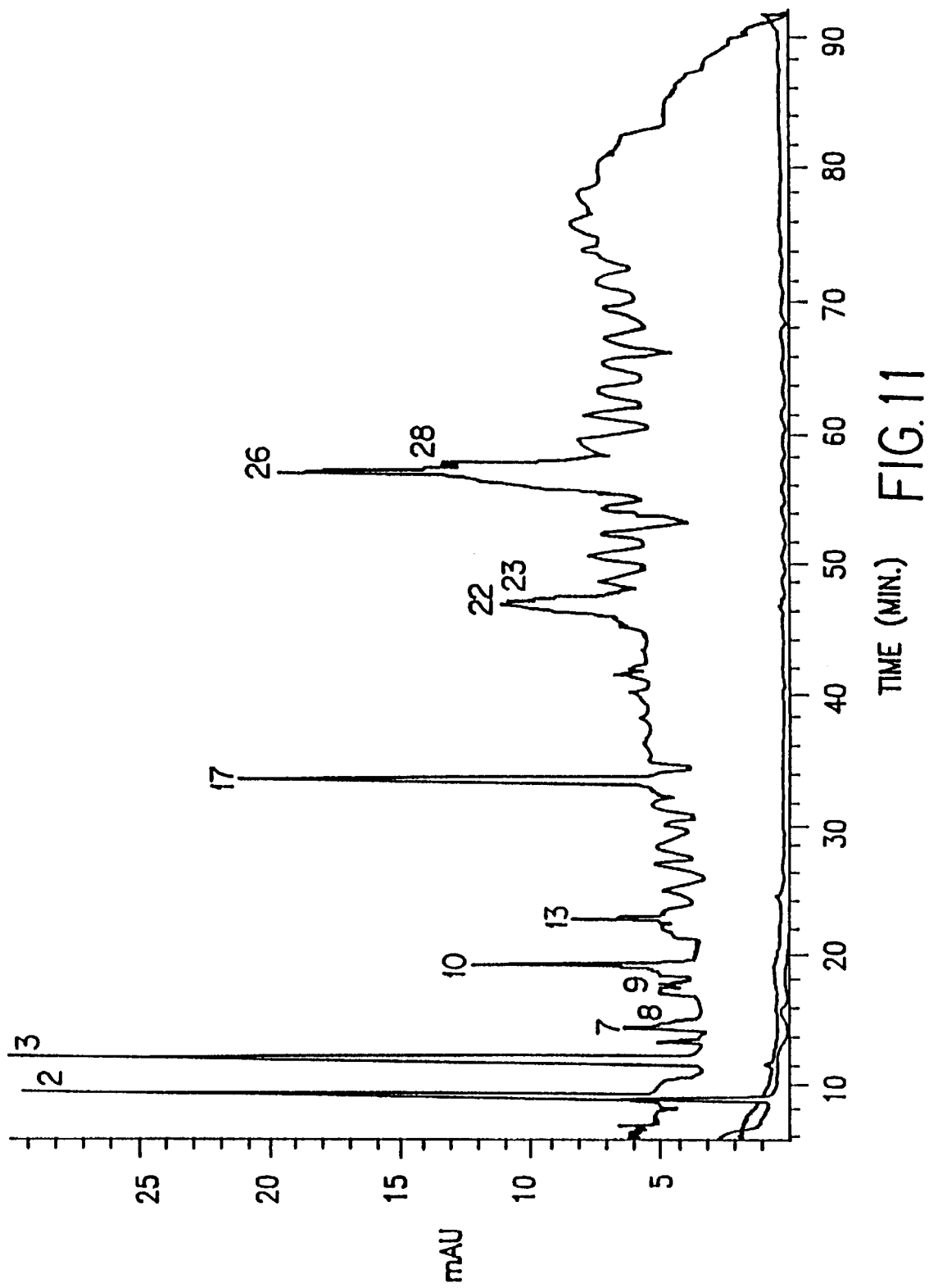

FIG. 11. Gas chromatograph of peptide fragments of ICAM-3.

ICAM-3 was purified and subjected to digestion with Lys-C. Peptide fragments were resolved using high performance liquid chromatograph.

Figure 12:
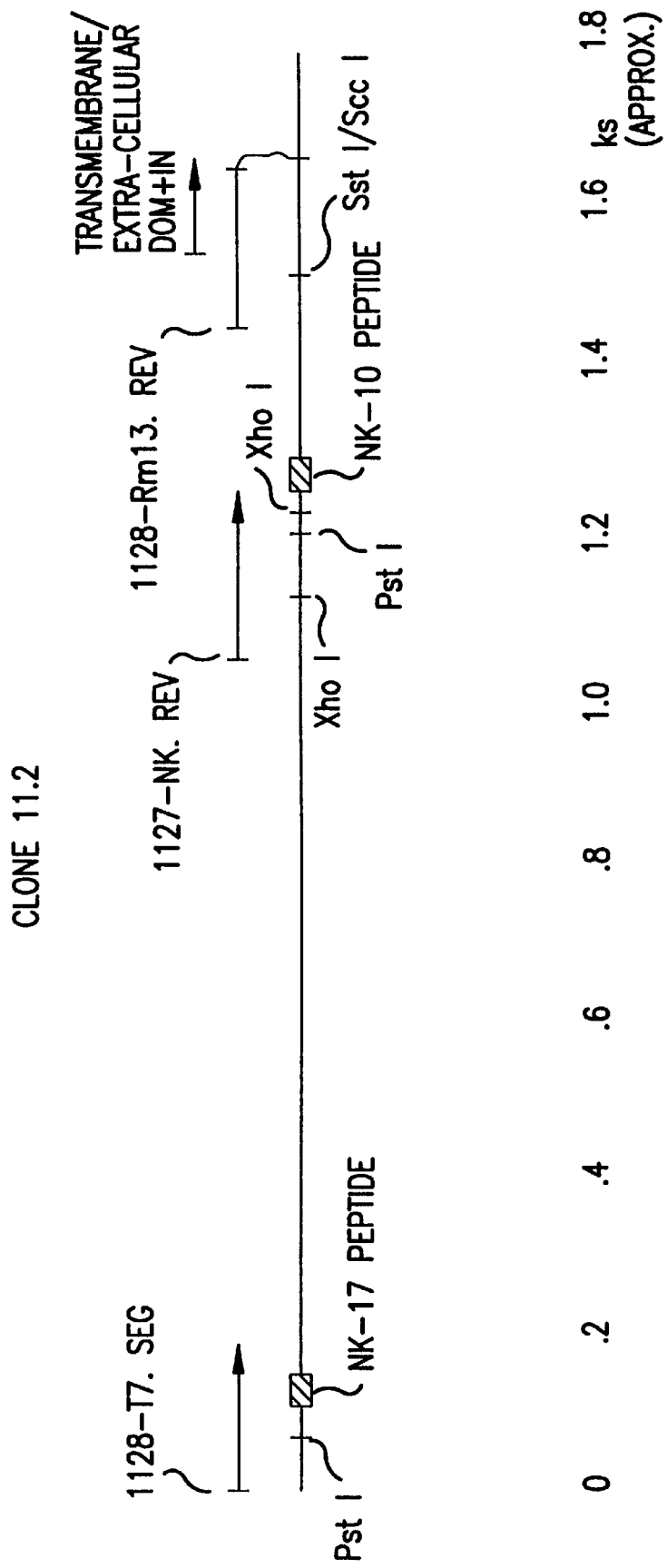

FIG. 12. Diagrammatic representation of clone 11.2.

A diagrammatic representation of clone 11.2. The position of the NK-10 and NK-17 peptides, the various DNA sequences thus far obtained, and the transmembrane region are indicated.

FIG. 13. Sequence comparison of the NK-10 primed sequence (SEQ ID NO. 7) with human ICAM-1 (SEQ ID NO. 2).

The GAP program was used to identify sequence homology of the NK-10 primed sequence and human ICAM-1 protein.

FIG. 14. Sequence comparison of the RM13 primed sequence (SEQ ID NO. 8) with human ICAM-1 (SEQ ID NO. 9).

The GAP program was used to identify sequence homology of the RM13 primed sequence with human ICAM-1.

FIG. 15. Sequence comparison of the RM13 primed sequence (SEQ ID NO. 8) with human ICAM-2. (SEQ ID NO. 10)

The GAP program was used to identify sequence homology of the RM13 primed sequence and human ICAM-2.

FIG. 16. Sequence comparison of the T7 primed sequence (amino acids 31–80 of SEQ ID NO. 6) with human ICAM-1. (SEQ ID NO. 11)

The GAP program was used to identify sequence homology of the T7 primed sequence and human ICAM-1.

FIG. 17. Sequence comparison of the T7 primed sequence (amino acids 31–80 of SEQ ID NO. 6) with human ICAM-2. (SEQ ID NO. 12)

The GAP program was used to identify sequence homology of the T7 primed sequence and human ICAM-2.

FIGS. 18A, 18B and 18C Partial sequence of ICAM-3.

The DNA sequence of clone 11.2 was determined using standard procedures.

FIG. 18A. Sequences obtained from the 5' end of ICAM-3. These sequences were obtained by priming clone 11.2 with the T7 primer. (nucleotides 98–249 of SEQ ID NO. 5, and amino acids 31–80 of SEQ ID NO. 6)

FIG. 18B. Sequences obtained within the ICAM-3 gene. These sequences were obtained by priming clone 11.2 with the NK-10 probe. (SEQ ID NOS. 1,2)

FIG. 18C. Sequences obtained from the 3' end of ICAM-3. The sequences were obtained by priming clone 11.2 with the reverse RM13 primer. (SEQ ID NOS. 3,4)

FIGS. 19A and 19B DNA sequence of ICAM-3.

The DNA sequence (SEQ ID NO. 5) and corresponding amino acid sequence (SEQ ID NO. 6) of ICAM-3 sequenced from clone 11.2 was determined using standard procedures.

Figure 20:
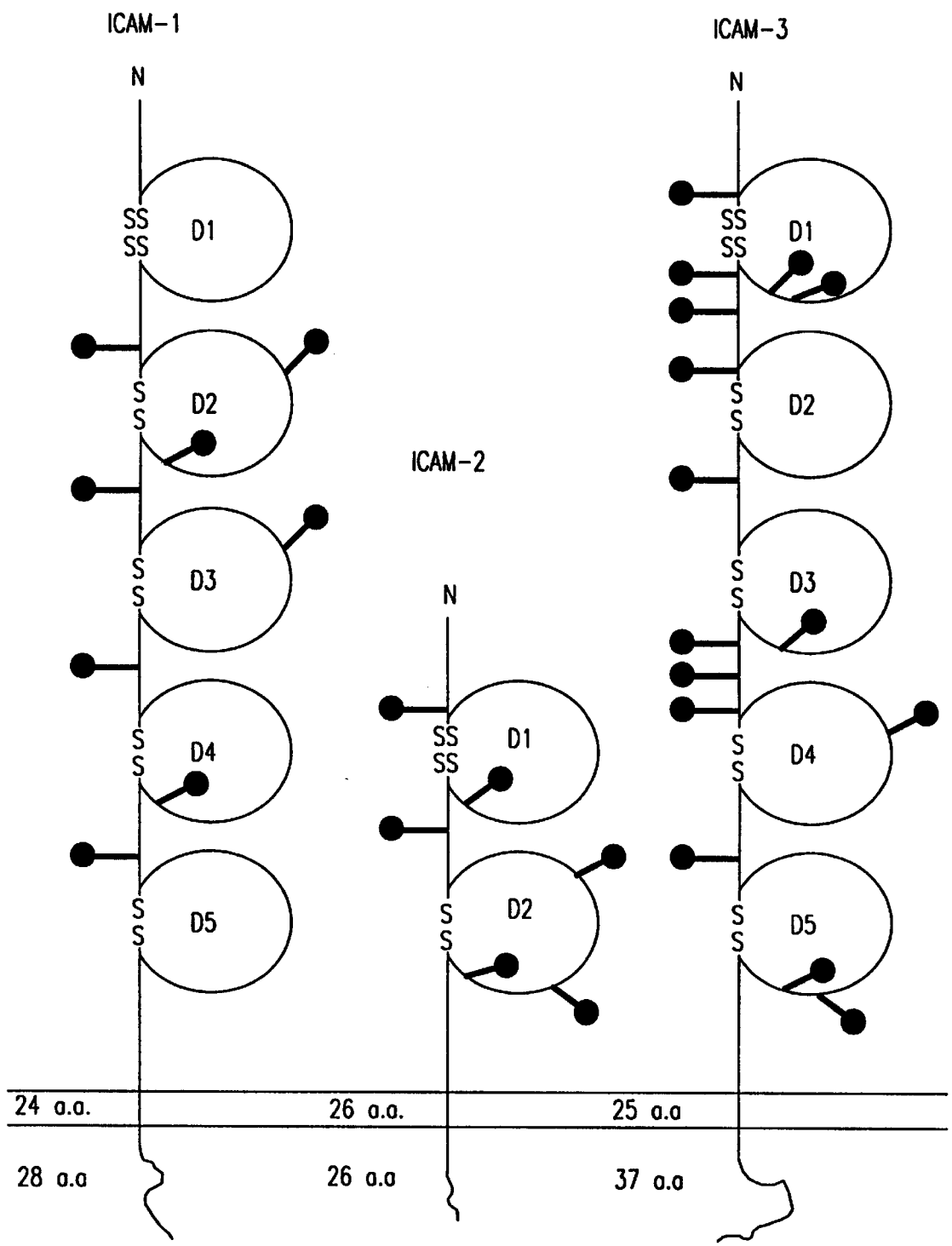

FIG. 20. Diagrammatic representation of ICAM-3 domain structure.

The domain structure of ICAM-3 is improved with that of ICAM-1 and ICAM-2.

DESCRIPTION OF THE PREFERRED EMBODIMENTS

The present invention is based on the discovery of a previously unidentified binding ligand to LFA-1. Molecules such as those of CD-18 family, which are involved in the process of cellular adhesion are referred to as "adhesion molecules."

I. LFA-1

The leukocyte adhesion molecule LFA-1 mediates a wide range of lymphocyte, monocyte, natural killer cell, and granulocyte interactions with other cells in immunity and inflammation (Springer, T. A. et al., *Ann. Rev. Immunol.* 5:223–252 (1987)).

LFA-1 is a receptor for ICAM-1, ICAM-2, and the newly identified ICAM-3 (which is disclosed herein). These surface molecules are constitutively expressed on some tissues and induced on others in inflammation (Marlin, S. D. et al., *Cell* 51:813–819 (1987); Dustin, M. L. et al., *J. Immunol.* 137:245–254 (1986); Dustin, M. L. et al., *Immunol. Today* 9:213–215 (1988); U.S. patent application Serial No. 07/019,440, filed Feb. 26, 1987 and U.S. patent application Ser. No. 07/250,446, filed Sep. 28, 1988, both applications herein incorporated by reference).

LFA-1 functions in both antigen-specific and antigen-independent T cytotoxic, T helper, natural killer, granulocyte, and monocyte interactions with other cell types (Springer, T. A. et al., *Ann. Rev. Immunol.* 5:223–252 (1987); Kishimoto, T. K. et al., *Adv. Immunol.* (1988, in press)).

II. ICAM-1

ICAM-1 is a single chain glycoprotein varying in mass on different cell types from 76–114 kD, and is a member of the Ig superfamily with five C-like domains (Dustin, M. L. et al., *Immunol. Today* 9:213–215 (1988); Staunton, D. E. et al., *Cell* 52:925–933 (1988); Simmons, D. et al., *Nature* 331:624–627 (1988)). ICAM-1 is highly inducible with cytokines including IFN-g, TNF, and IL-1 on a wide range of cell types (Dustin, M. L. et al., *Immunol. Today* 9:213–215 (1988)). Induction of ICAM-1 on epithelial cells, endothelial cells, and fibroblasts mediates LFA-1 dependent adhesion of lymphocytes (Dustin, M. L. et al., *J. Immunol.* 137:245–254 (1986); Dustin, M. L. et al., *J. Cell. Biol.* 107:321–331 (1988); Dustin, M. L. et al., *J. Exp. Med.* 167:1323–1340 (1988)). Adhesion is blocked by pretreatment of lymphocytes with LFA-1 MAb or pretreatment of the other cell with ICAM-1 MAb (Dustin, M. L. et al., *J. Immunol.* 137:245–254 (1986); Dustin, M. L. et al., *J. Cell. Biol.* 107:321–331 (1988); Dustin, M. L. et al., *J. Exp. Med.* 167:1323–1340 (1988)). Identical results with purified ICAM-1 in artificial membranes or on Petri dishes demonstrate that LFA-1 and ICAM-1 are receptors for one another (Marlin, S. D. et al., *Cell* 51:813–819 (1987); Makgoba, M. W. et al., *Nature* 331:86–88 (1988)). For clarity, they are referred to herein as "receptor" and "ligand," respectively. Further descriptions of ICAM-1 are provided in U.S. patent applications Ser. Nos. 07/045,963; 07/115,798; 07/155,943; 07/189,815 or 07/250,446, all of which applications are herein incorporated by reference in their entirety.

III. ICAM-2

Other LFA-1 ligands, distinct from ICAM-1, have been postulated (Rothlein, R. et al., *J. Immunol.* 137:1270–1274 (1986); Makgoba, M. W. et al., *Eur. J. Immunol.* 18:637–640 (1988); Dustin, M. L. et al., *J. Cell. Biol.* 107:321–331 (1988)). The second LFA-1 ligand identified is designated "ICAM-2".

ICAM-2 differs from ICAM-1 in cell distribution and in a lack of cytokine induction. ICAM-2 is an integral membrane protein with 2 Ig-like domains, whereas ICAM-1 has 5 Ig-like domains (Staunton, D. E. et al., *Cell* 52:925–933 (1988); Simmons, D. et al., *Nature* 331:624–627 (1988)). Remarkably, ICAM-2 is much more closely related to the two most N-terminal domains of ICAM-1 (34% identity) than either ICAM-1 or ICAM-2 is to other members of the Ig superfamily, demonstrating a sub-family of Ig-like ligands which bind the same integrin family receptor. Further description of ICAM-2 is provided in U.S. patent application Ser. No. 07/454,294, herein incorporated by reference.

IV. ICAM-3

The present invention concerns the discovery of a third LFA-1 ligand, designated "ICAM-3".

Development of MAb to ICAM-2 allowed several previously LFA-1-dependent, ICAM-1-independent phenomena to be analyzed, and suggested that a third ligand for LFA-1 existed. Binding of several cell types such as epithelial and endothelial cells to purified LFA-1 could be completely blocked with a combination of ICAM-1 and ICAM-2 MAb, whereas an ICAM-1, ICAM-2-independent pathway of adhesion to LFA-1 existed on many lymphoid cell lines, including the T cell lymphoma cell line, SKW3 (FIG. 1).

Figure 1B:
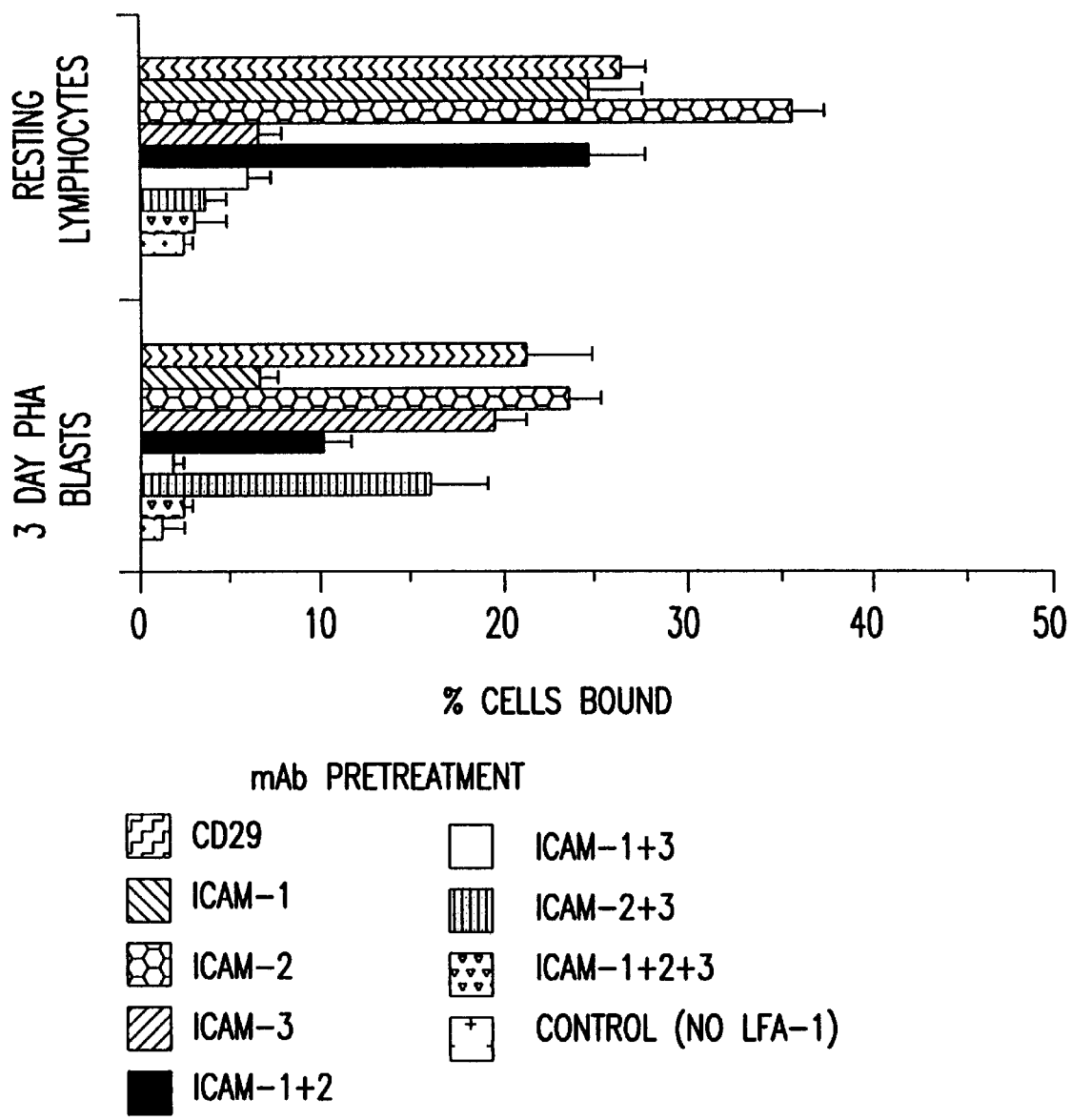

To characterize this pathway of adhesion, MAb were raised to SKW3 and, in concert with anti-ICAM-1 and anti-ICAM-2 MAbs, screened for the ability to inhibit, binding of this cell line to purified LFA-1. One MAb, CBR-IC3/1, was selected which completely inhibited this novel pathway of adhesion (FIG. 1). SKW3 adhesion to purified LFA-1 was only slightly inhibited by a combination of blocking anti-ICAM-1 and anti-ICAM-2 MAb. When the anti-ICAM-3 MAb, CB-IC3/1, was added alone, it significantly inhibited the adhesion, and this inhibition was complete when combined with blocking anti-ICAM-2 MAb. Thus, the adhesion of SKW3 to purified LFA-l was mediated largely by ICAM-3 and also, in part, by ICAM-2. In adhering to LFA-1, each of the four cell lines utilized the three ICAMs to different degrees, as demonstrated by the different patterns of MAb inhibition. The adhesion of B lymphoblastoid cell line, JY, occurred primarily through an ICAM-1 pathway with slight contributions through the ICAM-2 and ICAM-3 pathways. Another B lymphoblastoid cell line, SLA, utilized both ICAM-1 and ICAM-3, since adhesion was not inhibited by either ICAM-1 or ICAM-3 MAb alone and almost completely by the MAbs together. The thymoma cell line, Jurkat, used both the ICAM-2 and ICAM-3 pathways of adhesion with a small contribution by ICAM-1. Adhesion of both resting T lymphocytes and those activated with phytohemagglutinin (PHA) was also investigated (FIG. 1B). Resting lymphocytes were previously shown to bind strongly to purified LFA-1 (Dustin et al., *Nature* 341:619–624 (1989), and this binding was found to be largely ICAM-3-dependent. Upon activation with PHA, ICAM-1 expression was induced and adhesion to LFA-1 occurred chiefly through ICAM-1, and in part, through ICAM-3. The ICAM-2 component of adhesion in both the resting and activated T cells was detectable, though masked by the presence of ICAM-1 and ICAM-3. There is considerable redundancy in use of ICAMs since for each cell, MAb's to at least two ICAMs were required to achieve substantial inhibition. The notable exception to this is the adhesion of resting lymphocytes to LFA-1, which was largely ICAM-3-mediated. In all cases, the combination of all three anti-ICAM- MAb eliminated binding to LFA-1 to levels comparable to those seen in the presence of anti-LFA-1 MAb.

The relative affinity for three ICAMs for LFA-1 can be examined by comparing their contributions to binding LFA-1 as measured above to their cell surface expression as measured by immunofluorescence flow cytometry (FIG. 2). The comparison of surface expression of the ICAMs and their contribution to LFA-1 adhesion revealed that ICAM-1 has the greatest affinity for LFA-1, and that ICAM-2 and ICAM-3 have similar, but lower, affinities. For instance, Jurkat cells expressed ICAM-2 and ICAM-3 at similar levels, and each contributed to binding to LFA-1. Where ICAM-2 expression was greater than that of ICAM-3, such as on JY cells, the ICAM-2 pathway of LFA-1 adhesion prevailed over ICAM-3. In contrast, SLA and SKW3 expressed 3–5 fold more ICAM-3 than ICAM-2 and, not surprisingly, the ICAM-3 pathway of adhesion predominated over the ICAM-2 pathway. On resting T lymphocytes were ICAM-3 was well expressed, and ICAM-1 absent, adhesion to LFA-1 was mediated largely through ICAM-3. When ICAM-1 was well expressed, as was the case with SLA, JY, and the PHA-activated T cells, this was the primary pathway of adhesion.

The pattern of distribution of ICAM-3 differed from that of ICAM-1 and ICAM-2 in several ways. Unlike ICAM-1 and ICAM-2, ICAM-3 was not expressed on either resting or stimulated endothelium (data not shown). This is in agreement with the finding that LFA-1-dependent binding of cells to both resting and stimulated endothelium was an ICAM-1 and ICAM-2-dependent phenomenon. ICAM-3 was restricted to the hematopoietic lineage, being highly expressed on lymphoid and monocytic cell lines, with a few exceptions. In all cases, however, expression of ICAM-3 on cell lines was coordinate with LFA-1-dependent, ICAM-1, ICAM-2-independent pathway of adhesion. Cell lines (HUVEC, Raji) binding LFA-1 solely through ICAM-1 and ICAM-2 showed no ICAM-3 expression, while cell lines (JY, U937, Sup T) which showed weak binding through this third pathway of adhesion had correspondingly low ICAM-3 surface expression (data not shown).

ICAM-3 differed markedly from ICAM-1 and ICAM-2 in its expression on leukocytes (FIG. 2B). ICAM-3 was expressed at high levels on resting lymphocytes, monocytes, and neutrophils, while ICAM-1 and ICAM-2 were expressed much more weakly or absent. By comparison, ICAM-1 and ICAM-2 were weakly expressed on monocytes, and only ICAM-2 was present on resting lymphocytes. Neither ICAM-1 nor ICAM-2 were expressed on neutrophils. Upon activation of lymphocytes with PHA, ICAM-3 expression increased 2–3 fold, whereas ICAM-1 expression was greatly induced (Dustin et al., *J. Immunol.* 137:245–254 (1986)) (FIG. 2B).

Immunoprecipitates of ICAM-3 from various $^{125}$I labeled cell lines revealed a sharp band of 124,000 $M_r$ under reducing conditions with only slightly increased mobility under nonreducing condition (FIG. 3A). Treatment with N-glycanase resulted in reduction of the ICAM-3 band to $M_r$ 87,000, indicating that ICAM-3, like ICAM-1 and ICAM-2, is a highly glycosylated protein (FIG. 3B). The biochemical characteristics, patterns of expression, and functional properties of ICAM-3 distinguish it from previously described adhesion molecules, including the human homing receptor LAM-1 (Tedder et al., *J. Immunol.* 144:532–540 (1990)), the inducible endothelial adhesion molecule VACAM-1 (Rice et al., *J. Exp. Med.* 171:1369–1374 (1990); Carlos et al., *Blood* in press (1990); (Osborn et al., *Cell* 59:1203–1211 (1989)), and the VLA family of matrix receptors (Hemler, M. E., *Ann. Rev. Immunol.* 8:365–400 (1990)), and no MAbs with similar cell distributions were found in the fourth leukocyte workshop databases (Gilks, W. R., et al. Leukocyte Typing Data Base IV, Oxford University Press, Oxford, England, (1990)).

The existence of three LFA-1 ligands suggests specialization for different aspects of LFA-1-dependent leukocyte interactions. ICAM-1 is basally expressed on endothelium and many epithelial cell types, and is strongly induced in inflammation and immunity where it regulates cell localization and facilitates specific antigen recognition (Wawryk et al., *Immunol. Rev.* 108:135–161 (1989)). Since ICAM-2 is the predominant LFA-1 ligand on resting endothelium, this pathway of adhesion may have important consequences for normal recirculation of LFA- 1-bearing lymphocytes through tissue endothelium (Hamann et al., *J. Immunol* 140:693–699 (1988); Mackay et al., *J. Exp. Med.* 171:810–817 (1990); Pals et al., *J. Immunol* 140:1851–1853 (1988); and (Nunoi et al., *Hum. Path.* 19:753–759 (1988)). Presently, the function of ICAM-3 on neutrophils remains unclear, as homotypic aggregation of neutrophils appears to be primarily Mac-1-dependent, despite the presence of LFA-1 (Anderson et al., *J. Immunol.* 137:15–27 (1986); Patarroyo et al., *Scand. J. Immunol.* 22:619–631 (1985)). The finding that adhesion of resting T lymphocytes to LFA-1 occurs primarily via ICAM-3, combined with the fact that ICAM-3 is much better expressed than the other LFA-1 ligands on monocytes and resting lymphocytes implies an important role in the initiation of immune responses. Indeed, T cell adhesion with antigen presenting cells requires LFA-1:ICAM interactions (Dransfield et al., *Imm. Rev.* 114:29–44 (1990); Makgoba et al., *Immunol. Today* 10:417–422 (1989) ), and as such ICAM-3 may play a role, especially on resting T lymphocytes where neither ICAM-1 nor ICAM-2 are well expressed. Indeed, a role is suggested for LFA-1 ligand(s) other than ICAM-1 in both allogeneic and autologous mixed lymphocyte reactions (Bagnasco et al., *Cell Immunol.* 128:362–369 (1990)). Furthermore, ICAM-3 would be predicted to be important in antigen-specific interactions between T and B lymphocytes, where one of these cells has not yet been activated. ICAM-3 may also be important in lysis of certain targets by T cells that is dependent on LFA-1 but not ICAM-1 (Makgoba et al., *Eur. J. Immunol.* 18:637–640 (1988)).

The existence of multiple ICAMs has important implications for clinical treatment with MAb to ICAMs or ICAM analogues. ICAM-1 MAb is efficacious in vivo in prolonging renal (Cosimi et al., *J. Immunol.* 144:4604–4612 (1990)) and cardiac (Flavin et al., *Transplant. Proc.* 23:533–534 (1991)) allografts. ICAM-3 MAb inhibits a distinctive and overlapping number of immune responses in vivo, since it inhibits LFA-1-dependent adhesive interactions of a distinct subset of cell types.

V. cDNA CLONING OF ICAM-3

Any of a variety of procedures may be utilized to clone the ICAM-3 gene. One such method entails analyzing a shuttle vector library of cDNA inserts (derived from an ICAM-3 expressing cell) for the presence of an insert which contains the ICAM-3 gene. Such an analysis may be conducted by transfecting cells with the vector and then assaying for ICAM-3 expression.

ICAM-3 cDNA is preferably identified using a modification of the procedure of Aruffo and Seed (Seed, B. et al., *Proc. Natl. Acad. Sci. USA* 84:3365–3369 (1987)) to identify ligands of adhesion molecules. In this method, a cDNA library is prepared from cells which express ICAM-3 (such as SLA, Jurkat, or SKW3 lymphoblastoid cell lines). Preferably, the cDNA library is prepared from T-cells. This library is used to transfect cells which do not normally express ICAM-3 (such as Cos or HeLa cells). The transfected cells are introduced into a petri dish which has been previously coated with either LFA-1 or anti-ICAM-3 antibodies. The transfected cells containing ICAM-3 encoding sequences, and which express this ligand on their cell surfaces, will adhere to the LFA-1 or anti-ICAM-3 antibodies on the surface of the petri dish. Non-adherent cells are washed away, and the adherent cells are then removed from the petri dish and cultured. The recombinant ICAM-3 expressing sequences in these cells is then removed is sequenced.

If LFA-1 is used to coat the petri plate, anti-ICAM-1 and anti-ICAM-2 specific antibodies are added to the petri dish in order to prevent the adherence of ICAM-1 or ICAM-2 expressing cells. Adherence of ICAM-1$^+$ or ICAM-$^{2+}$ transfectants to LFA-1 coated plastic may thus be inhibited with antibodies such as RR1/1, an anti-ICAM-1 MAb and CBR-IC2/2, an anti-ICAM-2 MAb. Binding of ICAM-3 transfected cells to LFA-1 coated petri plates is inhibited by EDTA and anti-LFA-1 MAbs, but is not inhibited by anti-ICAM-1 or anti-ICAM-2 MAbs. Therefore the ICAM-1 or ICAM-2 expressing cells are unable to adhere to the petri dish and are therefore mostly washed away with all of the other non-adherent cells. This will enrich for cells expressing ICAM-3.

Other alternative method of obtaining gene sequences encoding ICAM-3 are well known in the art, and one so skill will routinely adapt one of these methods in order to obtain a desired gene.

One such method for obtaining a gene sequence which encodes ICAM-3 is to use an oligonucleotide probe to screen a cDNA or genomic DNA library. In this method, the ICAM-3 protein is purified, preferably using immuno-purification procedures known in the art, and the terminal amino acid sequence is determined using one of the methods known in the art. Alternatively, ICAM-3 is tryptically mapped, and the amino acid sequence of one of the internal fragments is determined.

Once the partial amino acid sequence is determined, either an oligonucleotide probe is made based on the codon preference displayed by the organism, or a degenerate probe is made based on all possible codon combinations. This probe is then used to screen either a genomic or cDNA library for sequences which hybridize to the probe.

Techniques such as, or similar to, those described above have successfully enabled the cloning of genes for human aldehyde dehydrogenases (Hsu, L. C. et al., *Proc. Natl. Acad. Sci. USA* 82:3771–3775 (1985)), fibronectin (Suzuki, S. et al., *Eur. Mol. Biol. Organ. J.* 4:2519–2524 (1985)), the human estrogen receptor gene Walter, P. et al., *Proc. Natl. Acad. Sci. USA* 82:7889–7893 (1985)), and tissue-type plasminogen activators (Pennica, D., et al., *Nature* 301:214–221 (1983)).

In yet another alternative way of cloning the ICAM-3 gene, an expression library is prepared by cloning genomic DNA or, more preferably cDNA, from a cell which expresses ICAM-3. The library is then screened for members capable fo expressing a protein which binding to an anti-ICAM-3 antibody.

The cloned ICAM-3 gene, obtained through the use of any of the method described above, may be operably linked to an expression vector, and introduced into bacterial, or eukaryotic cells to produce the ICAM-3 protein. Techniques for such manipulations are disclosed in Maniatis, T. et al., supra., and are well known in the art.

In an alternative method utilizing PCR to clone to ICAM-3 gene, an assumption that ICAM-3 is homologous to ICAM-1 and/or ICAM-2 is made. Degenerate oligonucleotide primers based on sequences conserved between ICAM-1 and ICAM-2 are used amplify by the polymerase chain reaction cDNA or mRNA, from cells known to express ICAM-3 protein, such as SKW3 or tonsil (deFougerolles et al., *J. Exp. Med.,* 175:185–190 (1992)). Clones are sequenced, and those distinct from ICAM-1 and ICAM-2 are used to obtain full length cDNA clones.

In any of the methods described above the authenticity of clones can be confirmed by expressing fully length clones, for example in COS cells, and testing for reactivity with ICAM-3 mAb.

VI. THE AGENTS OF THE PRESENT INVENTION: ICAM-3 AND ITS FUNCTIONAL DERIVATIVES, AGONISTS AND ANTAGONISTS

The present invention is further directed toward ICAM-3, its "functional derivatives," its "agonists" and "antagonists."

A. Functional Derivatives of ICAM-3

A "functional derivative" of ICAM-3 is a compound which possesses a biological activity (either functional or structural) that is substantially similar to the biological activity of ICAM-3. The term "functional derivative" includes "fragments," "variants," and "chemical derivatives" of the parent ICAM-3 molecule.

A "fragment" of ICAM-3 is meant to refer to any polypeptide subset of the molecule. Fragments of ICAM-3 which have ICAM-3 activity and which are soluble (i.e not membrane bound) are especially preferred. A soluble fragment is preferably generated by deleting the membrane spanning region of the parent molecule or by deleting or substituting hydrophilic amino acid residues for hydrophobic residues. Identification of such residues is well known in the art.

Fragments containing any number of whole Ig-like domain are preferred, such as domain 1 (D1), D1 and D2, D1–3, D1–4, and D1–5.

A "variant" of ICAM-3 is meant to refer to a molecule substantially similar in structure and function to either the entire molecule, or to a fragment thereof.

A molecule is said to be "substantially similar" to another molecule if both molecules have substantially similar structures or if both molecules possess a similar biological activity. Thus, provided that two molecules possess a similar activity, they are considered variants, as that term is used herein, even if one of the molecules possesses a structure not found in the other molecule, or if the sequence of amino acid residues is not identical.

As used herein, a molecule is said to be a "chemical derivative" of another molecule when it contains additional chemical moieties which are not normally a part of the naturally occurring molecule. Such moieties may improve the molecule's solubility, absorption, biological half life, etc. The moieties may alternatively decrease the toxicity of the molecule, or eliminate or attenuate any undesirable side effect of the molecule. Moieties capable of mediating such effects are disclosed in *Remington's Pharmaceutical Sciences* (1980).

"Toxin-derivatized" molecules constitute a special class of "chemical derivatives." A "toxin-derivatized" molecule is a molecule (such as ICAM-3 or an anti-ICAM-3 antibody) which is covalently attached to a toxin moiety. Procedures for coupling such moieties to a molecule are well known in the art.

The binding of such a molecule to a cell brings the toxin moiety into close proximity to the cell and thereby promotes cell death. Any suitable toxin moiety may be employed; however, it is preferable to employ toxins such as, for example, the ricin toxin, the cholera toxin, the diphtheria toxin, radioisotopic toxins, or membrane-channel-forming toxins.

Functional derivatives of ICAM-3 having up to about 100 residues may be conveniently prepared by in vitro synthesis. If desired, such fragments may be modified using methods known in the art by reacting targeted amino acid residues of the purified or crude protein with an organic derivatizing agent that is capable of reacting with selected side chains or terminal residues. The resulting covalent derivatives may be used to identify residues important for biological activity.

Many methods may be employed to generate and isolate fragments of 1CAM-3. Derivatization with bifunctional agents can be used to crosslink ICAM-3 to a water-insoluble support matrix. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Functional derivatives of ICAM-3 having altered amino acid sequences can also be prepared by mutating the DNA encoding ICAM-3. Such functional derivatives include, for example, deletions from, or insertions or substitutions of, residues within the amino acid sequence of ICAM-3. Any combination of deletion, insertion, and substitution may be employed to generate the final construct, provided that the final construct possesses the desired activity. Obviously, the mutations that will be made in the DNA encoding the functional derivative must not place the sequence out of reading frame and preferably will not create complementary regions that could produce secondary mRNA structure (see EP Patent Application Publication No. 75,444).

At the genetic level, functional derivatives can be prepared by site-directed mutagenesis of the DNA encoding ICAM-3, thereby producing DNA encoding the functional derivative, and thereafter expressing the DNA in recombinant cell culture.

While the site for introducing a variation in the amino acid sequence is predetermined, the mutation per se need not be predetermined. For example, to optimize the performance of a mutation at a given site, random mutagenesis, such as linker scanning mutagenesis, may be conducted at a target codon or target region to create a large number of derivative which could then be expressed and screened for the optimal combination of desired activity. Techniques for making mutations at predetermined sites in a DNA known sequence are well known, for example, site-directed mutagenesis.

Preparation of functional derivative of ICAM-3 in accordance herewith is preferably achieved by site-directed mutagenesis of the DNA that encodes ICAM-3 or an earlier prepared functional derivative of ICAM-3. The technique of such site-specific mutagenesis is well known in the art, as exemplified by publications such as Maniatis, T. et al., In: *Molecular Cloning, a Laboratory Manual,* Coldspring Harbor, N.Y. (1982), the disclosure of which is incorporated herein by reference. Site-directed mutagenesis allows the production of ICAM-3 functional derivatives through the use of specific oligonucleotide sequences that encode the DNA sequence of the desired mutation.

One can generate amino acid deletions, insertions, or substitution using site-directed mutagenesis. Amino acid sequence deletions generally range from about 1 to 30 residues, more preferably 1 to 10 residues, and typically are contiguous. The most preferred deletions are those which are performed to generate a soluble form of ICAM-3. Soluble forms of ICAM-3 are most preferably generated by deleting either the membrane spanning region of ICAM-3 or hydrophobic residues within ICAM-3.

Amino acid insertions include insertions of single or multiple amino acid residues within the ICAM-3 coding sequences as well as terminal fusions with polypeptides of essentially unrestricted length. Intrasequence insertions (i.e., insertions within the complete ICAM-3 molecule sequence) may range generally from about 1 to 10 residues, more preferably 1 to 5. An example of a terminal insertion includes a fusion of a signal sequence, whether heterologous or homologous to the host cell, to the N-terminus of the molecule to facilitate the secretion of the derivative from recombinant hosts.

The third group of functional derivatives are those in which at one or more amino acid residue in the ICAM-3 molecule has been removed and a different residue inserted in its place. Such substitutions preferably are made in accordance with the following Table when it is desired to modulate finely the characteristics of the ICAM-3 molecule.

TABLE 1

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that are in general less conservative are those in which (a) glycine and/or proline is substituted by another amino acid or is deleted or inserted; (b) a hydrophilic residue is substituted for a hydrophobic residue; (c) a cysteine residue is substituted for (or by) any other residue; (d) a residue having an electropositive side chain is substituted for (or by) a residue having an electronegative charge; or (e) a residue having a bulky side chain is substituted for (or by) one not having such a side chain.

Most preferred are substitution which effect the solubility of ICAM-3. These are most preferably generated by substituting hydrophilic for hydrophobic amino acids.

Mutations designed to increase the affinity of ICAM-3 may be guided by the introduction of the amino acid residues which are present at homologous positions in ICAM-1 or ICAM-2. Similarly, such mutant ICAM-3 molecules may be prepared which lack N-linked CHO at homologous positions in ICAM-1 or ICAM-2.

It is difficult to predict the exact effect any particular substitution, deletion, or insertion will have on the biological activity of ICAM-3 in advance of doing so. However, one skilled in the art will appreciate that the effect will be evaluated by routine screening assays. For example, a derivative typically is made by linker scanning site-directed mutagenesis of the DNA encoding the native ICAM-3 molecule. The derivative is then expressed in a recombinant host, and, optionally, purified from the cell culture, for example, by immunoaffinity chromatography.

The activity of the cell lysate or the purified derivative is then screened in a suitable screening assay for the desired characteristic. For example, a change in the immunological character of the functional derivative, such as affinity for a given antibody, is measured by a competitive type immunoassay. Changes in immunomodulation activity are measured by the appropriate assay. Modifications of such protein properties as redox or thermal stability, biological half-life, hydrophobicity, susceptibility to proteolytic degradation, or the tendency to aggregate with carriers or into multimers are assayed by methods well known to the ordinarily skilled artisan.

B. Agonists and Antagonists of ICAM-3

An "agonist" of ICAM-3 is a compound which enhances or increases the ability of ICAM-3 to carry out any of its biological functions. An example of such an agonist is an agent which increases the ability of ICAM-3 to bind to a cellular receptor.

An "antagonist" of ICAM-3 is a compound which diminishes or prevents the ability of ICAM-3 to carry out any of its biological functions. Examples of such antagonists include ICAM-1 and ICAM-2, a functional derivative of ICAM-1 and ICAM-2, an anti-ICAM-3 antibody, an anti-LFA-1 antibody, etc.

The cellular aggregation assays described in U.S. patent applications Ser. Nos. 07/045,963; 07/115,798; 07/155,943; 07/189,815 or 07/250,446, all of which applications have been herein incorporated by reference in their entirety, are capable of measuring LFA-1 dependent aggregation, and may thus be employed to identify agents which affect the extent of ICAM-3/LFA-1 aggregation. Thus, such assays may be employed to identify agonists and antagonists of ICAM-3. Antagonists may act by impairing the ability of LFA-1 or of ICAM-3 to mediated aggregation. Additionally, non-immunoglobulin (i.e., chemical) agents may be examined, using the above-described assay, to determine whether they are agonists or antagonists of ICAM-3/LFA-1 mediated aggregation. Such aggregation assays are typically performed using peripheral T-cells stimulated with PMA. Thus the binding of peripheral blood cells to LFA-1 is used to assay ICAM-3 mediated aggregation.

C. Anti-ICAM-3 Antibody

The preferred immunoglobulin antagonist of the present invention is an antibody to ICAM-3 such as CBR-IC3/1, disclosed herein. Other suitable anti-ICAM-3 antibodies can be obtained in any of a variety of ways.

The antibodies to ICAM-3 (or functional derivatives of ICAM-3) may be either polyclonal or monoclonal. Additionally, the antibodies of the present application may be humanized by procedures known in the art or by the procedures disclosed in PCT Application Nos. PCT/US91/02942 and PCT/US91/02946 filed at the U.S. Receiving Office on Apr. 22, 1991.

Anti-ICAM-3 antibodies may be made by introducing ICAM-3, or peptide fragments thereof, into an appropriate animal. The immunized animal will produce polyclonal antibody in response to such exposure. The use of peptide fragments of ICAM-3 permits one to obtain region specific antibodies which are reactive only with the epitope(s) contained in the peptide fragments used to immunize the animal.

Alternatively, anti-ICAM-3 antibodies may be made using the ICAM-3 which is naturally expressed on the surfaces of lymphocytes. The introduction of such cells into an appropriate animal, such as by intraperitoneal injection, will result in the production of antibodies capable of binding to ICAM-3 or members of the CD-18 family of molecules. If desired, the serum of such an animal may be removed and used as a source of polyclonal antibodies capable of binding these molecules.

Alternatively, anti-ICAM-3 antibodies may be produced by adaptation of the method of Selden, R. F. (European Patent Application Publication No. 289,034) or Selden R. F. et al. (*Science* 236:714–718 (1987)). Specifically, the cells of a suitable animal (for example a mouse) are transfected with a vector capable of expressing either the intact ICAM-3 molecule, or a fragment thereof. The production of ICAM-3 in the transfected cells of the animal will elicit an immune response in the animal, and lead to the production of anti-ICAM-3 antibodies by the animal.

It is, however, preferable to remove splenocytes from animals immunized in either of the ways described above, in order to generate monoclonal antibodies capable of binding ICAM-3.

The hybridoma cells, obtained in the manner described above, may be screened by a variety of methods to identify a hybridoma cell that secretes an antibody capable of binding to ICAM-3. In a preferred screening assay, such molecules are identified by their ability to inhibit the aggregation of ICAM-3-expressing, ICAM-1 and ICAM-2 non-expressing cells. Antibodies capable of inhibiting such aggregation are then further screened to determine whether they inhibit such aggregation by binding to ICAM-3, or to a member of the CD-18 family of molecules. Any means capable of distinguishing ICAM-3 from the CD-18 family of molecules may be employed in such a screen. Thus, for example, the antigen bound by the antibody may be analyzed as by immunoprecipitation and polyacrylamide gel electrophoresis. It is possible to distinguish between those anti-bodies which bind to members of the CD-18 family of molecules from those which bind ICAM-3 by screening for the ability of the antibody to bind to cells which express LFA-1, but not ICAM-3 (or vice versa). The ability of an antibody to bind to a cell expressing LFA-1 but not ICAM-3 may be detected by means commonly employed by those of ordinary skill. Such means include immunoassays (especially those using immunofluorescence), cellular agglutination, filter binding studies, antibody precipitation, etc.

In the preferred method, an antibody is selected for its ability to bind to cells expressing ICAM-3, but not to cells which do not express ICAM-3.

In addition to the above-described agonists and antagonists of ICAM-3, other agents which may be used in accordance of the present invention in the treatment of inflammation, HIV infection, asthma, etc. include anti-idiotypic antibodies to anti-ICAM-3 antibodies, and receptor molecules, or fragments of such molecules, which are capable of binding to ICAM-3.

The anti-idiotypic antibodies of interest to the present invention are capable of binding in competition with (or to the exclusion of) ICAM-3. Such antibodies can be obtained, for example, by raising an antibody to an anti-ICAM-3 antibody, and then screening the antibody for the ability to bind to one of the natural binding ligands of ICAM-3.

Since molecules of the CD-18 family are able to bind to ICAM-3, administration of such molecules (for example as heterodimers having both alpha and beta subunits, or as molecules composed of only an alpha, or a beta subunit, or as molecules having fragments of either or both subunits) will compete with cells for the binding to ICAM-3 present on a cell.

The anti-aggregation antibodies of the present invention may be identified and tittered in any of a variety of ways. For example, one can measure the ability of the antibodies to differentially bind to cells which express ICAM-3 (such as T-cells), and their inability to bind to cells which fail to express ICAM-3. Suitable assays of cellular aggregation are those described in U.S. patent applications Ser. Nos. 07/045,963 now abandoned; 07/115,798 now abandoned; 07/155,943 now abandoned; 07/189,815 now abandoned or 07/250,446 now abandoned, all of which applications have been herein incorporated by reference in their entirety. Alternatively, the capacity of the antibodies to bind to ICAM-3 or to a peptide fragment of ICAM-3 can be measured. As will be readily appreciated by those of ordinary skill, the above assays may be modified, or performed in a different sequential order to provide a variety of potential screening assays, each of which is capable of identifying and discriminating between antibodies capable of binding to ICAM-3 versus members of the CD-18 family of molecules.

D. Preparation of the Agents of the Present Invention

The agents of the present invention may be obtained by: natural processes (for example, by inducing an animal, plant, fungi, bacteria, etc., to produce a non-immunoglobulin antagonist of ICAM-3, or by inducing an animal to produce polyclonal antibodies capable of binding to ICAM-3); by synthetic methods (for example, by synthesizing ICAM-3, functional derivatives of ICAM-3, or protein antagonists of ICAM-3 (either immunoglobulin or non-immunoglobulin)); by hybridoma technology (for example, to produce monoclonal antibodies capable of binding to ICAM-3); or by recombinant technology (such as, for example, to produce the agents of the present invention in diverse hosts (i.e., yeast, bacteria, fungi, cultured mammalian cells, etc.), using a recombinant plasmids or viral vectors). The choice of which method to employ will depend upon factors such as convenience, desired yield, etc. However, it is not necessary to employ only one of the above-described methods, processes, or technologies to produce a particular anti-inflammatory agent; the above-described processes, methods, and technologies may be combined in order to obtain a particular agent.

VII. USES OF ICAM-3, AND ITS FUNCTIONAL DERIVATIVES, AGONISTS AND ANTAGONISTS

The agents of the present invention can be used to moderate the various biological activities which are mediated by ICAM-3.

A. Suppression of Inflammation

One aspect of the present invention derives from the ability of ICAM-3 and its functional derivatives to interact with receptors of the CD-18 family of molecules, especially LFA-1. By virtue of the ability of ICAM-3 to interact with members of the CD-18 family of glycoproteins, it may be used to suppress (i.e. to prevent, or attenuate) inflammation.

The term "inflammation," as used herein, is meant to include both the reactions of the specific defense system, and the reactions of the non-specific defense system.

As used herein, the term "specific defense system" is intended to refer to that component of the immune system that reacts to the presence of specific antigens. Inflammation is said to result from a response of the specific defense system if the inflammation is caused by, mediated by, or associated with a reaction of the specific defense system. Examples of inflammation resulting from a response of the specific defense system include the response to antigens such as rubella virus, autoimmune diseases, and delayed type hypersensitivity response mediated by T-cells (as seen, for example in individuals who test "positive" in the Mantaux test). Chronic inflammatory diseases and the rejection of solid transplanted tissue and organs, e.g. kidney and bone marrow transplants, are further examples of inflammatory reactions of the specific defense system.

As used herein, a reaction of the "non-specific defense system" is intended to refer to a reaction mediated by leukocytes which are incapable of immunological memory. Such cells include granulocytes and macrophages. As used herein, inflammation is said to result from a response of the non-specific defense system, if the inflammation is caused by, mediated by, or associated with a reaction of the non-specific defense system. Examples of inflammation which result, at least in part, from a reaction of the non-specific defense system include inflammation associated with conditions such as: adult respiratory distress syndrome (ARDS) or multiple organ injury syndromes secondary to septicemia, trauma or hemorrhage; reperfusion injury of myocardial or other tissues; acute glomerulonephritis; reactive arthritis; dermatoses with acute inflammatory components; acute purulent meningitis or other central nervous system inflammatory disorders such as stroke; thermal injury; hemodialysis; leukapheresis; ulcerative colitis; Crohn's disease; necrotizing enterocolitis; granulocyte transfusion associated syndromes; and cytokine-induced toxicity.

As discussed above, the binding of ICAM-3 molecules to the members of CD-18 family of molecules is of central importance in cellular adhesion. Through the process of adhesion, lymphocytes are capable of continually monitoring an animal for the presence of foreign antigens. Although these processes are normally desirable, they are also the cause of solid organ transplant rejection (e.g. kidney), non-solid organ transplant rejection (e.g. bone marrow) tissue graft rejection and many autoimmune diseases. Hence, any means capable of attenuating or inhibiting cellular adhesion would be highly desirable in recipients of solid organ transplants (especially kidney transplants), non-solid organ transplants (especially bone marrow transplants), tissue grafts, or for autoimmune patients.

Monoclonal antibodies to members of the CD-18 family inhibit many adhesion dependent functions of leukocytes including binding to endothelium (Haskard, D. et al., *J. Immunol.* 137:2901–2906 (1986)), homotypic adhesions (Rothlein, R. et al., *J. Exp. Med.* 163:1132–1149 (1986)), antigen and mitogen induced proliferation of lymphocytes (Davignon, D. et al., *Proc. Natl. Acad. Sci., USA* 78:4535–4539 (1981)), antibody formation (Fischer, A. et al., *J. Immunol.* 136:3198–3203 (1986)), and effector functions of all leukocytes such as lytic activity of cytotoxic T cells (Krensky, A. M. et al., *J. Immunol.* 132:2180–2182 (1984)), macrophages (Strassman, G. et al., *J. Immunol.* 136:4328–4333 (1986)), and all cells involved in antibody-dependent cellular cytotoxicity reactions (Kohl, S. et al., *J. Immunol.* 133:2972–2978 (1984)). In all of the above functions, the antibodies inhibit the ability of the leukocyte to adhere to the appropriate cellular substrate which in turn inhibits the biological function associated with binding.

Such functions, to the extent that they involve ICAM-3/LFA-1 interactions, can be suppressed with anti-ICAM-3 antibodies.

Thus, monoclonal antibodies capable of binding to ICAM-3 can be employed as an anti-inflammatory agent in a mammalian subject. Significantly, such agents differ from general anti-inflammatory agents in that they are capable of selectively inhibiting adhesion, and do not offer other side effects, such as nephrotoxicity, which are found with conventional agents.

Since ICAM-3, particularly in soluble form is capable of acting in the same manner as an antibody to members of the CD-18 family, it may be used to suppress inflammation. Moreover, the functional derivatives and antagonists of ICAM-3 may also be employed to suppress inflammation.

1. Suppressors of Delayed Type Hypersensitivity Reactions

ICAM-3 mediates, in part, adhesion events necessary to mount inflammatory reactions such as delayed type hypersensitivity reactions. Thus, antibodies (especially monoclonal antibodies) capable of binding to ICAM-3 have therapeutic potential in the attenuation or elimination of such reactions.

Alternatively, since ICAM-3 is an antagonist of the ICAM-1/LFA-1 interaction, ICAM-3 (particularly in solubilized form), or its functional derivatives can be used to suppress delayed type hypersensitivity reactions.

These potential therapeutic uses may be exploited in either of two manners. First, a composition containing an anti-ICAM-3 monoclonal antibody or soluble derivative of ICAM-3, may be administered to a patient experiencing delayed type hypersensitivity reactions. For example, such compositions might be provided to a individual who had been in contact with antigens such as poison ivy, poison oak, etc. In another embodiment, a monoclonal antibody capable of binding to ICAM-3 is administered to a patient in conjunction with an antigen in order to prevent a subsequent inflammatory reaction. Thus, the additional administration of an antigen with an anti-ICAM-3 antibody can act to temporarily tolerize an individual to subsequent presentation of that antigen.

2. Therapy for Chronic Inflammatory Disease

Since LAD patients that lack LFA-1 do not mount an inflammatory response, it is believed that antagonism of LFA-1's natural ligands, will also inhibit an inflammatory response. The ability of antibodies against ICAM-3 to inhibit inflammation provides the basis for their therapeutic use in the treatment of chronic inflammatory diseases and autoimmune diseases such as lupus erythematosus, autoimmune thyroiditis, experimental allergic encephalomyelitis (EAE), multiple sclerosis, some forms of diabetes, Reynaud's syndrome, rheumatoid arthritis, etc. Such antibodies may also be employed as a therapy in the treatment of psoriasis.

In general, the anti-ICAM-3 antibodies of the present invention may be administered alone or in combination with anti-ICAM-1 and/or anti-ICAM-2 antibodies in the treatment of those diseases currently treatable through steroid therapy.

In accordance with the present invention, such inflammatory and immune rejection responses may be suppressed (i.e. either prevented or attenuated) by providing to a subject in need of such treatment an amount of an anti-inflammatory agent sufficient to suppress said inflammation. Suitable anti-inflammatory agents include: an antibody capable of binding to ICAM-3; a fragment of said antibody, said fragment being capable of binding to ICAM-3; substantially pure ICAM-3; a functional derivative of ICAM-3; a non-immunoglobulin antagonist of ICAM-3, or a non-immunoglobulin antagonist of ICAM-3 other than LFA-1. Especially preferred are anti-inflammatory agents composed of a soluble functional derivative of ICAM-3. Such anti-inflammatory treatment can also include the additional administration of an agent selected from the group consisting of: an antibody capable of binding to LFA-1; a non-immunoglobulin antagonist of LFA-1; substantially pure ICAM-1 and/or ICAM-2, or derivatives thereof, or an anti-ICAM-1 and/or anti-ICAM-2 antibody or fragment thereof.

The invention further includes the above-described methods for suppressing an inflammatory response of the specific defense system in which an immunosuppressive agent is additionally provided to the subject. Such an agent is preferably provided at a dose lower (i.e. a "sub-optimal" dose) than that at which it would normally be required. The use of a sub-optimal dose is possible because of the synergistic effect of the agents of the present invention. Examples of suitable immunosuppressive agents include but are not limited to dexamethasone, azathioprine, ICAM-1, ICAM-2, or cyclosporin A.

3. Therapy for Non-Specific Inflammation

Many inflammatory reactions are due to reactions of the "non-specific defense system" and are mediated by leukocytes which are incapable of immunological memory. Such cells include granulocytes and macrophages. As used herein, inflammation is said to result from a response of the non-specific defense system, if the inflammation is caused by, mediated by, or associated with a reaction of the non-specific defense system. Examples of inflammation which result, at least in part, from a reaction of the non-specific defense system include inflammation associated with conditions such as: adult respiratory distress syndrome (ARDS) or multiple organ injury syndromes secondary to septicemia, trauma or hemorrhage; reperfusion injury of myocardial or other tissues; acute glomerulonephritis; reactive arthritis; dermatoses with acute inflammatory components; acute purulent meningitis or other central nervous system inflammatory disorders such as stroke; thermal injury; hemodialysis; leukapheresis; ulcerative colitis; Crohn's disease; necrotizing enterocolitis; granulocyte transfusion associated syndromes; and cytokine-induced toxicity.

The anti-inflammatory agents of the present invention are compounds capable of specifically antagonizing the interaction of the CD-18 complex on granulocytes with endothelial cells. Such antagonists comprise: ICAM-3; a functional derivative of ICAM-3; a non-immunoglobulin antagonist of ICAM-3 other than ICAM-1, ICAM-2, or a member of the CD-18 family of molecules.

B. Suppressors of Organ and Tissue Rejection

Since ICAM-3, particularly in soluble form, is capable of acting in the same manner as an antibody to members of the CD-18 family, it may be used to suppress organ or tissue rejection caused by any of the cellular adhesion-dependent functions. Moreover, an anti-ICAM-3 antibody, functional derivatives of ICAM-3, and antagonists of ICAM-3 may also be employed to suppress such rejection.

ICAM-3 and anti-ICAM-3 antibodies can be used to prevent solid organ or tissue rejection, e.g. kidney, non-solid organ rejection, e.g. bone marrow, or modify autoimmune responses, in the mammalian subject. Importantly, the use of monoclonal antibodies capable of recognizing ICAM-3 may permit one to perform organ transplants even between individuals having HLA mismatch.

C. Adjunct to the Introduction of Antigenic Material Administered for Therapeutic or Diagnostic Purposes Immune responses to therapeutic or diagnostic agents such as, for example, bovine insulin, interferon, tissue-type plasminogen activator or murine monoclonal antibodies substantially impair the therapeutic or diagnostic value of such agents, and in some instances, causes diseases such as serum sickness. Such a situation can be remedied through the use of the antibodies of the present invention. In this embodiment of the present invention anti-ICAM-3 antibodies would be administered in combination with the therapeutic or diagnostic agent. The addition of the antibody prevents the recipient from recognizing the agent, and therefore prevents the recipient from initiating an immune response against it. The absence of such an immune response results in the ability of the patient to receive additional administrations of the therapeutic or diagnostic agent.

ICAM-3 (particularly in solubilized form) or its functional derivatives may be employed alone or in combination with ICAM-1 or ICAM-2, or with antibodies capable of binding to LFA-1, in the treatment of disease. Thus, in solubilized form, such molecules may be employed to inhibit organ or graft rejection. ICAM-3, or its functional derivatives may be used in the same manner as anti-ICAM-3 antibodies to decrease the immunogenicity of therapeutic or diagnostic agents.

D. Suppressors of Tumor Metastasis

The agents of the present invention may also be employed to suppress the metastasis of a hematopoietic tumor cell, which requires a functional member of the CD-18 family for migration. In accordance with this embodiment of the present invention, a patient in need of such treatment is provided with an amount of an agent (such as an antibody capable of binding to ICAM-3; a toxin-derivatization of said antibody; a fragment of an antibody, said fragment being capable of binding to ICAM-3; a toxin-derivatization or said fragment; substantially pure ICAM-3; a functional derivative of ICAM-3; or a non-immunoglobulin antagonist of ICAM-3 other than ICAM-1 or ICAM-2) sufficient to suppress said metastasis.

In a further embodiment of the present invention a method for suppressing the growth of an ICAM-3-expressing tumor cell is provided. Specifically, said method comprises providing to a patient in need of such treatment an amount of an agent sufficient to suppress said growth. Suitable agents include an antibody capable of binding to ICAM-3; a toxin-derivatization of said antibody; a fragment of an antibody, said fragment being capable of binding to ICAM-3; a toxin-derivatization of said fragment; a toxin-derivatized member of the CD-18 family of molecules; or a toxin-derivatized functional derivative of a member of the CD-18 family of molecules.

In a further embodiment of the present invention a method of suppressing the growth of an LFA-1-expressing tumor cell is provided. Specifically, said method comprises providing to a patient in need of such treatment an amount of a toxin sufficient to suppress said growth. Suitable toxins include a toxin-derivatized ICAM-3, or a toxin-derivatized functional derivative of ICAM-3.

E. Suppression of HIV Infection and the Prevention of the Dissemination of HIV Infected Cells.

In a further embodiment of present invention a method is provided for suppressing the infection of HIV. Specifically, said method comprises administering to an HIV-infected individual an effective amount of an HIV infection suppression agent. Although the invention is particularly concerned with a method for the suppression of HIV-1 infection, it is to be understood that the method may be applied to any HIV variant (such as, for example, HIV-2) which may infect cells in a way which may be suppressed by the agents of the present invention. Such variants are the equivalents of HIV-1 for the purposes of the present invention.

One aspect of the present invention derives from the recognition that expression of LFA-1 and, in some cases, LFA-1's binding ligand, stimulated by HIV infection, promotes cell-to-cell adherence reactions that can increase the contact time of infected with uninfected cells, facilitating transfer of virus from infected to uninfected cells. Thus agents of the present invention which are capable of modulating LFA-1/ligand interactions are able to suppress infection by HIV, and, in particular, by HIV-1. One means through which molecules which inhibit LFA-1/ligand interactions may suppress HIV infection is by impairing the ability of the LFA-1 ligand expressed by HIV-infected cells to bind to the CD11/CD18 receptors of a healthy T cell. Alternatively, molecules which inhibit LFA-1/ligand interactions may impair the ability of the CD11/CD18 receptors expressed by HIV-infected cells to bind to LFA-1 of a healthy T cell. In order to impair the ability of a cell to bind to the CD11a/CD18 receptor, or to the LFA-1 binding ligand, it is possible to employ ICAM-3, a fragment of ICAM-3, a functional derivative of ICAM-3, or anti-ICAM-3 antibodies.

The agents of the present invention are intended to be provided to recipient subjects in an amount sufficient to achieve a suppression of HIV infection. An amount is said to be sufficient to "suppress" HIV infection if the dosage, route of administration, etc. of the agent are sufficient to attenuate or prevent such HIV infection. The agents are to be provided to patients who are exposed to, or effected by HIV infection.

The agents of the present invention may be for either a "prophylactic" or "therapeutic" purpose in the treatment of HIV infection. When provided prophylactically, the agent is provided in advance of any symptom of viral infection (for example, prior to, at, or shortly after) the time of such infection, but in advance of any symptoms of such infection). The prophylactic administration of the agent serves to prevent or attenuate any subsequent HIV infection. When provided therapeutically, the agent is provided at (or shortly after) the detection of virally infected cells. The therapeutic administration of the agent serves to attenuate any additional HIV infection.

The agents of the present invention may, thus, be provided either prior to the onset of viral infection (so as to suppress the anticipated HIV infection) or after the actual detection of such virally infected cells (to suppress further infection).

In a further embodiment, the invention provides an improved therapy for AIDS, and an enhanced means for suppressing HIV infection, and particularly HIV-1 infection, which comprises the co-administration of:
(I) ICAM-3, a soluble ICAM-3 derivative, CD11 (either CD11a, CD11b, or CD11c), a soluble CD11 derivative, CD18, a soluble CD18 derivative, or a CD11/CD18 heterodimer, or a soluble derivative of a CD11/CD18 heterodimer and/or
(II) an antibody capable of binding to ICAM-3 with
(III) cell or particle associated CD4 or a soluble derivative of CD4 and/or
(IV) a molecule (preferably an antibody or antibody fragment) capable of binding to CD4.

In a further embodiment of the present invention, a method for suppressing the migration of HIV-infected cells is provided. Specifically, said method comprises administering an effective amount of an anti-migration agent to an HIV-infected individual.

The anti-migration agents of the present invention include ICAM-3, a fragment of ICAM-3, a functional derivative of ICAM-3, or anti-ICAM-3 antibodies which are capable of impairing the ability of an HIV-infected T cell to bind to a LFA-1 ligand. Antibodies which bind to ICAM-3 will suppress migration by impairing the ability of the ICAM-3 expressed by HIV-infected T cells to bind to cells expressing a CD11/CD18 receptor. In order to impair the ability of a cell to bind to the CD11a/CD18 receptor it is possible to employ an antibody capable of binding to ICAM-3.

The agents of the present invention are intended to be provided to recipient subjects in an amount sufficient to suppress the migration of HIV (or other virally) infected T cells. An amount is said to be sufficient to "suppress" migration of T cells if the dosage, route of administration, etc. of the agent are sufficient to attenuate or prevent such migration.

The administration of such compound(s) may be for either a "prophylactic" or "therapeutic" purpose. When provided prophylactically, the agents of the present invention is provided in advance of any symptom of viral infection (for example, prior to, at, or shortly after) the time of such infection, but in advance of any symptoms of such infection). The prophylactic administration of the agents serves to prevent or attenuate any subsequent migration of virally infected T cells. When provided therapeutically, the agent is provided at (or shortly after) the detection of virally infected T cells. The therapeutic administration of the agent serves to attenuate any additional migration of such T cells.

The agents of the present invention may, thus, be provided either prior to the onset of viral infection (so as to suppress the anticipated migration of infected T cells) or after the actual detection of such virally infected cells.

F. Treatment of Asthma

In a further embodiment of the present invention an agent capable of modulating LFA-1/ICAM-3 interactions is used in the treatment of asthma. Specifically, said method comprises administering an effective amount of an anti-asthma agent to an individual in need of such treatment.

The anti-asthma agents of the present invention include ICAM-3, a fragment of ICAM-3, a functional derivative of ICAM-3, or anti-ICAM-3 antibodies which are capable of impairing the ability of a cell to bind to a LFA-1. Antibodies which bind to ICAM-3 will suppress the migration of eosinophils by impairing the ability of the ICAM-3 expressed on these cells to bind to cells expressing a CD11/CD18 receptor.

The anti-asthma agents of the present invention are intended to be provided to recipient subjects in an amount sufficient to lessen or attenuate the severity, extent or duration of the asthma symptoms.

The agents of the present invention may be administered either alone or in combination with one or more additional anti-asthma agents (such as methylxanthines (such as theophylline), beta-adrenergic agonists (such as catecholamines, resorcinols, saligenins, and ephedrine), glucocorticoids (such as hydrocortisone), chromones (such as cromolyn sodium) and anticholinergics (such as atropine), in order to decrease the amount of such agents needed to treat the asthma symptoms.

The administration of the agents of the present invention may be for either a "prophylactic" or "therapeutic" purpose. When provided prophylactically, the agent is provided in advance of any asthma symptom. The prophylactic administration of the agent serves to prevent or attenuate any subsequent asthmatic response. When provided therapeutically, the agent is provided at (or shortly after) the onset of a symptom of asthma. The therapeutic administration of the agent serves to attenuate any actual asthmatic episode. The agents of the present invention may, thus, be provided either prior to the onset of an anticipated asthmatic episode (so as to attenuate the anticipated severity, duration or extent of the episode) or after the initiation of the episode.

G. Diagnostic and Prognostic Applications

Monoclonal antibodies capable of binding to ICAM-3 may be employed as a means of imaging or visualizing the sites of ICAM-3 expression and inflammation in a patient. In such a use, anti-ICAM-3 monoclonal antibodies are detectably labeled, through the use of radioisotopes, affinity labels (such as biotin, avidin, etc.), fluorescent labels, or paramagnetic atoms. Procedures for accomplishing such labeling are well known to the art. The labeled antibodies can then be used in diagnostic imaging. Clinical application of antibodies in diagnostic imaging are reviewed by Grossman, H. B., *Urol. Clin. North Amer.* 13:465–474 (1986)), Unger, E. C. et al., *Invest. Radiol.* 20:693–700 (1985)), and Khaw, B. A. et al., *Science* 209:295–297 (1980)).

The presence of ICAM-3 expression may also be detected through the use of hybridization probes, such as mRNA, cDNA, genomic DNA, or synthetic oligonucleotide probes which bind to ICAM-3 gene sequences, or to ICAM-3 mRNA sequences, present in a cell which expresses ICAM-3. Techniques for performing such hybridization assays are described by Maniatis, T. et al., In: *Molecular Cloning, a Laboratory Manual*, Coldspring Harbor, N.Y. (1982), and by Haymes, B. D. et al., In: *Nucleic Acid Hybridization, a Practical Approach*, IRL Press, Washington, D.C. (1985), which references are herein incorporated by reference.

The detection of foci of ICAM-3 expression, through the use of labeled antibodies or nucleic acid probes, can be used in the diagnosis of tumor development. In one diagnostic embodiment, samples of tissue or blood are removed from a subject and are incubated in the presence of antibodies of which are or which can be detectably labeled. In a preferred embodiment, this technique is done in a non-invasive manner through the use of magnetic imaging, fluorography, etc. Such a diagnostic test may be employed in monitoring organ transplant recipients, e.g. kidney, for early signs of potential tissue rejection. Such assays may also be conducted in efforts to determine an individual's predilection to rheumatoid arthritis or other chronic inflammatory diseases.

For example, by radioactively labeling anti-ICAM-3 antibodies or antibody fragments, it is possible to detect the antigen through the use of radioimmune assays. A good description of a radioimmune assay (RIA) may be found in *Laboratory Techniques and Biochemistry in Molecular Biology*, by Work, T. S., et al., North Holland Publishing Company, N.Y. (1978), with particular reference to the chapter entitled "An Introduction to Radioimmune Assay and Related Techniques" by Chard, T., incorporated by reference herein. Alternatively, the antibody can be labeled with a fluorescent compound, an enzyme, or other suitable labels known in the art.

In addition to localizing sites of inflammation, antibodies capable of binding to ICAM-3 can be employed to assay biological fluids for the presence of circulating ICAM-3 using any of the commonly employed mediums for fluid assays. The presence of circulating ICAM-3 in a fluid sample is indicative of an inflammatory response or other ICAM-3 mediated biological functions. Additionally, the presence of ICAM-3 in amniotic fluid is associated with complicating arising during pregnancy. Any biological fluid can be used for the assay. However, the preferred biological fluids are; blood, serum, plasma synovial fluid, amniotic fluid, spinal fluid or urine.

VIII. ADMINISTRATION OF THE COMPOSITIONS OF THE PRESENT INVENTION

The therapeutic effects of ICAM-3 may be obtained by providing to a patient the entire ICAM-3 molecule, or any therapeutically active peptide fragments thereof. Of special interest are therapeutically active peptide fragments of ICAM-3 which are soluble.

ICAM-3 and its functional derivatives may be obtained synthetically, through the use of recombinant DNA technology, by proteolysis, or by a combination of such methods. The therapeutic advantages of ICAM-3 may be augmented through the use of functional derivatives of ICAM-3 possessing additional amino acid residues added to enhance coupling to carrier or to enhance the activity of the ICAM-3. The scope of the present invention is further intended to include functional derivatives of ICAM-3 which lack certain amino acid residues, or which contain altered amino acid residues, so long as such derivatives possess or affect a biological or pharmacological activity of ICAM-3.

Both the antibodies of the present invention and the ICAM-3 molecule disclosed herein are said to be "substantially free of natural contaminants" if preparations which contain them are substantially free of materials with which these products are normally and naturally found.

The present invention extends to antibodies, and biologically active fragments thereof, (whether polyclonal or monoclonal) which are capable of binding to ICAM-3. Such antibodies may be produced either by an animal, or by tissue culture, or by recombinant DNA means.

Administration of ICAM-3, or molecules derived from ICAM-3, can be done alone or in combination with ICAM-1 and or ICAM-2. Administration of anti-ICAM-3 antibodies, or other molecules capable of binding to ICAM-3 or to molecules derived from ICAM-3, can be done alone or in combination with anti-ICAM-1 antibodies and/or anti-ICAM-2 antibodies. In providing a patient with antibodies, or antibody fragments capable of binding to ICAM-3, or when providing ICAM-3 (or a fragment, variant, or derivative thereof) to a recipient patient, the dosage of administered agent will vary depending upon such factors as the patient's age, weight, height, sex, general medical condition, previous medical history, etc. In general, it is desirable to provide the recipient with a dosage of antibody which is in the range of from about 1 pg/kg to 10 mg/kg (body weight of patient), although a lower or higher dosage may be administered. When providing ICAM-3 molecules or their functional derivatives to a patient, it is preferable to administer such molecules in a dosage which also ranges from about 1 pg/kg to 10 mg/kg (body weight of patient) although a lower or higher dosage may also be administered. As discussed below, the therapeutically effective dose can be lowered if the anti-ICAM-3 antibody is additionally administered with an anti-LFA-1 antibody, an anti-ICAM-1 antibody and/or an anti-ICAM-2 antibody. As used herein, one compound is said to be additionally administered with a second compound when the administration of the two compounds is in such proximity of time that both compounds can be detected at the same time in the patient's serum.

Both the antibody capable of binding to ICAM-3 and ICAM-3 itself may be administered to patients intravenously, intramuscularly, subcutaneously, enterally, topically or parenterally. When administering antibodies or ICAM-3 by injection, the administration may be by continuous injections, or by single or multiple boluses.

The agents of the present invention are intended to be provided to recipient subjects in an amount sufficient to "physiologically effective." An amount is said to be physiologically effective if the dosage, route of administration, etc. of the agent are sufficient to attenuate or prevent the physiological effect associated with ICAM-3. For example, one of the agents of the present invention is provided to a patient for the intention of suppressing inflammation is said to be physiologically effective if it is provided in sufficient dosage to "suppress" inflammation.

Additionally, anti-ICAM-3 antibodies, or a fragment thereof, may be administered either alone or in combination with one or more additional immunosuppressive agents (especially to a recipient of an organ or tissue transplant). The administration of such compound(s) may be for either a "prophylactic" or "therapeutic" purpose. When provided prophylactically, the immunosuppressive compound(s) are provided in advance of any inflammatory response or symptom (for example, prior to, at, or shortly after the time of an organ or tissue transplant but in advance of any symptoms of organ rejection). The prophylactic administration of the compound(s) serves to prevent or attenuate any subsequent inflammatory response (such as, for example, rejection of a transplanted organ or tissue, etc.). When provided therapeutically, the compound(s) is provided at (or shortly after) the onset of a symptom of actual inflammation (such as, for example, organ or tissue rejection). The therapeutic administration of the compound(s) serves to attenuate any actual inflammation (such as, for example, the rejection of a transplanted solid organ or tissue, say kidney or non-solid organs, say bone marrow).

The anti-inflammatory agents of the present invention may, thus, be provided either prior to the onset of inflammation (so as to suppress an anticipated inflammation) or after the initiation of inflammation.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The antibodies and the ICAM-3 molecules of the present invention can be formulated according to known methods of preparing pharmaceutically useful compositions, whereby these materials, or their functional derivatives, are combined with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)). In order to form a pharmaceutically acceptable composition suitable for effective administration, such compositions will contain an effective amount of an agent of the present invention together with a suitable amount of carrier. Additionally, the antibodies of the present invention may be humanized, through chimerization or CDR grafting, to become more "pharmacologically acceptable" to a patient. Such methods for chimerization of antibodies, specifically anti-ICAM-1 antibodies are described elsewhere, British Patent application nos. 9009548.0, 9009549.8 and PCT Application Nos. PCT/US91/02942 and PCT/US91/02946, filed at the U.S. Receiving Office on Apr. 27, 1991, herein incorporated by reference.

Additional pharmaceutical methods may be employed to control the duration of action. Control release preparations may be achieved through the use of polymers to complex or absorb the agents of the present invention. The rate and duration of the controlled delivery may be regulated to a certain extent by selecting an appropriate macromolecule matrix, by varying the concentration of macromolecules incorporated, as well as the methods of incorporation. Another possible method to control the duration of action by controlled release preparations is to incorporate the agents of the present invention into particles of a polymeric material, such as polyesters, polyamino acids, hydrogels, poly(lactic acid) or ethylene vinyl acetate copolymers. Alternatively, instead of incorporating these agents into polymeric particles, it is possible to entrap these materials in microcapsules prepared, for example, by coacervation techniques or by interfacial polymerization, by gelatine or poly (methylmethacylate) microcapsulation, or in colloidal drug delivery systems, for example, liposomes, albumin microspheres, microemulsions, nanoparticles, and nanocapsules or in macroemulsions.

The invention further includes a pharmaceutical composition comprising: (a) an anti-inflammatory agent (such as an antibody capable of binding to ICAM-3; a fragment of said antibody capable of binding to ICAM-3; ICAM-3; a functional derivative of ICAM-3; or a non-immunoglobulin antagonist of ICAM-3 other than ICAM-1 and ICAM-2, and (b) at least one immunosuppressive agent. Examples of suitable immunosuppressive agents include: dexamethasone, azathioprine and cyclosporin A.

Having now generally described the invention, the agents and methods of obtaining same will be more readily understood through reference to the following examples which are provided by way of illustration, and are not intended to be limiting of the present invention, unless specified.

EXAMPLE I

Characterization of ICAM-3, a New Adhesion Ligand for LFA-1

Adhesion of cell lines and lymphocytes, Dustin et al., Cold Spring Harbor *Symp. Quant. Biol.* 54:753–765 (1989)) to LFA-1-coated plates was performed as previously described. LFA-1 purified from JY lysates was absorbed onto 96-well microtitre plates (Linbro-titertek) at 1100 sites/$\mu m^2$. Non-specific binding sites were blocked with 1% BSA and washed with PBS/5% FBS/2 mM $MgCl_2$/0.5% HSA (assay media). Specific inhibition of LFA-1 was achieved by incubation for 30 min at RT of the microtitre wells with a $\frac{1}{200}$ dilution of TS1/22 (anti-LFA-1$\alpha$) ascites. Resting T cells were isolated from whole blood by plastic adherence and nylon wool filtration and were 91% $CD2^+$, while PHA-blasts were generated by culturing the cells in the presence of 10 $\mu g/ml$ phytohemagglutinin (PHA). Cells were labeled with the fluorochrome BCECF (Molecular Probes Inc.), washed and resuspended in assay medium. MAb pretreatment of cells consisted of incubation with $\frac{1}{200}$ dilution for ascites for 45 min at 4° C., after which $10_5$ cells were transferred to each well. Cell lines adhered to solid phase LFA-1 for 1 h at 37° C., and non-adherent cells were removed with six 23 gauge needle aspirations, while lymphocytes were spun down at 30×g for 5 min and incubated at 37° C. for 30 min. Unbound lymphocytes which were removed by flicking media from the plate 8 times with 100 $\psi$ added between each wash. Flicking as more effective for thoroughly removing unbound T lymphocytes which were more difficult to remove due to their small size. Fluorescence was directly quantitated from the 96-well plates using a fluorescence concentration analyzer (Baxte). All MAb were used at saturating concentrations (1/200 dilution of ascites), and include TS1/22 (anti-CD11a, IgG1) (Sanchez-Madrid et al., *Proc. Natl. Acad. Sci. USA* 79:7489–7493 (1982)), RR1/1 (anti-ICAM-1, IgG1) (Rothlein et al., *J. Immunol.* 137:1270–1274 (1986)), CBR-IC2/2 (anti-ICAM-2, IgG2a) (de Fougerolles et al., *J. Exp. Med.* Submitted (1991) (in press)), and CBR-IC3/1 (anti-ICAM-3, IgG1). CBR-IC3/1 was derived from the fusion of the murine myeloma P3X63Ag8.653 with spleen cells from SKW3-injected Balb/c mice (Gefter et al., *Som. Cell Gen.* 3:231–236 (1977)), and 600 hybridomas were screened for the ability to inhibit SKW3 biding to purified LFA-1. CRB-IC3/1 was shown not to react to purified LFA-1 nor to COS cells transfected with either ICAM-1, ICAM-2 or LFA-1 cDNAs (data not shown). One of four representative experiments is shown and error bars indicate one standard deviation.

EXAMPLE II

Flow Cytometric Analysis of Cellular ICAM-1, ICAM-2, and ICAM-3 Expression

Cell lines used have all been previously described Hibbs et al., *J. Clin. Invest.* 85:674–681 (1990)). Peripheral blood mononuclear cells (PBMC) were obtained by dextran sedimentation and Ficoll-Hypaque (1.077) centrifugation as described (Dustin et al., *J. Cell Biol.* 107:321–331(1988)). Neutrophils were recovered from the cell pellet and contaminating erythrocytes removed by hypotonic lysis. Lymphocytes and monocytes were separated by cytometric analysis using forward and perpendicular light scatter, and was confirmed by monocyte and T cell specific MAb. Plastic-adherence was used to enrich lymphocytes from PBMC and cells were cultured in the presence of 10 μg/ml phytohemagglutinin (PHA). Samples were analyzed using an EPICS V flow cytometer, and fluorescence quantitated using EPICS Immune-Brite fluorescent beads (Coulter) to calibrate the cytometer. Expression of ICAM-3 on resting lymphocytes was 2–3 fold greater than either CD3 or LFA-1, while monocytes expressed 3–4 fold more ICAM-3 than LFA-1. Levels of ICAM-3 expression on neutrophils was equivalent to that of Mac-1 (CD11b/CD18). Treatment of cells with phospholipase C revealed no PI-linked form of ICAM-3 existed.

TABLE 2

Relative Surface Antigen Expression of ICAMs by Immunofluorescence Flow Cytometry

| | Specific Linear Fluorescence Intensity* | | |
|---|---|---|---|
| Cell Line/Type | αICAM-1 (RR1/1) | αICAM-2 (CBR-IC2/1) | αICAM-3 (CBR-IC3/1) |
| Resting lymphocytes | 4 | 22 | 106 |
| 1 day PHA-blasts | 22 | 18 | 78 |
| 3 day PHA-blasts | 85 | 42 | 205 |
| 5 day PHA-blasts | 25 | 45 | 223 |
| Monocytes | 13 | 39 | 224 |
| Neutrophils | 1 | 0 | 213 |
| T lymphoblastoid | | | |
| SKW3 | 0 | 98 | 73 |
| Jurkat | 2 | 166 | 161 |
| Sup T | 10 | 113 | 19 |
| Molt 4 | 1 | 242 | 117 |
| B lymphoblastoid | | | |
| JY | 154 | 119 | 47 |
| SLA | 224 | 113 | 306 |
| Ramos | 132 | 136 | 112 |
| Raji | 266 | 88 | 0 |
| Monocytic | | | |
| U937 | 62 | 67 | 37 |
| HL60 | 17 | 43 | 203 |
| Melanomas | | | |
| BK | 896 | 3 | 0 |
| RPMI 7591 | 475 | 0 | 0 |
| Erythroleukemic | | | |
| K562 | 293 | 143 | 0 |
| Miscellaneous± | | | |
| HUVEC | 31 | 494 | 0 |
| Hep G2 | 1526 | 41 | 0 |
| HeLa | 1082 | | 0 |
| RD3/5 | 0 | 9 | 0 |
| FS1,2,3 | 409 | 0 | 0 |
| A-172 | 0 | 0 | 0 |

*Membrane expression determined by immunofluorescence flow cytometry as outlined in materials and methods. Values are determinative of at least two experiments. Fluorescent beads were used to calibrate the cytometer such that one unit was approximately $10^3$ fluorescein equivalents (Coulte Diagnostics, Hialeah, FL).
±Miscellaneous cell lines include: Human umbilical vein endothelial cells, huvec;; human breast carcinoma, Hep G2; human epithelioid carcinoma cell line, HeLa; human rhabdomyosarcoma, RD 3/5; human fibrosarcoma, and FS 1,2,3; human glioblastomas.

EXAMPLE III

Immunoprecipitation of ICAM-3

Surface labeling of cells with $^{125}$I was performed as described using iodogen (Kishimoto et al., *J. Biol. Chem.* 264:3588–3595 (1989)). Cells were triton X-100 (1%) lysed. The lysates were precleared with bovine IgG coupled-Sepharose, and then incubated with appropriate MAb-bound Sepharose for 2 h. Beads were washed and boiled in sample buffer containing 50 mM Tris, 1% SDS and 1% 2-mercaptoethanol. Nonreduced samples were boiled in buffer lacking 2-mercaptoethanol and treated with 20 mM iodoacetamide. Samples were analyzed on 7% vertical slab polyacrylamide gels as previously described (Laemmli, U. K., *Nature* 227:680–685 (1970)), and proteins visualized by autoradiography. Treatment of samples with N-Glycanase (Genzyme) as previously described (Tarentino et al., *Biochemistry* 24:4665–4671 (1985)), using a concentration (10 units/ml, 37° C., 18 h) was determined to give optimal cleavage of all N-linked oligosaccharides from the peptide backbone. MHC class I contains on N-linked carbohydrate, while ICAM-2 ($m_r$60,000, 6 N-linked sites, backbone of $M_r$28,383) is highly glycosylated.

EXAMPLE IV

Distribution of ICAM-3

The anti-ICAM-3 antibodies of the present invention were used to further determine the tissue distribution of the ICAM-3 protein using flow cytometry. Table 3 presents a summary of cell types which display surface expression of ICAM-3. ICAM-3's expression appears to be restricted to hemopoietic cells. The flow cytometry data was confirmed using immunohistochemical staining of tissue sections using labeled anti-ICAM-3 antibodies (data not shown). As with the flow cytometry data, immunohistochemical studies have shown that ICAM-3 expression appears to be restricted to hemopoietic cells.

TABLE 3

Relative Surface Antigen Expression of ICAMs by Immunofluorescence Flow Cytometry

|  | Specific Linear Fluorescence Intensity* | | |
| --- | --- | --- | --- |
| Cell Line/Type | αICAM-1 (RR1/1) | αICAM-2 (CBR-IC2/1) | αICAM-3 (CBR-IC3/1) |
| Resting lymphocytes | 4 | 22 | 106 |
| 1 day PHA-blasts | 22 | 18 | 78 |
| 3 day PHA-blasts | 85 | 42 | 205 |
| 5 day PHA-blasts | 25 | 45 | 223 |
| Monocytes | 13 | 39 | 224 |
| Neutrophils | 1 | 0 | 213 |
| T lymphoblastoid | | | |
| SKW3 | 0 | 98 | 273 |
| Jurkat | 2 | 166 | 161 |
| Sup T | 10 | 113 | 19 |
| Molt 4 | 1 | 242 | 117 |
| B lymphoblastoid | | | |
| JY | 154 | 119 | 47 |
| SLA | 224 | 113 | 308 |
| Ramos | 132 | 136 | 112 |
| Raji | 266 | 88 | 0 |
| Monocytic | | | |
| U937 | 62 | 67 | 37 |
| HL60 | 17 | 43 | 203 |
| Melanomas | | | |
| BK | 896 | 3 | 0 |
| RPMI 7591 | 475 | 0 | 0 |
| Erythroleukemic | | | |
| K562 | 293 | 143 | 0 |
| Miscellaneous± | | | |
| HUVEC | 31 | 494 | 0 |
| Hep G2 | 1526 | 41 | 0 |
| HeLa | 1082 | 0 | 0 |
| RD3/5 | 0 | 9 | 0 |
| FS1,2,3 | 409 | 0 | 0 |
| A-172 | 0 | 0 | 0 |

*Membrane expression determined by immunofluorescence flow cytometry as outlined in materials and methods. Values are determinative of at least two experiments. Fluorescent beads were used to calibrate the cytometer such that one unit was approximately $10^3$ fluorescein equivalents (Coulte Diagnostics, Hialeah, FL).
±Miscellaneous cell lines include: Human umbilical vein endothelial cells, huvec;; human breast carcinoma, Hep G2; human epithelioid carcinoma cell line, HeLa; human rhabdomyosarcoma, RD 3/5; human fibrosarcoma, and FS 1,2,3; human glioblastomas.

EXAMPLE V

Purification of ICAM-3

ICAM-3 was purified using immunoaffinity chromatography in which an anti-ICAM-3 antibody CBR-IC3/1 was immobilized on a matrix using methods known in the art. Numerous sources have been used as starting material for isolating ICAM-3. These include, but are not limited to SKW3, a human thymoma cell line, and human tonsil. The methods utilized in purifying ICAM-3 are essentially those described by deFougerolles et al., in *J. Exp. Med.* 175:185–190 (1992). One-skilled in the art will recognize that washing and elution regimes (reagent vary slightly with each antigen to be purified and with each antibody to be used in immunoaffinity chromatography.

As noted below, ICAM-3 purified from SKW3 cells or human tonsilar cells appears to have a molecular weight from about 120 to 124 kD, while ICAM-3 purified from neutrophil derived-lysates yielded a broad band displaying a molecular weight from about 120 to 150 kD.

ICAM-3 purified in this fashion has been shown to maintain its ability to bind anti-ICAM-3 antibodies, and LFA-1 on a variety of cells (FIGS. 6 and 7).

EXAMPLE VI

Identification of Various Molecular Weights of ICAM-3

Immunoprecipitation and analysis by polyacrylamide gel electrophoresis was used to determined the molecular weight of ICAM-3 on various cell types. The molecular weight of ICAM-3 immunoprecipitated from neutrophils was found to be different from that immunoprecipitated from lymphocytes. ICAM-3 isolated from lymphocyte and lymphoid cell lines appears as a band with a molecular weight from about 120 to 124 kD. The molecular weight of ICAM-3 isolated from neutrophils is slightly higher than that expressed by lymphoid cells, appearing as a diffuse band from about 120 to 150 kD. FIG. 4.

Such a variation in size is not uncommon in members of the ICAM family of glycoproteins. ICAM-1 demonstrates a similar ariation in molecular weight among different cell types. The variation in molecular weight seen fro ICAM-1 has been shown to be caused by variations in the extent of glycosylation. Therefore, the variations in the molecular weight of ICAM-3 is most likely caused by differences in glycosylation. One skilled in the art can readily confirm this by subjecting ICAM-3 isolated from neutrophils to various glycosidases and other enzymatic treatments and looking at the effect this has on the molecular weight.

Variations in the extent of glycosylation of ICAM-1 have been shown to affect MAC-1 (CD11b/CD18) binding. Therefore, by varying the extent of glycosylation of ICAM-3, it is possible to generate ICAM-3 derivatives that have modified affinities for binding to the various ligands of ICAM-3, for example, members of the CD11/CD18 family of glycoproteins.

EXAMPLE VII

ICAM-3 Antibodies

Mice were injected with a combination of adjuvant and ICAM-3 protein which was purified from SKW3 or tonsil cells as described above. Monoclonal antibodies from immunized animals were generated using procedures known in the art.

Table 4 presents a summary of the various anti-ICAM-3 antibodies obtained. The various antibodies were identified on the basis of their ability to react by ELISA to purified immobilize ICAM-3. Positive mAb were then screened on various cell lines known to be ICAM-3 positive and then immunoprecipitated from radiolabeled ICAM-3 positive cell lysates. The mAbs were also tested for their ability to block PMA-induced SKW3 cell aggregation in the presence of anti-ICAM-1 and anti-ICAM-2 antibodies. Alternatively, anti-ICAM-3 antibodies can be identified by their ability to inhibit binding of SKW3 cells to immobilized purified ICAM-3.

One of the lines of evidence that a third ligand of LFA-1 existed was the presence of a ICAM-1/ICAM2 independent pathway for PMA-stimulated SKW3 cell aggregation. We were able to block this aggregation with either mouse anti-ICAM-3 polyclonal antisera or with a combination of CBR-IC3/1 and CBR-IC3/2.

TABLE 4

| | | ICAM-3 mABs | |
| --- | --- | --- | --- |
| | | PMA-induced | Aggregation* |
| mAb | Isotype | Alone | + ICI + 2 mAb | + ICI + 2 + IC3/1 mAb |
| CBR-1C3/2 | IgG2a, k | 3 | 2 | 0 |
| CBR-1C3/3 | IgG2a, k | 4 | 3 | 2 |
| CBR-1C3/4 | IgM, k | 4 | 3 | 2–3 |
| CBR-1C3/5 | IgG2a, k | 2 | 2 | 0–1 |
| CBR-1C3/6 | N.D. | 5 | 5 | 5 |
| ICAM-3 antisera | | 3 | 0 | 0 |
| CBR-1C3/1 | IgG1, k | 5 | 4 | — |
| HP2/19** | | | 1 | |

*Refers to scale of aggregation in J. Exp. Med. 1991 paper O = No aggregation
**Another ICAM-3 mAb from lab in Spain (F. Sanchez-Madrid). Another presentation of our results it reminded them of a mAb they had made but never characterized. It turns out to be ICAM-3.
CBR-1C3/2, 3/3, 3/5 immunoprecipitate same 120 kD band as does CBR-IC3/1. Testing mAbs for ability to western blot.

EXAMPLE VIII

Immunological Assays With Anti-ICAM-3 Antibodies

An anti-ICAM-1 antibody (RR1/1), and anti-ICAM-2 antibody (CBR-IC2/2) and anti-ICAM-3 antibodies (a combination of CBR-IC3/1 and CBR-IC3/2) were tested for their ability to block (1) PMA-stimulated SKW3 cell adhesion to purified ICAM's; (2) phytohemagglutinin (PHA) stimulation of cell division, and (3) the mixed lymphocyte response (MLR).

It has previously been shown that PMA can activate LFA-1 thus increasing it's ability to bind to ICAM-1. (Dustin et al., Nature 341:619 (1989)). FIG. 5 demonstrates that a similar activation mechanism is present in LFA-1/ICAM-3 binding.

The ability of various antibodies to block the binding of PMA stimulated SKW3 cells to purified ICAM-1 and ICAM-3 was examined. FIG. 6. The antibodies CBR-IC3/1 and CBR-IC3/2, when present individually, do not effectively block the binding of PMA stimulated SKW3 cells to purified ICAM-3. However, PMA stimulated SKW3 cell binding to ICAM-3 can be blocked using a combination of these two antibodies. As noted by deFougerolles in J. Exp. Med., the CBR-IC/3/1 monoclonal antibody by itself was capable of blocking the binding of ICAM-3 to purified LFA-1.

The binding of PMA stimulated SKW3 cells to ICAM-3 as further analyzed to determine if it was temperature dependent and cation dependent. As with ICAM-1, ICAM-3/LFA-1 binding was found to be both temperature (see FIG. 8) and cation dependent (data not shown).

FIG. 9 shows a summary of the effects of various antibodies on PHA stimulation of cell division. As noted previously (Krensky et al., J. Immunol. 131:611–616 (1983)). PHA stimulates cell proliferation in a manner that is inhibitable with anti-LFA-1 in anti-ICAM-1 antibodies, anti-ICAM-2 antibodies, or a combination of anti-ICAM-1 and anti-ICAM-2 antibodies had little effect on PHA stimulated cell division. However, a combination of 1) anti-ICAM- 1, anti-ICAM-2, and anti-ICAM-3 antibodies, 2) two anti-ICAM-3 antibodies (IC3/1 and IC3/2), and 3) anti-ICAM-1 and anti-ICAM-3 antibodies were effective at blocking PHA stimulated cell division.

EXAMPLE IX

Mixed Lymphocyte Reaction

The MLR assay is used to assess immunologic reactivity. The assay basically involves adding chemically fixed foreign cells (the stimulator cells) to a solution containing PBL's from a different individual (responder cells) and measuring the level of responsiveness, using the proliferation of the responder cells as an index and has been described previously. (Krensky et at., J. Immunol. 131:611–616 (1983)). This assay is the first step in identifying composition useful for treating graft rejection.

The effects of various antibodies and antibody combinations on the MLR reactions is presented in FIG. 10. In summary, anti-ICAM-3 alone displayed a low level effect. However, a greater level of effectiveness at blocking the MLR was found to occur with a combination of anti-ICAM-1 and anti-ICAM-3 antibodies. The highest response obtained was with the combination of anti-ICAM-1, anti-ICAM-2, and anti-ICAM-3 antibodies.

EXAMPLE X

Peptide Sequences of ICAM-3

ICAM-3 was purified from human tonsil cells by immunoaffinity chromatography as described in Example 5. The purified ICAM-3 was enzymatically digested with the Lys-C enzyme, using known methods, and peptide fragments were resolved by HPLC. FIG. 11 presents a gas chromatography of the various protein peaks observed in a typical digestion. Peaks 10 and 17 were identified as containing peptide fragments of sufficient size and structure to be sequenced (hereinafter the NK-10 and NK-17 peptide respectively).

The amino acid sequence of the NK-17 and NK-10 peptide was determined using standard procedures. The sequences of the NK-10 protein was found to be KIDRATCPQHLK (Amino Acids 401–412 of SEQ ID NO. 6). The first lysine (K) residue depicted in the sequence was inferred to be present since Lys-C cleaves proteins after lysine residues.

The sequence of the NK-17 peptide was found to be KIALETSLSK (Amino Acids 62–71 of SEQ ID No. 6). As with the NK-10 protein, the first lysine residue was inferred and later confirmed using DNA sequence analysis.

A sequence comparison of the NK-10 and NK-17 proteins with known ICAM-1 and ICAM-2 sequences revealed a high degree of homology. The NK-17 peptide shows significant homology to sequences contained in the first Ig domain of ICAM-2. The NK-10 peptide shows weak homology to sequences with domain 4 of ICAM-1.

EXAMPLE XI cDNA Cloning of ICAM-3

Degenerate oligonucleotide probes were generated based on the peptide sequences obtained above. The probes were further designed to include previously identified codon preferences observed within the ICAM-1 and ICAM-2 nucleotide sequences. The nucleotide sequences of the probe based on the amino acid sequence of the NK-17 and NK-10 proteins, is as follows:

```
                              G         (SEQ. ID NO. 13)
     G               A    A   T
5'- AAN—GAN—GTC—TCC—AGG—GCT—ATC—TT -3'
```

NK-17 probe. Oligo 23 mer with 24-fold degeneracy containing 2Ns (inosine).

```
         G   C      A              (SEQ. ID NO. 14)
5'- TTN—AGA—TGT—TGN—GGG—CAN—GTN—GCN—C 3'
```

NK-10 probe. 24 mer with 8 fold degeneracy containing 5 N's (inosine).

A cDNA expression library was generated from tonsil RNA as previously described. (Wong et al., *Proc. Natl. Acad. Sci. USA* 82:7711–7716 (1985)). The library was screened using the NK-17 probe and plaques displaying positive hybridization were rescreened using the NK-10 probe. One clone, clone 11.2, was found to have an insert from about 1.6 to 1.8 kb in length. A diagrammatic representation of clone 11.2 and the location of the NK-10 and NK-17 peptides is depicted in FIG. 12.

The ends of the insert were sequenced using procedures known in the art utilizing primers derived from the adjoining vector, while the NK-10 probe was used as an internal sequencing primer. Thus far obtained presents sequences which have been on one strand only. One skilled in the art will readily recognize that such a sequence can be validated with routine experimentation.

A summary of the sequences obtained are presented in FIG. 18. Several things should be noted in the sequence. First, a sequence with a high degree of homology with the transmembrane region of ICAM-1 has been identified. Therefore, one wishing to produce soluble fragments of ICAM-3 would thus delete all sequences after the start of the transmembrane region noted in FIG. 12. Second, the sequence obtained from the 5' end of the clone 11.2 is likely close to the 5' end of the naturally occurring gene as inferred by sequence homologies which exist between ICAM-1, ICAM-2 and ICAM-3.

EXAMPLE XII

Sequence Homology Between the Various ICAM Molecules

The nucleotide and amino acid sequence of the NK-10 and NK-17 peptides as well as the nucleotide sequences obtained above were compared with the known sequences of ICAM-1 and ICAM-2 (FIGS. 13–17).

The results indicate that ICAM-3 shows a high level of homology to both ICAM-1 and ICAM-2. Sequence homologies between ICAM-1 and ICAM-3 are found within the first (FIG. 16) and the fourth/fifth domains of ICAM-1 as well as the transmembrane domain and some of the cytoplasmic domain of ICAM-1 (FIGS. 13 and 14). Additional searches of the gene bank database reveal no other sequence which identical or similar to that obtained for ICAM-3. Significant homology were also seen between ICAM-3 and the first domains of ICAM-2 (FIG. 17).

Clone 11.2 was used to further screen libraries. Additional clones were found to obtain cDNA insets from about 2 to 2.4 kD. In all likelihood these represent full-length cDNA clones since nothing of larger size have thus far been identified.

---

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 189 base pairs
        ( B ) TYPE: nucleic acid
        ( C ) STRANDEDNESS: both
        ( D ) TOPOLOGY: both ( i i ) MOLECULE TYPE: DNA (genomic)

( i x ) FEATURE:
        ( A ) NAME/KEY: CDS
        ( B ) LOCATION: 2..187

( x i ) SEQUENCE DESCRIPTION: SEQ ID NO:1:

```
C  CCA  TTG  AGG  GGT  TCC  ACA  GTG  ACC  GTG  AGT  TGC  ATG  GCT  GGG  GCT              46
   Pro  Leu  Arg  Gly  Ser  Thr  Val  Thr  Val  Ser  Cys  Met  Ala  Gly  Ala
   1                  5                       10                      15

CGA  GTC  CAG  GTC  ACG  CTG  GAC  GGA  GTT  CCG  GCC  GCG  GCC  CCG  GGG  CAG           94
Arg  Val  Gln  Val  Thr  Leu  Asp  Gly  Val  Pro  Ala  Ala  Ala  Pro  Gly  Gln
                     20                       25                      30

CCA  GCT  CAA  CTT  CAG  CTA  AAT  GCT  ACC  GAG  AGT  GAC  GAC  GGA  CGC  AGC          142
Pro  Ala  Gln  Leu  Gln  Leu  Asn  Ala  Thr  Glu  Ser  Asp  Asp  Gly  Arg  Ser
                     35                       40                      45

TTC  TTC  TGC  AGT  GCC  ACT  CTC  GAG  GTG  CAC  GGC  CAG  TTC  TTG  CAG              187
Phe  Phe  Cys  Ser  Ala  Thr  Leu  Glu  Val  His  Gly  Gln  Phe  Leu  Gln
```

```
                              50                       55                         60
A G                                                                                                         189
```

( 2 ) INFORMATION FOR SEQ ID NO:2:

( i ) SEQUENCE CHARACTERISTICS:
        ( A ) LENGTH: 62 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Pro  Leu  Arg  Gly  Ser  Thr  Val  Thr  Val  Ser  Cys  Met  Ala  Gly  Ala  Arg
 1                  5                        10                       15

Val  Gln  Val  Thr  Leu  Asp  Gly  Val  Pro  Ala  Ala  Ala  Pro  Gly  Gln  Pro
               20                       25                       30

Ala  Gln  Leu  Gln  Leu  Asn  Ala  Thr  Glu  Ser  Asp  Asp  Gly  Arg  Ser  Phe
          35                       40                       45

Phe  Cys  Ser  Ala  Thr  Leu  Glu  Val  His  Gly  Gln  Phe  Leu  Gln
     50                       55                       60
```

( 2 ) INFORMATION FOR SEQ ID NO:3:

( i ) SEQUENCE CHARACTERISTICS:
        ( A ) LENGTH: 113 base pairs
        ( B ) TYPE: nucleic acid
        ( C ) STRANDEDNESS: both
        ( D ) TOPOLOGY: both ( i i ) MOLECULE TYPE: DNA (genomic)

( i x ) FEATURE:
        ( A ) NAME/KEY: CDS
        ( B ) LOCATION: 1..111

( x i ) SEQUENCE DESCRIPTION: SEQ ID NO:3:

```
ACT  TTG  TCC  CCG  GTC  TTC  GTG  GCG  GTG  TTA  CTG  ACC  CTG  GGC  GTG  GTG     48
Thr  Leu  Ser  Pro  Val  Phe  Val  Ala  Val  Leu  Leu  Thr  Leu  Gly  Val  Val
               65                       70                       75

ACT  ATC  GTA  CTG  GCC  TTA  ATG  TAC  GTC  TTC  AGG  GAG  CAC  CAA  CGG  AGC     96
Thr  Ile  Val  Leu  Ala  Leu  Met  Tyr  Val  Phe  Arg  Glu  His  Gln  Arg  Ser
          80                       85                       90

GGC  AGT  TAC  CAT  GTT  AG                                                        113
Gly  Ser  Tyr  His  Val
 95
```

( 2 ) INFORMATION FOR SEQ ID NO:4:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Thr  Leu  Ser  Pro  Val  Phe  Val  Ala  Val  Leu  Leu  Thr  Leu  Gly  Val  Val
 1                  5                        10                       15

Thr  Ile  Val  Leu  Ala  Leu  Met  Tyr  Val  Phe  Arg  Glu  His  Gln  Arg  Ser
               20                       25                       30

Gly  Ser  Tyr  His  Val
          35
```

( 2 ) INFORMATION FOR SEQ ID NO:5:

( i ) SEQUENCE CHARACTERISTICS:
    ( A ) LENGTH: 1817 base pairs
    ( B ) TYPE: nucleic acid
    ( C ) STRANDEDNESS: both
    ( D ) TOPOLOGY: both ( i i ) MOLECULE TYPE: DNA (genomic)

( i x ) FEATURE:
    ( A ) NAME/KEY: CDS
    ( B ) LOCATION: 9..1649

( x i ) SEQUENCE DESCRIPTION: SEQ ID NO:5:

| | | | | | | | | | | | | | | | | |
|---|---|---|---|---|---|---|---|---|---|---|---|---|---|---|---|---|
| CTGTCAGA | ATG | GCC | ACC | ATG | GTA | CCA | TCC | GTG | TTG | TGG | CCC | AGG | GCC | TGC | | 50 |
| | Met | Ala | Thr | Met | Val | Pro | Ser | Val | Leu | Trp | Pro | Arg | Ala | Cys | | |
| | | | 40 | | | | 45 | | | | | 50 | | | | |
| TGG | ACT | CTG | CTG | GTC | TGC | TGT | CTG | CTG | ACC | CCA | GGT | GTC | CAG | GGG | CAG | 98 |
| Trp | Thr | Leu | Leu | Val | Cys | Cys | Leu | Leu | Thr | Pro | Gly | Val | Gln | Gly | Gln | |
| | | | 55 | | | | 60 | | | | | 65 | | | | |
| GAG | TTC | CTT | TTG | CGG | GTG | GAG | CCC | CAG | AAC | CCT | GTG | CTC | TCT | GCT | GGA | 146 |
| Glu | Phe | Leu | Leu | Arg | Val | Glu | Pro | Gln | Asn | Pro | Val | Leu | Ser | Ala | Gly | |
| | | 70 | | | | | 75 | | | | | 80 | | | | |
| GGG | TCC | CTG | TTT | GTG | AAC | TGC | AGT | ACT | GAT | TGT | CCC | AGC | TCT | GAG | AAA | 194 |
| Gly | Ser | Leu | Phe | Val | Asn | Cys | Ser | Thr | Asp | Cys | Pro | Ser | Ser | Glu | Lys | |
| | 85 | | | | | 90 | | | | | 95 | | | | | |
| ATC | GCC | TTG | GAG | ACG | TCC | CTA | TCA | AAG | GAG | CTG | GTG | GCC | AGT | GGC | ATG | 242 |
| Ile | Ala | Leu | Glu | Thr | Ser | Leu | Ser | Lys | Glu | Leu | Val | Ala | Ser | Gly | Met | |
| 100 | | | | | 105 | | | | 110 | | | | | 115 | | |
| GGC | TGG | GCA | GCC | TTC | AAT | CTC | AGC | AAC | GTG | ACT | GGC | AAC | AGT | CGG | ATC | 290 |
| Gly | Trp | Ala | Ala | Phe | Asn | Leu | Ser | Asn | Val | Thr | Gly | Asn | Ser | Arg | Ile | |
| | | | | 120 | | | | | 125 | | | | | 130 | | |
| CTC | TGC | TCA | GTG | TAC | TGC | AAT | GGC | TCC | CAG | ATA | ACA | GGC | TCC | TCT | AAC | 338 |
| Leu | Cys | Ser | Val | Tyr | Cys | Asn | Gly | Ser | Gln | Ile | Thr | Gly | Ser | Ser | Asn | |
| | | | 135 | | | | 140 | | | | | 145 | | | | |
| ATC | ACC | GTG | TAC | GGG | CTC | CCG | GAG | CGT | GTG | GAG | CTG | GCA | CCC | CTG | CCT | 386 |
| Ile | Thr | Val | Tyr | Gly | Leu | Pro | Glu | Arg | Val | Glu | Leu | Ala | Pro | Leu | Pro | |
| | | 150 | | | | | 155 | | | | | 160 | | | | |
| CCT | TGG | CAG | CCG | GTG | GGC | CAG | AAC | TTC | ACC | CTG | CGC | TGC | CAA | GTG | GAG | 434 |
| Pro | Trp | Gln | Pro | Val | Gly | Gln | Asn | Phe | Thr | Leu | Arg | Cys | Gln | Val | Glu | |
| | 165 | | | | | 170 | | | | | 175 | | | | | |
| GGT | GGG | TCG | CCC | CGG | ACC | AGC | CTC | ACG | GTG | GTG | CTG | CTT | CGC | TGG | GAG | 482 |
| Gly | Gly | Ser | Pro | Arg | Thr | Ser | Leu | Thr | Val | Val | Leu | Leu | Arg | Trp | Glu | |
| 180 | | | | | 185 | | | | | 190 | | | | | 195 | |
| GAG | GAG | CTG | AGC | CGG | CAG | CCC | GCA | GTG | GAG | GAG | CCA | GCG | GAG | GTC | ACT | 530 |
| Glu | Glu | Leu | Ser | Arg | Gln | Pro | Ala | Val | Glu | Glu | Pro | Ala | Glu | Val | Thr | |
| | | | | 200 | | | | | 205 | | | | | 210 | | |
| GCC | ACT | GTG | CTG | GCC | AGC | AGA | GAC | GAC | CAC | GGA | GCC | CCT | TTC | TCA | TGC | 578 |
| Ala | Thr | Val | Leu | Ala | Ser | Arg | Asp | Asp | His | Gly | Ala | Pro | Phe | Ser | Cys | |
| | | | 215 | | | | 220 | | | | | 225 | | | | |
| CGC | ACA | GAA | CTG | GAC | ATG | CAG | CCC | CAG | GGG | CTG | GGA | CTG | TTC | GTG | AAC | 626 |
| Arg | Thr | Glu | Leu | Asp | Met | Gln | Pro | Gln | Gly | Leu | Gly | Leu | Phe | Val | Asn | |
| | | 230 | | | | | 235 | | | | | 240 | | | | |
| ACC | TCA | GCC | CCC | CGC | CAG | CTC | CGA | ACC | TTT | GTC | CTG | CCC | GTG | ACC | CCC | 674 |
| Thr | Ser | Ala | Pro | Arg | Gln | Leu | Arg | Thr | Phe | Val | Leu | Pro | Val | Thr | Pro | |
| | 245 | | | | | 250 | | | | | 255 | | | | | |
| CCG | CGC | CTC | GTG | GCC | CCC | CGG | TTC | TTG | GAG | GTG | GAA | ACG | TCG | TGG | CCG | 722 |
| Pro | Arg | Leu | Val | Ala | Pro | Arg | Phe | Leu | Glu | Val | Glu | Thr | Ser | Trp | Pro | |
| 260 | | | | | 265 | | | | | 270 | | | | | 275 | |
| GTG | GAC | TGC | ACC | CTA | GAC | GGG | CTT | TTT | CCA | GCC | TCA | GAG | GCC | CAG | GTC | 770 |
| Val | Asp | Cys | Thr | Leu | Asp | Gly | Leu | Phe | Pro | Ala | Ser | Glu | Ala | Gln | Val | |
| | | | | 280 | | | | | 285 | | | | | 290 | | |
| TAC | CTG | GCG | CTG | GGG | GAC | CAG | ATG | CTG | AAT | GCG | ACA | GTC | ATG | AAC | CAC | 818 |

```
                Tyr  Leu  Ala  Leu  Gly  Asp  Gln  Met  Leu  Asn  Ala  Thr  Val  Met  Asn  His
                               295                 300                      305

GGG  GAC  ACG  CTA  ACG  GCC  ACA  GCC  ACA  GCC  ACG  GCG  CGC  GCG  GAT  CAG              866
Gly  Asp  Thr  Leu  Thr  Ala  Thr  Ala  Thr  Ala  Thr  Ala  Arg  Ala  Asp  Gln
          310                      315                           320

GAG  GGT  GCC  CGG  GAG  ATC  GTC  TGC  AAC  GTG  ACC  CTA  GGG  GGC  GAG  AGA              914
Glu  Gly  Ala  Arg  Glu  Ile  Val  Cys  Asn  Val  Thr  Leu  Gly  Gly  Glu  Arg
     325                      330                           335

CGG  GAG  GCC  CGG  GAG  AAC  TTG  ACG  GTC  TTT  AGC  TTC  CTA  GGA  CCC  ATT              962
Arg  Glu  Ala  Arg  Glu  Asn  Leu  Thr  Val  Phe  Ser  Phe  Leu  Gly  Pro  Ile
340                      345                      350                           355

GTG  AAC  CTC  AGC  GAG  CCC  ACC  GCC  CAT  GAG  GGG  TCC  ACA  GTG  ACC  GTG             1010
Val  Asn  Leu  Ser  Glu  Pro  Thr  Ala  His  Glu  Gly  Ser  Thr  Val  Thr  Val
                    360                      365                           370

AGT  TGC  ATG  GCT  GGG  GCT  CGA  GTC  CAG  GTC  ACG  CTG  GAC  GGA  GTT  CCG             1058
Ser  Cys  Met  Ala  Gly  Ala  Arg  Val  Gln  Val  Thr  Leu  Asp  Gly  Val  Pro
               375                      380                      385

GCC  GCG  GCC  CCG  GGG  CAG  CCA  GCT  CAA  CTT  CAG  CTA  AAT  GCT  ACC  GAG             1106
Ala  Ala  Ala  Pro  Gly  Gln  Pro  Ala  Gln  Leu  Gln  Leu  Asn  Ala  Thr  Glu
          390                      395                           400

AGT  GAC  GAC  GGA  CGC  AGC  TTC  TTC  TGC  AGT  GCC  ACT  CTC  GAG  GTG  GAC             1154
Ser  Asp  Asp  Gly  Arg  Ser  Phe  Phe  Cys  Ser  Ala  Thr  Leu  Glu  Val  Asp
     405                      410                           415

GGC  GAG  TTC  TTG  CAC  AGG  AAC  AGT  AGC  GTC  CAG  CTG  CGA  GTC  CTG  TAT             1202
Gly  Glu  Phe  Leu  His  Arg  Asn  Ser  Ser  Val  Gln  Leu  Arg  Val  Leu  Tyr
420                      425                      430                           435

GGT  CCC  AAA  ATT  GAC  CGA  GCC  ACA  TGC  CCC  CAG  CAC  TTG  AAA  TGG  AAA             1250
Gly  Pro  Lys  Ile  Asp  Arg  Ala  Thr  Cys  Pro  Gln  His  Leu  Lys  Trp  Lys
                    440                      445                           450

GAT  AAA  ACG  AGA  CAC  GTC  CTG  CAG  TGC  CAA  GCC  AGG  GGC  AAC  CCG  TAC             1298
Asp  Lys  Thr  Arg  His  Val  Leu  Gln  Cys  Gln  Ala  Arg  Gly  Asn  Pro  Tyr
               455                      460                      465

CCC  GAG  CTG  CGG  TGT  TTG  AAG  GAA  GGC  TCC  AGC  CGG  GAG  GTG  CCG  GTG             1346
Pro  Glu  Leu  Arg  Cys  Leu  Lys  Glu  Gly  Ser  Ser  Arg  Glu  Val  Pro  Val
          470                      475                      480

GGG  ATC  CCG  TTC  TTC  GTC  AAC  GTA  ACA  CAT  AAT  GGT  ACT  TAT  CAG  TGC             1394
Gly  Ile  Pro  Phe  Phe  Val  Asn  Val  Thr  His  Asn  Gly  Thr  Tyr  Gln  Cys
485                      490                      495

CAA  GCG  TCC  AGC  TCA  CGA  GGC  AAA  TAC  ACC  CTG  GTC  GTG  GTG  ATG  GAC             1442
Gln  Ala  Ser  Ser  Ser  Arg  Gly  Lys  Tyr  Thr  Leu  Val  Val  Val  Met  Asp
500                      505                      510                           515

ATT  GAG  GCT  GGG  AGC  TCC  CAC  TTT  GTC  CCC  GTC  TTC  GTG  GCG  GTG  TTA             1490
Ile  Glu  Ala  Gly  Ser  Ser  His  Phe  Val  Pro  Val  Phe  Val  Ala  Val  Leu
                    520                      525                           530

CTG  ACC  CTG  GGC  GTG  GTG  ACT  ATC  GTA  CTG  GCC  TTA  ATG  TAC  GTC  TTC             1538
Leu  Thr  Leu  Gly  Val  Val  Thr  Ile  Val  Leu  Ala  Leu  Met  Tyr  Val  Phe
               535                      540                      545

AGG  GAG  CAC  CAA  CGG  AGC  GGC  AGT  TAC  CAT  GTT  AGG  GAG  GAG  AGC  ACC             1586
Arg  Glu  His  Gln  Arg  Ser  Gly  Ser  Tyr  His  Val  Arg  Glu  Glu  Ser  Thr
          550                      555                      560

TAT  CTG  CCC  CTC  ACG  TCT  ATG  CAG  CCG  ACA  GAA  GCA  ATG  GGG  GAA  GAA             1634
Tyr  Leu  Pro  Leu  Thr  Ser  Met  Gln  Pro  Thr  Glu  Ala  Met  Gly  Glu  Glu
     565                      570                      575

CCG  TCC  AGA  GCT  GAG  TGACGCTGGG  ATCCGGGATC  AAAGTTGGCG  GGGGCTTGGC                    1689
Pro  Ser  Arg  Ala  Glu
580

TGTGCCCTCA  GATTCCGCAC  CAATAAAGCC  TTCAAACTCC  CTAAAAAAAA  AAAAAAAAAA                     1749

AAAAAAAAAA  AAAAAAAAAA  AAAAAAAAAA  AAAAAAAAAA  AAAAAAAAAA  AAAAAAAAAA                     1809

AAAAAAAA                                                                                   1817
```

( 2 ) INFORMATION FOR SEQ ID NO:6:

( i ) SEQUENCE CHARACTERISTICS:
    ( A ) LENGTH: 547 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

```
Met Ala Thr Met Val Pro Ser Val Leu Trp Pro Arg Ala Cys Trp Thr
 1               5                   10                  15

Leu Leu Val Cys Cys Leu Leu Thr Pro Gly Val Gln Gly Gln Glu Phe
             20                  25                  30

Leu Leu Arg Val Glu Pro Gln Asn Pro Val Leu Ser Ala Gly Gly Ser
         35                  40                  45

Leu Phe Val Asn Cys Ser Thr Asp Cys Pro Ser Ser Glu Lys Ile Ala
     50                  55                  60

Leu Glu Thr Ser Leu Ser Lys Glu Leu Val Ala Ser Gly Met Gly Trp
 65                  70                  75                  80

Ala Ala Phe Asn Leu Ser Asn Val Thr Gly Asn Ser Arg Ile Leu Cys
                 85                  90                  95

Ser Val Tyr Cys Asn Gly Ser Gln Ile Thr Gly Ser Ser Asn Ile Thr
             100                 105                 110

Val Tyr Gly Leu Pro Glu Arg Val Glu Leu Ala Pro Leu Pro Pro Trp
         115                 120                 125

Gln Pro Val Gly Gln Asn Phe Thr Leu Arg Cys Gln Val Glu Gly Gly
     130                 135                 140

Ser Pro Arg Thr Ser Leu Thr Val Val Leu Leu Arg Trp Glu Glu Glu
145                 150                 155                 160

Leu Ser Arg Gln Pro Ala Val Glu Glu Pro Ala Glu Val Thr Ala Thr
                 165                 170                 175

Val Leu Ala Ser Arg Asp Asp His Gly Ala Pro Phe Ser Cys Arg Thr
             180                 185                 190

Glu Leu Asp Met Gln Pro Gln Gly Leu Gly Leu Phe Val Asn Thr Ser
         195                 200                 205

Ala Pro Arg Gln Leu Arg Thr Phe Val Leu Pro Val Thr Pro Pro Arg
     210                 215                 220

Leu Val Ala Pro Arg Phe Leu Glu Val Glu Thr Ser Trp Pro Val Asp
225                 230                 235                 240

Cys Thr Leu Asp Gly Leu Phe Pro Ala Ser Glu Ala Gln Val Tyr Leu
                 245                 250                 255

Ala Leu Gly Asp Gln Met Leu Asn Ala Thr Val Met Asn His Gly Asp
             260                 265                 270

Thr Leu Thr Ala Thr Ala Thr Ala Thr Ala Arg Ala Asp Gln Glu Gly
         275                 280                 285

Ala Arg Glu Ile Val Cys Asn Val Thr Leu Gly Gly Glu Arg Arg Glu
     290                 295                 300

Ala Arg Glu Asn Leu Thr Val Phe Ser Phe Leu Gly Pro Ile Val Asn
305                 310                 315                 320

Leu Ser Glu Pro Thr Ala His Glu Gly Ser Thr Val Thr Val Ser Cys
                 325                 330                 335

Met Ala Gly Ala Arg Val Gln Val Thr Leu Asp Gly Val Pro Ala Ala
             340                 345                 350

Ala Pro Gly Gln Pro Ala Gln Leu Gln Leu Asn Ala Thr Glu Ser Asp
```

|     |     |     | 355 |     |     |     | 360 |     |     |     | 365 |     |     |     |
| --- | --- | --- | --- | --- | --- | --- | --- | --- | --- | --- | --- | --- | --- | --- |
| Asp | Gly | Arg | Ser | Phe | Phe | Cys | Ser | Ala | Thr | Leu | Glu | Val | Asp | Gly | Glu |
|     | 370 |     |     |     |     | 375 |     |     |     |     | 380 |     |     |     |
| Phe | Leu | His | Arg | Asn | Ser | Ser | Val | Gln | Leu | Arg | Val | Leu | Tyr | Gly | Pro |
| 385 |     |     |     |     | 390 |     |     |     |     | 395 |     |     |     |     | 400 |
| Lys | Ile | Asp | Arg | Ala | Thr | Cys | Pro | Gln | His | Leu | Lys | Trp | Lys | Asp | Lys |
|     |     |     |     | 405 |     |     |     |     | 410 |     |     |     |     | 415 |     |
| Thr | Arg | His | Val | Leu | Gln | Cys | Gln | Ala | Arg | Gly | Asn | Pro | Tyr | Pro | Glu |
|     |     |     | 420 |     |     |     |     | 425 |     |     |     |     | 430 |     |     |
| Leu | Arg | Cys | Leu | Lys | Glu | Gly | Ser | Ser | Arg | Glu | Val | Pro | Val | Gly | Ile |
|     |     | 435 |     |     |     |     | 440 |     |     |     |     | 445 |     |     |     |
| Pro | Phe | Phe | Val | Asn | Val | Thr | His | Asn | Gly | Thr | Tyr | Gln | Cys | Gln | Ala |
|     | 450 |     |     |     |     | 455 |     |     |     |     | 460 |     |     |     |     |
| Ser | Ser | Ser | Arg | Gly | Lys | Tyr | Thr | Leu | Val | Val | Val | Met | Asp | Ile | Glu |
| 465 |     |     |     |     | 470 |     |     |     |     | 475 |     |     |     |     | 480 |
| Ala | Gly | Ser | Ser | His | Phe | Val | Pro | Val | Phe | Val | Ala | Val | Leu | Leu | Thr |
|     |     |     |     | 485 |     |     |     |     | 490 |     |     |     |     | 495 |     |
| Leu | Gly | Val | Val | Thr | Ile | Val | Leu | Ala | Leu | Met | Tyr | Val | Phe | Arg | Glu |
|     |     |     | 500 |     |     |     |     | 505 |     |     |     |     | 510 |     |     |
| His | Gln | Arg | Ser | Gly | Ser | Tyr | His | Val | Arg | Glu | Glu | Ser | Thr | Tyr | Leu |
|     |     | 515 |     |     |     |     | 520 |     |     |     |     | 525 |     |     |     |
| Pro | Leu | Thr | Ser | Met | Gln | Pro | Thr | Glu | Ala | Met | Gly | Glu | Glu | Pro | Ser |
|     | 530 |     |     |     |     | 535 |     |     |     |     | 540 |     |     |     |     |
| Arg | Ala | Glu |
| 545 |     |     |

( 2 ) INFORMATION FOR SEQ ID NO:7:

( i ) SEQUENCE CHARACTERISTICS:
        ( A ) LENGTH: 100 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:7:

| Thr | Leu | Gln | Thr | Val | Thr | Ile | Tyr | Ser | Glu | Pro | Ala | Pro | Asn | Val | Ile |
| --- | --- | --- | --- | --- | --- | --- | --- | --- | --- | --- | --- | --- | --- | --- | --- |
| 1 |   |   |   | 5 |   |   |   |   | 10 |   |   |   |   | 15 |   |
| Leu | Thr | Lys | Pro | Glu | Val | Ser | Glu | Gly | Thr | Glu | Val | Thr | Val | Lys | Cys |
|   |   |   | 20 |   |   |   |   | 25 |   |   |   |   | 30 |   |   |
| Glu | Ala | Met | Pro | Arg | Ala | Lys | Val | Thr | Leu | Asn | Gly | Val | Pro | Ala | Gln |
|   |   | 35 |   |   |   |   | 40 |   |   |   |   | 45 |   |   |   |
| Pro | Leu | Gly | Pro | Arg | Ala | Gln | Leu | Leu | Leu | Lys | Ala | Thr | Pro | Glu | Asp |
|   | 50 |   |   |   |   | 55 |   |   |   |   | 60 |   |   |   |   |
| Asn | Gly | Arg | Ser | Phe | Ser | Cys | Ser | Ala | Thr | Leu | Glu | Val | Ala | Gly | Gln |
| 65 |   |   |   |   | 70 |   |   |   |   | 75 |   |   |   |   | 80 |
| Leu | Ile | His | Lys | Asn | Gln | Thr | Arg | Glu | Leu | Arg | Val | Leu | Tyr | Gly | Pro |
|   |   |   |   | 85 |   |   |   |   | 90 |   |   |   |   | 95 |   |
| Arg | Leu | Asp | Glu |
|   |   |   | 100 |

( 2 ) INFORMATION FOR SEQ ID NO:8:

( i ) SEQUENCE CHARACTERISTICS:
        ( A ) LENGTH: 56 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:8:

| Thr | Arg | Gln | Ile | His | Pro | Gly | Arg | Gly | Asp | Gly | His | Leu | Arg | Leu | Gly |
|---|---|---|---|---|---|---|---|---|---|---|---|---|---|---|---|
| 1 | | | | 5 | | | | | 10 | | | | | 15 | |
| Ala | Pro | Thr | Leu | Ser | Pro | Val | Phe | Val | Ala | Val | Leu | Leu | Thr | Leu | Gly |
| | | | 20 | | | | 25 | | | | | | 30 | | |
| Val | Val | Thr | Ile | Val | Leu | Ala | Leu | Met | Tyr | Val | Phe | Arg | Glu | His | Gln |
| | | 35 | | | | | 40 | | | | | 45 | | | |
| Arg | Ser | Gly | Ser | Tyr | His | Val | Arg | | | | | | | | |
| | 50 | | | | | 55 | | | | | | | | | |

( 2 ) INFORMATION FOR SEQ ID NO:9:

( i ) SEQUENCE CHARACTERISTICS:
        ( A ) LENGTH: 132 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:9:

| Arg | Asp | Cys | Pro | Gly | Asn | Trp | Thr | Trp | Pro | Glu | Asn | Ser | Gln | Gln | Thr |
|---|---|---|---|---|---|---|---|---|---|---|---|---|---|---|---|
| 1 | | | | 5 | | | | | 10 | | | | | 15 | |
| Pro | Met | Cys | Gln | Ala | Trp | Gly | Asn | Pro | Leu | Pro | Glu | Leu | Lys | Cys | Leu |
| | | | 20 | | | | 25 | | | | | | 30 | | |
| Lys | Asp | Gly | Thr | Phe | Pro | Leu | Pro | Ile | Gly | Glu | Ser | Val | Thr | Val | Thr |
| | | | 35 | | | | 40 | | | | | 45 | | | |
| Arg | Asp | Leu | Glu | Gly | Thr | Tyr | Leu | Cys | Arg | Ala | Arg | Ser | Thr | Gln | Gly |
| | | 50 | | | | | 55 | | | | | 60 | | | |
| Glu | Val | Thr | Arg | Glu | Val | Thr | Val | Asn | Val | Leu | Ser | Pro | Arg | Tyr | Glu |
| 65 | | | | | 70 | | | | | 75 | | | | | 80 |
| Ile | Val | Ile | Ile | Thr | Val | Val | Ala | Ala | Ala | Val | Ile | Asn | Gly | Thr | Ala |
| | | | | 85 | | | | | 90 | | | | | 95 | |
| Gly | Leu | Ser | Thr | Tyr | Leu | Tyr | Asn | Arg | Gln | Arg | Lys | Ile | Lys | Lys | Tyr |
| | | | 100 | | | | | 105 | | | | | 110 | | |
| Arg | Leu | Gln | Gln | Ala | Gln | Lys | Gly | Thr | Pro | Met | Lys | Pro | Asn | Thr | Gln |
| | | | 115 | | | | | 120 | | | | | 125 | | |
| Ala | Thr | Pro | Pro | | | | | | | | | | | | |
| | | | 130 | | | | | | | | | | | | |

( 2 ) INFORMATION FOR SEQ ID NO:10:

( i ) SEQUENCE CHARACTERISTICS:
        ( A ) LENGTH: 125 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:10:

| Arg | Gly | Asn | Glu | Thr | Leu | His | Tyr | Glu | Thr | Phe | Gly | Lys | Ala | Ala | Pro |
|---|---|---|---|---|---|---|---|---|---|---|---|---|---|---|---|
| 1 | | | | 5 | | | | | 10 | | | | | 15 | |
| Ala | Pro | Gln | Glu | Ala | Thr | Ala | Thr | Phe | Asn | Ser | Thr | Ala | Asp | Arg | Glu |
| | | | 20 | | | | 25 | | | | | | 30 | | |
| Asp | Gly | His | Arg | Asn | Phe | Ser | Cys | Leu | Ala | Val | Leu | Asp | Leu | Met | Ser |
| | | | 35 | | | | 40 | | | | | 45 | | | |
| Arg | Gly | Gly | Asn | Ile | Phe | His | Lys | His | Ser | Ala | Pro | Lys | Met | Leu | Glu |

| | | | | 50 | | | | | 55 | | | | | 60 | |
|---|---|---|---|---|---|---|---|---|---|---|---|---|---|---|---|

Ile Tyr Glu Pro Val Ser Asp Ser Gln Met Tyr Ile Ile Val Thr Val
65                    70                    75                        80

Val Ser Val Leu Leu Ser Leu Phe Val Thr Ser Val Leu Leu Cys Phe
                      85                    90                        95

Ile Phe Gly Gln His Leu Arg Gln Gln Arg Met Gly Thr Tyr Gly Val
                100                    105                    110

Arg Ala Ala Trp Arg Arg Leu Pro Gln Ala Phe Arg Pro
                115                    120                    125

( 2 ) INFORMATION FOR SEQ ID NO:11:

( i ) SEQUENCE CHARACTERISTICS:
        ( A ) LENGTH: 100 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:11:

Met Ala Pro Ser Ser Pro Arg Pro Ala Leu Pro Ala Leu Leu Val Leu
1                     5                    10                    15

Leu Gly Ala Leu Phe Pro Gly Pro Gly Asn Ala Gln Thr Ser Val Ser
                  20                    25                    30

Pro Ser Lys Val Ile Leu Pro Arg Gly Gly Ser Val Leu Val Thr Cys
                35                    40                    45

Ser Thr Ser Cys Asp Gln Pro Lys Leu Leu Gly Ile Glu Thr Pro Leu
    50                    55                    60

Pro Lys Lys Glu Leu Leu Leu Pro Gly Asn Asn Arg Lys Val Tyr Glu
65                    70                    75                    80

Leu Ser Asn Val Gln Glu Asp Ser Gln Pro Met Cys Tyr Ser Asn Cys
                85                    90                    95

Pro Asp Gly Gln
                100

( 2 ) INFORMATION FOR SEQ ID NO:12:

( i ) SEQUENCE CHARACTERISTICS:
        ( A ) LENGTH: 99 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:12:

Met Ser Ser Phe Gly Tyr Arg Thr Leu Thr Val Ala Leu Phe Thr Leu
1                     5                    10                    15

Ile Cys Cys Pro Gly Ser Asp Glu Lys Val Glu Glu Val His Val Arg
                20                    25                    30

Pro Lys Lys Leu Ala Val Glu Pro Lys Gly Ser Leu Glu Val Asn Cys
                35                    40                    45

Ser Thr Thr Cys Asn Gln Pro Glu Val Gly Gly Leu Glu Thr Ser Leu
    50                    55                    60

Asn Lys Ile Leu Leu Asp Glu Gln Ala Gln Trp Lys His Tyr Leu Val
65                    70                    75                    80

Ser Asn Ile Ser His Asp Thr Val Leu Cys His Phe Thr Cys Ser Gly
                85                    90                    95

Lys Gln Glu (2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
ARNGANGTCT CCAGRGCDAT YTT                                    23
```

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
TTNAGRTGYT GNGGRCANGT NGCNC                                  25
```

What is claimed is:

1. A method of reducing inflammation, wherein said inflammation is mediated by ICAM-3, in a subject in need thereof comprising:
   providing to a subject in need of such treatment a pharmaceutical composition comprising an effective amount of an ICAM-3 modulating agent and a pharmaceutically acceptable carrier;
   wherein said ICAM-3 modulating a(gent is selected from the group consisting of:
   (a) an antibody capable of binding ICAM-3, wherein said antibody inhibits aggregation of ICAM-3-expressing, ICAM-1 and ICAM-2 non-expressing (cells;
   (b) a fragment of said antibody, said fragment being capable of binding ICAM-3; and
   (c) a soluble fragment of ICAM-3 said fragment being capable of binding LIFA-1.

2. The method of reducing inflammation as claimed in claim 1, wherein said inflammation comprises a reaction of the specific defense system.

3. The method of claim 2 wherein said inflammatory response is specific inflammation in response to a condition selected from the group consisting of: delayed-type hypersensitivity reaction, psoriasis, an autoimmune disease, organ transplant, and tissue graft rejection.

4. The method of claim 3 wherein said organ transplant is a solid organ transplant.

5. The method of claim 4 wherein said organ transplant is a kidney transplant.

6. The method of claim 3 wherein said organ transplant is a non-solid organ transplant.

7. The method of claim 6 wherein said non-solid organ transplant is a bone marrow transplant.

8. The method claim of 3, wherein said autoimmune disease is selected from the group consisting of: Reynaud's syndrome, autoimmune thyroiditis, experimental allergic encephalomyelitis (EAE), multiple sclerosis, rheumatoid arthritis and lupus erythematosus.

9. The method of reducing inflammation as claimed in claim 1, wherein said inflammation comprises a reaction of the non-specific defense system.

10. The method of claim 9, wherein said inflammation is non-specific inflammation in response to a condition selected from the group consisting of: adult respiratory distress syndrome (ARDS), multiple organ injury syndromes secondary to septicemia, trauma or hemorrhage, reperfusion injury of myocardial or other tissues, acute glomerulonephritis, reactive arthritis, dermatoses with acute inflammatory components, acute purulent meningitis or other central nervous system inflammatory disorders, stroke, thermal injury, hemodialysis, leukapheresis, ulcerative colitis, Crohn's disease, necrotizing enterocolitis, granulocyte transfusion associated syndromes, and cytokine-induced toxicity.

11. The method of reducing inflammation as claimed in claim 1, wherein said ICAM-3 modulating agent is a soluble fragment ICAM-3, said fragment being capable of binding LFA-1.

12. A method of reducing the metastasis of a hematopoietic tumor cell, in a subject in need thereof, comprising:
   providing to a subject in need of such treatment a pharmaceutical composition comprising an effective amount of an ICAM-3 modulating agent and a pharmaceutically acceptable carrier;
   wherein said ICAM-3 modulating agent is selected from the group consisting of:
   (a) an antibody capable of binding ICAM-3, wherein said antibody inhibits aggregation of ICAM-3-expressing, ICAM-1 and ICAM-2 non-expressing cells;
   (b) a fragment of said antibody, said fragment being capable of binding ICAM-3; and
   (c) a soluble fragment of ICAM-3 said fragment being capable of binding LFA-1; and
   further wherein said cell requires a functional member of the CD18 family for migration.

13. The method of reducing the metastasis of a hematopoietic tumor cell as claimed in claim 12, wherein said ICAM-3 modulating agent is a soluble fragment ICAM-3, said fragment being capable of binding LFA-1.

14. The method of reducing the metastasis of a hematopoietic tumor cell as claimed in claim 13, wherein said ICAM-3 modulating agent is a soluble fragment of ICAM-3 comprising domains 1–5 of ICAM-3.

15. A method of reducing syncytia formation caused by HIV infection in a subject in need of treatment for HIV infection, comprising:

providing to a subject in need of treatment for HIV infection, a pharmaceutical composition comprising an effective amount of an ICAM-3 modulating agent and a pharmaceutically acceptable carrier, wherein said pharmaceutical composition further comprises an additional agent selected from the group consisting of: anti-ICAM-1 antibody, an anti-ICAM-2 antibody, ICAM-1 or a soluble fragment thereof; and ICAM-2 or a soluble fragment thereof; and further wherein said ICAM-3 modulating agent is selected from the group consisting of:
(a) an antibody capable of binding ICAM-3, wherein said antibody inhibits aggregation of ICAM-3-expressing, ICAM-1 and ICAM-2 non-expressing cells;
(b) a fragment of said antibody, said fragment being capable of binding ICAM-3; and
(c) a soluble fragment of ICAM-3 said fragment being capable of binding LFA-1.

16. The method of reducing syncytia formation as claimed in claim 15, wherein said ICAM-3 modulating agent is a soluble fragment ICAM-3, said fragment being capable of binding LEA-1.

17. The method of claim 16 wherein said HIV is HIV-1.

18. A method of suppressing cellular migration associated with asthma, wherein said migration is mediated by ICAM-3, in a subject in need of treatment therefor, comprising:

providing to said subject a pharmaceutical composition comprising an effective amount of an ICAM-3 modulating agent and a pharmaceutically acceptable carrier;
wherein said ICAM-3 modulating agent is selected from the group consisting of:
(a) an antibody capable of binding ICAM-3, wherein said antibody inhibits aggregation of ICAM-3 expressing, ICAM-1 and ICAM-2 non-expressing cells;
(b) a fragment of said antibody, said fragment being capable of binding ICAM-3; and
(c) a soluble fragment of ICAM-3 said fragment being capable of binding LFA-1.

19. A method of suppressing cellular migration associated with asthma as claimed in claim 18, wherein said ICAM-3 modulating agent is a soluble fragment of ICAM-3 comprising ICAM-3 domains 1–5.

20. The method of suppressing cellular migration associated with asthma as claimed in claim 18, wherein said pharmaceutical composition further comprises one or more additional anti-asthma agents.

21. The method of suppressing cellular migration associated with asthma as claimed in claim 20, wherein said anti-asthma agent is a methylxanthine, a β-adrenergic agonist, a glucocorticoid, a chromone, or an anticholinergic compound.

22. The method of suppressing the cellular migration associated with asthma as claimed in claim 20, wherein said anti-asthma agent is selected from the group consisting of: theophylline, catecholamine, resorcinol, saligenin, ephedrine, atropine, cromolyn sodium, and hydrocortisone.

23. The method of suppressing the cellular migration associated with asthma as claimed in claim 20, wherein said anti-asthma agent is present in said pharmaceutical composition at a suboptimal level.

24. The method of any one of claims 1–23, 1–23, wherein said method additionally comprises the administration of one or more agents selected from the group consisting of: an antibody capable of binding to LFA-1; a fragment of said antibody, said fragment being capable of binding to LFA-1; an antibody capable of binding to ICAM-1; a fragment of said antibody, said fragment being capable of binding to ICAM-1; an antibody capable of binding to ICAM-2; a fragment of said antibody, said fragment being capable of binding to ICAM-2.

25. The method of any one of claims 1–23, 1–23, wherein said ICAM-3 modulating agent is administered by enteral means, parenteral means, topical means, inhalation means, or intranasal means.

26. The method of claim 25 wherein said parenteral means is intramuscular, intravenous or subcutaneous.

27. The method of any one of claims 1–23, 1–23, wherein said ICAM-3 modulating agent is administered prophylactically.

28. The method of any of claims 1–23, 1–23 1–23, wherein said ICAM-3 modulating agent is administered therapeutically.

* * * * *

UNITED STATES PATENT AND TRADEMARK OFFICE
CERTIFICATE OF CORRECTION

PATENT NO. : 5,891,841
DATED : April 6, 1999
INVENTOR(S) : DeFougerolles, et. al.

It is certified that error appears in the above-identified patent and that said Letters Patent is hereby corrected as shown below:

Title page, item [60] ("Related U.S. Application Data"), please delete "Division of Ser. No. 38,990, filed as PCT/US92/04896 Nov. 6, 1992, abandoned, which is a continuation-in-part of Ser. No.712,879, Jun. 11, 1991, abandoned" and insert therein "Division of Ser. No. 08/038,990, Dec. 23, 1992, which is a continuation-in-part of PCT Application No. US92/04896, Jun. 11, 1992, which is a continuation-in-part of Ser. No.07/712,879, June 11, 1991, abandoned."

In column 58, claim 24, line 1, after "claims 1-23," please delete "1-23,".
In column 58, claim 25, line 1, after "claims 1-23," please delete "1-23,".
In column 58, claim 27, line 1, after "claims 1-23," please delete "1-23,".
In column 58, claim 28, line 1, after "claims 1-23," please delete "1-23 1-23,".

Signed and Sealed this

Twenty-first Day of September, 1999

*Attest:*

Q. TODD DICKINSON

*Attesting Officer*     *Acting Commissioner of Patents and Trademarks*